United States Patent
Yoo

(10) Patent No.: US 8,951,779 B2
(45) Date of Patent: *Feb. 10, 2015

(54) BIO MEMORY DISC AND BIO MEMORY DISC DRIVE APPARATUS, AND ASSAY METHOD USING THE SAME

(75) Inventor: Jae-chern Yoo, Gyeongsangbuk-do (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 454 days.

This patent is subject to a terminal disclaimer.

(21) Appl. No.: 12/158,848

(22) PCT Filed: Dec. 21, 2006

(86) PCT No.: PCT/KR2006/005636
§ 371 (c)(1),
(2), (4) Date: Jun. 23, 2008

(87) PCT Pub. No.: WO2007/073107
PCT Pub. Date: Jun. 28, 2007

(65) Prior Publication Data
US 2009/0253130 A1 Oct. 8, 2009

(30) Foreign Application Priority Data
Dec. 21, 2005 (KR) ........................ 10-2005-0128469

(51) Int. Cl.
*C12M 1/34* (2006.01)
*C12Q 1/68* (2006.01)
(Continued)

(52) U.S. Cl.
CPC ...... *G01N 35/00069* (2013.01); *B01F 13/0059* (2013.01); *B01F 13/0809* (2013.01); *B01L 3/502715* (2013.01); *B01L 3/502723* (2013.01); *B01L 3/502738* (2013.01); *B01L 3/545* (2013.01); *B01L 3/502753* (2013.01); *B01L 2200/0684* (2013.01); *B01L 2300/023* (2013.01); *B01L 2300/024* (2013.01); *B01L 2300/0654* (2013.01); *B01L 2300/0806* (2013.01);
(Continued)

(58) Field of Classification Search
None
See application file for complete search history.

(56) References Cited

U.S. PATENT DOCUMENTS 5,497,464 A * 3/1996 Yeh .............................. 710/303
6,361,944 B1 * 3/2002 Mirkin et al. ................ 435/6.11
(Continued)

FOREIGN PATENT DOCUMENTS

JP 8-121636 5/1996
JP 2000-515632 11/2000
(Continued)

OTHER PUBLICATIONS

Japanese Decision of Grant issued May 22, 2012 in corresponding Japanese Patent Application No. 2008-547113.
(Continued)

*Primary Examiner* — Betty Forman
(74) *Attorney, Agent, or Firm* — Staas & Halsey LLP

(57) ABSTRACT

The present invention provides a bio memory disc where a lab-on-a-chip process system including an assay-diagnosis unit, a nucleic acid hybridization assay unit, or an immunoassay unit and a semiconductor memory is disposed, a bio memory disc drive apparatus including a controller for controlling and driving an optical disc including CD or DVD and the bio memory disc and an assay method using the same.

15 Claims, 49 Drawing Sheets

(51) Int. Cl.
  *G01N 21/00* (2006.01)
  *G01N 35/00* (2006.01)
  *B01F 13/00* (2006.01)
  *B01F 13/08* (2006.01)
  *B01L 3/00* (2006.01)

(52) U.S. Cl.
  CPC .. *B01L2400/0409* (2013.01); *B01L 2400/0633* (2013.01)
  USPC ........... 435/287.2; 435/4; 435/6.1; 422/82.05

(56) References Cited

U.S. PATENT DOCUMENTS

| | | | | |
|---|---|---|---|---|
| 7,635,585 | B2* | 12/2009 | Yoo | 435/283.1 |
| 8,097,450 | B2* | 1/2012 | Yoo | 435/288.5 |
| 8,263,386 | B2* | 9/2012 | Yoo | 435/283.1 |
| 8,480,980 | B2* | 7/2013 | Yoo | 422/537 |
| 2003/0054376 | A1* | 3/2003 | Mullis et al. | 435/6 |
| 2003/0177380 | A1* | 9/2003 | Woods | 713/200 |
| 2003/0224377 | A1* | 12/2003 | Wengel et al. | 435/6 |
| 2004/0155213 | A1* | 8/2004 | Yoo | 251/65 |
| 2006/0040273 | A1* | 2/2006 | Chaiken et al. | 435/6 |
| 2008/0190219 | A1* | 8/2008 | Jensen et al. | 73/864.71 |
| 2009/0163367 | A1* | 6/2009 | Yoo | 506/7 |
| 2010/0055771 | A1* | 3/2010 | Yoo | 435/287.2 |

FOREIGN PATENT DOCUMENTS

| | | |
|---|---|---|
| JP | 2003-84001 | 3/2003 |
| JP | 2004-73995 | 3/2004 |
| JP | 2005-514043 | 5/2005 |
| WO | 03/080868 A1 | 10/2003 |
| WO | WO 03/080868 * | 10/2003 |
| WO | 2005/003723 A2 | 1/2005 |

OTHER PUBLICATIONS

Korean Office Action issued Nov. 12, 2012, in corresponding Japanese Patent Application No. 10-2008-7017126.

Japanese Office Action issued Oct. 25, 2011 in corresponding Japanese Patent Application No. 2008-547113.

* cited by examiner

<Process1: before injection of blood>
<Process2: after injection of blood>
<Process3: after centrifugal separation>
<Process4: after transfer of serum>

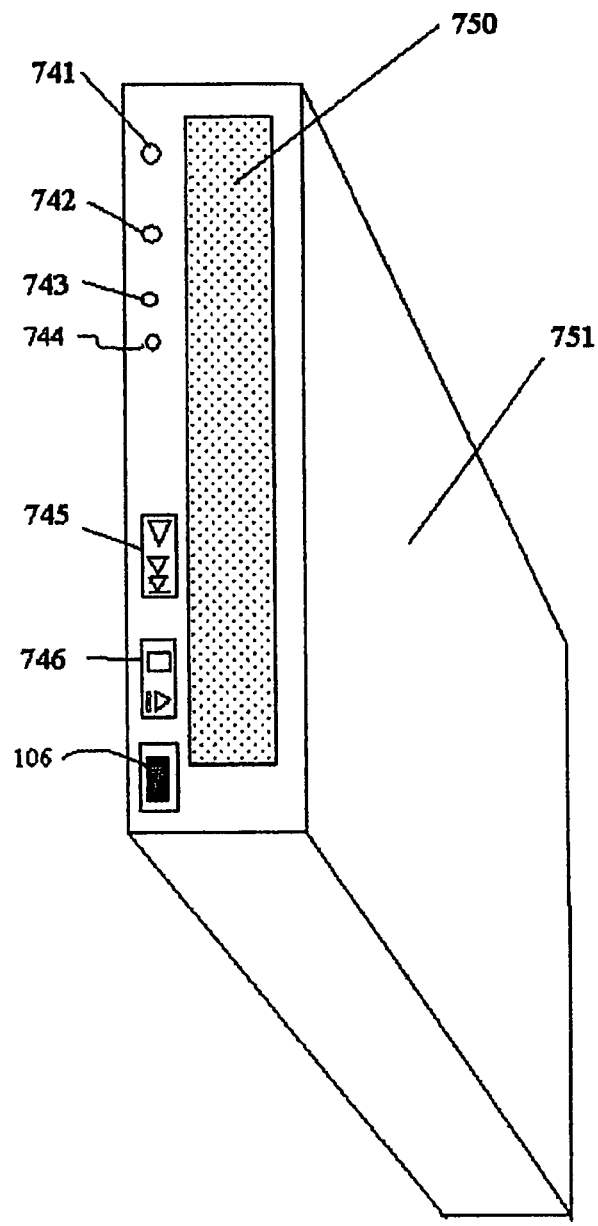

BIO MEMORY DISC AND BIO MEMORY DISC DRIVE APPARATUS, AND ASSAY METHOD USING THE SAME

This application claims the benefit under 35 U.S.C. Section 371, of International Application Number PCT/KR2006/005636, filed Dec. 21, 2006, which claimed priority to Korean Application No. 10-2005-0128469, filed Dec. 21, 2005 before the Korean Intellectual Property Office, the contents of which are incorporated herein by reference.

TECHNICAL FIELD

The present invention relates to a bio memory disc where a lab-on-a-chip process system including an assay-diagnosis unit, a nucleic acid hybridization assay unit, or an immuno-assay unit and a semiconductor memory is disposed, a bio memory disc drive apparatus including a controller for controlling and driving an optical disc including CD or DVD and the bio memory disc and an assay method using the same.

In the present invention, the bio memory disc and the bio memory disc drive apparatus are referred to as BMD and BMD drive apparatus, respectively.

In addition, in the present invention, a disc on which only the lab-on-a-chip process system is disposed is called a bio disc; a disc on which only the semiconductor memory is disposed is called a memory disc; and the bio disc and the memory disc are collectively called a bio memory disc.

BACKGROUND ART

The present invention is a continued application of: International Patent Application No. PCT/KR02/00126, entitled "Nucleic acid hybridization assay method and device using cleavage technique responsive to complementary double strand of nucleic acids or oligonucleotides", which was filed on Jan. 27, 2002 and claims the priority of Korean Patent Application No. 10-2001-0003956 entitled "Nucleic acid hybridization assay method and device using cleavage technique responsive to complementary double strand or single strand of nucleic acids or oligonucleotides", filed on Jan. 27, 2001; International Patent Application No. PCT/KR02/01035 entitled "Micro valve apparatus using micro bead and method for controlling the same", which was filed on May 31, 2002 and claims the priority of Korean Patent Application No. 10-2001-0031284 entitled "Micro valve apparatus using micro bead and method for controlling the same", filed on May 31, 2001; Korean Patent Application No. 10-2002-17558 entitled "Bio disc and bio drive apparatus and assay method using the same", filed on Mar. 27, 2002; Korean Patent Application No. 10-2005-0038765 entitled "Digital bio disc and digital bio drive apparatus and assay method using the same", filed on May 6, 2005; and Korean Patent Application No. 10-2005-0057513 entitled "DVD (Bio-DVD) drive apparatus and assay method using the same", filed on Jun. 26, 2005. The disclosures of the above previous applications are incorporated herein by reference in their entirety.

In the invention of the previously filed application, the nucleic acid hybridization assay method and device using a cleavage technique responsive to a complementary double strand or single strand of—nucleic acids are applicable to diverse quantitative or qualitative assay devices. In addition, the micro valve is an essential element to control the flow of fluid in a lab-on-a-chip.

In the invention of the previously filed application, the nucleic acid assay device may comprise a detector including an optical device, an electrochemical device, or an impedance measurement device to detect confined signal elements of cleaved signal elements. The detected results can be digitized as computer executable software and provided through an established communications network, such as the Internet, to a patient or a doctor. In this manner, a remote diagnostic system ensuring convenience to both patient and doctor can be implemented based on the nucleic acid assay device. An impedance measurement for the detector may include inter-digitated array electrodes with confined signal elements or cleavable signal elements, as disclosed in the previous application. In the invention of the previously filed application, a fluorescence detecting method for detecting a fluorescence label is disclosed.

In the invention of the previously filed application, a solid-state substrate (or a solid-state container) including a channel for flowing a fluid on a surface of a substrate, a chamber for storing a buffer solution, a fluid hole for connecting the channel, and an assay site where an array of bio materials are disposed; a valve for closing and opening the fluid hole; at least one preparation chamber for preparing a serum or DNA sample from blood; a PCR chamber for amplifying the DNA sample; and various enzymes are disclosed. In the invention of the previously filed application, an azimuthal direction valve searching operation is disclosed. The azimuthal direction valve searching operation is performed by slowing rotating a spindle motor with the slider being stopped or by repeating short rotating and stopping of the spindle motor.

In the invention of the previously filed application, a method of identifying a model or a version of a bio disc by using a barcode pattern of production ID (identification) is disclosed.

As a continued application from the previous applications, the present invention relates to a bio memory disc where a lab-on-a-chip process system used for various assay-diagnosis units, a nucleic acid hybridization assay unit, and a immuno-assay unit and/or semiconductor memories are disposed; a bio memory disc drive apparatus for driving and controlling the bio memory disc and an optical disc (a CD or a DVD); and an assay method using the same.

Most clinical diagnostic assay devices developed so far for the detection of small quantities of analytes in fluids are used in serial or parallel connection with multiple-sample preparation and automated reagent addition devices for the simultaneous analysis of numerous test samples with higher efficiency. Such automated reagent preparation devices and automated multiplex analyzers are often integrated into a single device. Clinical laboratory analyzers of this type can accurately perform hundreds of assays using small quantities of samples and reagents in one hour automatically or semi-automatically.

However, these analyzers are expensive and only centralized laboratories and hospitals can afford them. Such centralization necessitates sample transport to the laboratory or hospital and often precludes urgent or emergent analysis of time-critical samples.

Thus, to address these problems, there is an increasing need for clinical analyzers which are cheap and easy-to-handle for everyone, such as clinical analyzers suitable for use at the patient bedside of in the patient's home without dedicated detectors.

As ultra-high speed Internet and large-storage-capacity semiconductor memory are widely provided, a simple storage media such as a CD, a DVD, or other optical discs are not attractive in the market. In addition, media fusion of the optical disc and the semiconductor memory are highly demanded.

Therefore, a bio memory disc on which a lab-on-a-chip process system and/or a semiconductor memory are disposed and a bio memory disc drive apparatus for driving and controlling an optical disc (a CD and a DVD) and the bio memory disc are needed.

In the present invention, a disc on which only the lab-on-a-chip process system is disposed is called a bio disc; a disc on which only the semiconductor memory is called a memory disc; and the bio disc and the memory disc are collectively called a bio memory disc.

The bio memory disc can be used as a substitute for a conventional DVD RAM. The current DVD RAM has a maximum storage capacity of 9.4 GB. However, since a semiconductor memory having a storage capacity of 32 GB has already been commercially provided, a bio memory disc including the semiconductor memory can have a high storage capacity. In addition, a plurality of semiconductor memories are integrated in the bio memory disc so as to increase storage capacity, so that the bio memory disc can be used as a substitute for an existing hard disc of a computer.

The general optical disc such a standard compact disc is constructed by stacking a 12 cm polycarbonate substrate, a reflective metal layer, a protective lacquer coating layer, and the like. In addition, a continuous spiral groove is formed as a reference alignment guide for incident laser is formed on the polycarbonate substrate. The CD and CD-ROM formats are in accordance with the industrial standard ISO 9660.

As is widely known to one of ordinary skilled in the art, information written to general optical discs, such as audio CDs, game CDs, refractivity in their dye layer. In a common CD using a differential reflectivity detection method, indentations of pits are formed in the CD to a depth on the order of one-eighth to one-quarter of the wavelength of an incident laser beam.

Various technologies regarding CD-based assay devices have been disclosed: "Optical confocal compact scanning optical microscope based on compact disc technology" (Applied Optics, Vol. 30, No. 10, 1991), "Gradient-index objectives for CD applications" (Applied Optics, Vol. 26, Issue 7, 1987), and "Miniature scanning optical microscope based on compact disc technology" (Proc. Soc. Photo-opt. instrument Eng. page 1139-1169, 1989).

Patents regarding CD-based assay devices include U.S. Pat. No. 4,279,862 entitled "Centrifugal photometric analyzer" (published on Jul. 12, 1981) and U.S. Pat. No. 4,141,954 entitled "Reaction tube assembly for automatic analyzer" (published on Feb. 27, 1979).

GB 1075800 (published on Jul. 12, 1967), entitled "Disc for centrifuge", discloses a device for flowing a sample fluid supplied via n inject hole of a disc over its surface by centrifugal force. EP 3335946 (published on Apr. 12, 1965), entitled "Separating disks for centrifuge", discloses an apparatus for separating fluid samples injected via an inject hole of a disc by inducing flow of the samples through channels or chambers formed in the disc by centrifugal force.

U.S. Pat. No. 4,311,039 (published on Jan. 19, 1982), entitled "Disc centrifuge photo-sediment meter", discloses a disc type chemical assay device using centrifugal force and optical detection.

However, these discs are not provided with mechanical or physical valves, so that the fluid flow cannot be controlled during a high-speed rotation for separation of serum or DNA from blood. Therefore, these discs are not suitable for automation of diagnosis and assay, so that these discs cannot be suitably used for a lab-on-a-chip process system. In addition, an MP3 player using the semiconductor memory cannot reproduce a CD and a DVD. On the other hand, a CD player or a DVD player cannot reproduce the semiconductor memory but the optical disc.

However, the bio memory disc drive apparatus according to the present invention can reproduce a semiconductor memory as well as an optical disc (a CD and a DVD).

The bio memory disc according to the present invention can be used as a substitute for a conventional DVD RAM. The current DVD RAM has a maximum storage capacity of 9.4 GB. However, since a semiconductor memory having a storage capacity of 32 GB has already been commercially provided, a bio memory disc including the semiconductor memory can have a storage capacity higher than that of the DVD RAM. Accordingly, the bio memory disc can be used as a substitute for an existing hard disc of a computer.

DISCLOSURE OF INVENTION

In order to solve the above-described problem, the present invention provides a bio memory disc where a lab-on-a-chip process system used for various assay-diagnosis units, a nucleic acid hybridization assay unit, and a immuno-assay unit and/or semiconductor memories are disposed; a bio memory disc drive apparatus for driving and controlling the bio memory disc and an optical disc (a CD or a DVD); and an assay method using the same. The semiconductor memory can store (record) digital information of audio and video, and the digital information can be reproduced (read out) by the bio memory disc drive apparatus. In addition, the semiconductor memory can be used as a substitute for the DVD RAM. The current DVD RAM has a maximum storage capacity of 9.4 GB. However, since a semiconductor memory having a storage capacity of 32 GB has already been commercially provided, a bio memory disc including the semiconductor memory can have a storage capacity higher than that of the DVD RAM. In addition, a plurality of semiconductor memories are integrated in the bio memory disc so as to increase storage capacity, so that the bio memory disc can be used as a substitute for an existing hard disc of a computer.

In the present invention, a disc on which only the lab-on-a-chip process system is disposed is called a bio disc; a disc on which only the semiconductor memory is called a memory disc; and the bio disc and the memory disc are collectively called a bio memory disc.

According to an aspect of the present invention, there is a provided a bio memory disc on which a semiconductor memory is designed and disposed.

In the bio memory disc according to the present invention, a lab-on-a-chip process system may be further disposed on the disc, and wherein the lab-on-a-chip process system includes: a sample inlet; a chamber for containing a buffer solution or a reaction solution; an assay site where bio materials are fixed on a substrate; a channel through which a fluid flows between the chamber and the assay site; a fluid hole for connecting the channel; and a valve for opening and closing the fluid hole.

The term "assay site" used throughout the specification is referred to as an "array chamber" having a meaning that bio materials are arrayed thereon, or "hybridization chamber" or an "antigen-antibody reaction chamber" having a meaning that a specific binding reaction of two bio materials, such as a ligand-receptor reaction, a hybridization reaction, or an antigen-antibody reaction takes place therein.

The material of the bio memory disc may be a plastic substrate such as a polycarbonate or silicon wafer. The polycarbonate substrate or silicon wafer can be modified to suit to a bio memory disc, which are thin film type assay devices, for detecting a small quantity of an analyte in a fluid sample for the diagnostic purpose. In this case, instead of pits and a dye layer, a lab-on-a-chip process system including channels as fluid flow paths and chambers as buffer reservoirs is formed in a surface of a polycarbonate substrate or silicon wafer through injection molding or photolithography. In addition, micro valves for controlling fluid flow through the channel and flow rate and an electronic controlling method of the micro valves are needed. The bio memory disc of the present invention consists of a semiconductor memory as well as a lab-on-a-chip process system to have a function of memorizing digital information, such as audio and video data. The digital information can be played or read by a bio memory disc drive apparatus of the present invention. For this purpose, the bio memory disc may be controlled by a central controller in the bio memory disc drive apparatus. The central controller can drive and operate a conventional optical disc such as CD or DVD as well as a bio memory disc.

In the bio memory disc according to the present invention, the semiconductor memory may be a flash memory. The semiconductor may replace or supplement the information memory function of the DVD RAM or hard disc of a computer.

In the bio memory disc according to, the semiconductor memory may further include a memory optical conversion module which provides information stored in the semiconductor memory to a bio memory disc drive apparatus or provides to-be-recorded information from the bio memory disc drive apparatus to the semiconductor memory.

In addition, the semiconductor memory is optically interfaced to the optical communication unit disposed in the bio memory disc drive apparatus through the memory optical conversion module.

In the bio memory disc according to the present invention, the memory optical conversion module may provide information read from the assay site to an optical communication unit of the bio memory disc drive apparatus.

In the bio memory disc according to the present invention, the memory optical conversion module may convert digital reproducing information including a digital data, audio information, or image information stored in the semiconductor memory to an optical signal and transmits the optical signal to an optical communication unit of the bio memory disc drive apparatus.

In the bio memory disc according to the present invention, the memory optical conversion module may receive digital information from an optical communication unit of the bio memory disc drive apparatus and converts the digital information to an electrical signal to record and store the digital information in the semiconductor memory.

The bio memory disc according to the present invention may further comprise a power supply means for receiving an external power.

In the bio memory disc according to the present invention, the power supply means may be constructed with an electrical contact means which is disposed at the center of the bio memory disc to provide an external contact.

In the bio memory disc according to the present invention, the power supply means may be a wireless power supply unit.

In the bio memory disc according to the present invention, the wireless power supply unit may further include an induction coil disposed on the bio memory disc, wherein the power is supplied by a current induced through electromagnetic induction between an external magnetic field generating coil and the induction coil.

In the bio memory disc according to the present invention, the wireless power supply unit may further include an induction coil disposed on the bio memory disc, wherein the power is supplied by a current induced through electromagnetic induction between at least one external permanent magnet and the induction coil during a high-speed rotation of the bio memory disc.

In the bio memory disc according to the present invention, the wireless power supply unit may be constructed with a solar cell disposed on the bio memory disc.

The bio memory disc according to the present invention may further comprise a disc input/output unit which provides an interface for uploading contents of the semiconductor memory to an external digital information storage device (for example, a PC) or a display apparatus (for example, a TV or a LCD monitor) or downloading digital information from the external digital information storage device or the display apparatus.

In the bio memory disc according to the present invention, the disc input/output unit may have a USB (universal serial bus) communication protocol, an IEEE 1394 communication protocol, or Internet communication protocol.

The bio memory disc according to the present invention may further comprise a micro controller or software having a multimedia reproducing function, a multimedia storing function, and a multimedia connecting function.

The bio memory disc according to the present invention may further comprise a speaker and a microphone so as to allow an audio information content stored in the semiconductor memory to be converted to an analog signal for audio reproduction or to allow the audio to be converted to digital audio information and store the digital audio information in the semiconductor memory.

The bio memory disc according to the present invention may further comprise an image sensor so that image information is stored in the semiconductor memory.

The bio memory disc according to the present invention may further comprise an LCD display unit so that the image information reproduced from the semiconductor memory is displayed.

In the bio memory disc according to the present invention, a digital multimedia broadcast unit, a TV/radio receiver, or an mobile phone transceiver may be provided within a body of the disc, so that the bio memory disc can performs a DMB function, a TV/radio receiving function, a mobile phone transceiver function, or an electrical calculating function.

The bio memory disc according to the present invention may further comprise a mirror.

The bio memory disc according to the present invention may further comprise an IR receiver can receives an IR signal from a remote controller.

The bio memory disc according to the present invention may further comprise a function-associated key pad.

In the bio memory disc according to the present invention, the key pad may include at least one selected from a play button, a record button, a search button, a forward button, a reverse button, a stop button, a pause button, a power button, a conversation button, a conversation stop button, a menu button, a ten-key button, a camera on button, a TV on/off button, a TV channel up/down button, a volume up/down button, a recording button, a and a keyboard button.

In the bio memory disc according to the present invention, the key pad may further include a multi-functional button including a jog shuttle button and a four-direction arrow button.

According to another aspect of the present invention, there is provided a bio memory disc comprising a lab-on-a-chip process system is further disposed on the disc, wherein the lab-on-a-chip process system includes: a sample inlet; a chamber for containing a buffer solution or a reaction solution; an assay site where bio materials are fixed on a substrate; a channel through which a fluid flows between the chamber and the assay site; a fluid hole for connecting the channel; and a valve for opening and closing the fluid hole, and wherein the valve is provided with a liquid valve which is constructed with a channel which is curved in the inward direction of the disc so as to prevent leakage of a liquid during a high speed rotation of the bio memory disc.

In the bio memory disc according to the present invention, the liquid valve may have a V-shaped channel provided to an outlet of the valve.

According to another aspect of the present invention, there is provided a bio memory disc comprising a lab-on-a-chip process system is further disposed on the disc, wherein the lab-on-a-chip process system includes: a sample inlet; a chamber for containing a buffer solution or a reaction solution; an assay site where bio materials are fixed on a substrate; a channel through which a fluid flows between the chamber and the assay site; a fluid hole for connecting the channel; and a valve for opening and closing the fluid hole, and wherein the bio memory disc further includes a plurality of slots provided along an outer circumference of the disc.

In the bio memory disc according to the present invention, the slots may be disposed along the circumference of the bio memory disc in various slot sizes or intervals, so that rotation, rotation angle, and rotation number of the bio memory disc can be detected.

In the bio memory disc according to the present invention, the slot may be an opening or an optical reflector.

According to another aspect of the present invention, there is provided a bio memory disc comprising a lab-on-a-chip process system is further disposed on the disc, wherein the lab-on-a-chip process system includes: a sample inlet; a chamber for containing a buffer solution or a reaction solution; an assay site where bio materials are fixed on a substrate; a channel through which a fluid flows between the chamber and the assay site; a fluid hole for connecting the channel; and a valve for opening and closing the fluid hole, and wherein the bio memory disc further comprises an ABS (auto balancing system) chamber for containing a liquid material and/or steel balls so as to compensate for warbling generated due to an eccentricity of the bio memory disc during rotation of the bio memory disc and the ABS chamber is donut-shaped and disposed along the circumference of the bio memory disc.

In the bio memory disc according to the present invention, the ABS chamber may be used as a trash chamber.

According to another aspect of the present invention, there is provided a bio memory disc comprising a lab-on-a-chip process system is further disposed on the disc, wherein the lab-on-a-chip process system includes: a sample inlet; chambers for containing a buffer solution or a reaction solution; an assay site where bio materials are fixed on a substrate; a channel through which a fluid flows between the chamber and the assay site; a fluid hole for connecting the channel; and a valve for opening and closing the fluid hole, wherein one of the chamber is a preparation chamber connected to the sample inlet, wherein the bio memory disc further includes a excess chamber which is connected through a fixed quantity channel to the preparation chamber, and wherein, an excessively injected blood or sample of the preparation chamber is transferred to the excess chamber, so that a fixed quantity of the blood or the sample can be contained in the preparation chamber.

In the bio memory disc according to the present invention, the preparation chamber may further include a gauge or a level indicating means for informing an operator of a minimum amount of the injected sample or blood.

In the bio memory disc according to the present invention, the gauge or the level indicating means may be a fixed quantity indicating line drawn on the preparation chamber.

In the bio memory disc according to the present invention, the fixed quantity indicating line may be a black line drawn on the preparation chamber.

In the bio memory disc according to the present invention, an excessive quantity of sample over the fixed quantity indicating line may be transferred to the excess chamber during the rotation of the bio memory disc.

In the bio memory disc according to the present invention, the excess chamber may allow a level of a fixed quantity channel to match the fixed quantity indicating line, so that the excessive quantity of sample over the fixed quantity indicating line can be transferred to the excess chamber through the fixed quantity channel.

In the bio memory disc according to the present invention, the preparation chamber may be a Z-shaped chamber.

According to another aspect of the present invention, there is provided a bio memory disc comprising a lab-on-a-chip process system is further disposed on the disc, wherein the lab-on-a-chip process system includes: a sample inlet; a chamber for containing a buffer solution or a reaction solution; an assay site where bio materials are fixed on a substrate; a channel through which a fluid flows between the chamber and the assay site; a fluid hole for connecting the channel; and a valve for opening and closing the fluid hole, wherein the valve is constructed with a micro bead disposed at the fluid hole, a thin-film permanent magnet disposed over the micro bead, and a movable permanent magnet disposed under the micro bead, wherein a valve heater is further provided along the circumference of the fluid hole, so that a surface tension between the micro bead and the fluid hole during the opening of the valve can be removed by heat or air expansion due to the heat.

In the bio memory disc according to the present invention, the valve heater may include a coil or a resistor buried in the circumference of the fluid hole to generate heat by flowing a current through the coil or the resistor.

In the bio memory disc according to the present invention, the valve heater may generate heat by irradiating the circumference of the fluid hole with a laser beam.

In the bio memory disc according to the present invention, the valve heater may include a laser array buried in the circumference of the fluid hole to generate heat by turning on the laser array.

According to another aspect of the present invention, there is provided a bio memory disc comprising a lab-on-a-chip process system is further disposed on the disc, wherein the lab-on-a-chip process system includes: a sample inlet; chambers for containing a buffer solution or a reaction solution; an assay site where bio materials are fixed on a substrate; a channel through which a fluid flows between the chamber and the assay site; a fluid hole for connecting the channel; and a valve for opening and closing the fluid hole, wherein the bio memory disc further includes a dehumidification chamber or an humidity sensing chamber.

In the bio memory disc according to the present invention, the dehumidification chamber may contain a dehumidifying agent for removing the humidity, and the dehumidification chamber may be provided with an air hole.

In the bio memory disc according to the present invention, the humidity sensing chamber may include a humidity indicating card for detecting whether or not the bio memory disc is previously exposed to humidity or immersed in a liquid.

In the bio memory disc according to the present invention, the channel, the valve, and the chamber may be disposed and connected in a spiral shape so that the fluid can be easily transferred to a neighbor chamber through the fluid hole due to the centrifugal force generated by the rotation of the bio memory disc when the valve is opened.

In the bio memory disc according to the present invention, the bio memory disc may be constructed with an upper disc member, an intermediate disc member, and an lower disc member, wherein a plurality of the channels, a plurality of the chambers, and a plurality of the fluid holes are disposed on the only the intermediate disc member, and wherein the upper and lower disc members are integrally attached on an upper and lower surface of the intermediate disc member, respectively.

In the bio memory disc according to the present invention, the upper and lower disc members may be thin film sheets.

Preferably, the upper and lower disc members may have a thickness of 0.1 mm~0.6 mm, and the intermediate disc member may have a thickness of 0.6 mm~1.2 mm. The bio memory disc may have a diameter of 8 cm, 12 cm, or 32 mm.

In the bio memory disc according to the present invention, the assay site may be read out by using an optical measurement unit, an image sensor unit, an electro-chemical measurement unit, an impedance measuring unit, a bio pit detecting unit, a fluorescence detecting unit, a radioactivity detecting unit, an SPR (surface plasmon resonance) detecting unit, or an QCM (quartz crystal microbalance) detecting unit.

In the bio memory disc according to the present invention, the assay sites may be disposed in an array along the circumference of the bio memory disc.

In the bio memory disc according to the present invention, the chambers may be disposed in parallel in different sectors so as to perform single-item assay for multiple-type samples, multiple-item assay for a single-type sample, or multiple-item assay for multiple-type samples.

In the bio memory disc according to the present invention, the bio material may be one or more selected from DNA, oligonucleotide, RNA, PNA, ligand, receptor, antigen, antibody, protein, and a bio material. The bio material has a function of a capture probe for specific binding with a sample.

In the bio memory disc according to the present invention, the bio material may be one of multiple types of tumor markers.

In the bio memory disc according to the present invention, the tumor marker may be one or more selected from AFP, PSA, CEA, CA19-9, CA125, and CA15-3.

In the bio memory disc according to the present invention, the assay site may further include an air hole used to dry an inner portion of the assay site to remove moisture during the rotation of the bio memory disc.

In the bio memory disc according to the present invention, the chamber may further include a chamber exhaust hole, a chamber inlet, a chamber hole, or an ABS injecting hole.

In the bio memory disc according to the present invention, the chamber inlet and the chamber exhaust hole may be disposed at the center of the chamber.

In the bio memory disc according to the present invention, the chamber may include a chamber hole constructed by integrating the chamber inlet and the chamber exhaust hole.

In the bio memory disc according to the present invention, the chamber hole may be disposed at the center of the chamber, and a height of the chamber around the chamber hole may be larger than a height of the chamber hole.

In the bio memory disc according to the present invention, the chamber inlet, the chamber exhaust hole, the chamber hole, or the ABS injecting hole may be closed by using a sticker, a CD label sheet, a UV adhesive.

In the bio memory disc according to the present invention, the chamber exhaust hole may be closed by attaching a steel ball with an adhesive means having a adhesive force, and the chamber exhaust hole may be opened by detaching the steel ball from the adhesive means due to a centrifugal force during the rotation of the bio memory disc.

In the bio memory disc according to the present invention, the adhesive means may be a cushioned double-sided tape or a cushioned rubber-coated member.

In the bio memory disc according to the present invention, the steel ball may have a shape of a triangular cone and a cap so that a lower portion of the steel ball is enlarged.

In the bio memory disc according to the present invention, the adhesive means may be constructed by coating the chamber exhaust hole with a cushioned rubber material or by coating the steel ball with a cushioned rubber material.

In the bio memory disc according to the present invention, an upper surface of the bio memory disc may be subject to offset printing, silk screen printing, sticker printing, or CD label printing.

In the bio memory disc according to the present invention, portions corresponding to the preparation chamber or the assay site may be transparently printed or exposed in the offset printing, the silk screen printing, the sticker printing, or the CD label printing.

In the bio memory disc according to the present invention, the chamber may further include a mixer chamber for mixing liquid materials in the chamber.

In the bio memory disc according to the present invention, the Mixer chamber may include: magnetic micro beads which are inserted or contained in the mixer chamber; and a magnet which is disposed at an upper or lower portion of the Mixer chamber to exert an attractive force on the magnetic micro bead, wherein a speedy motion of the magnet induces a motion of the magnetic micro beads in the mixer chamber, so that the liquid material can be mixed.

In the bio memory disc according to the present invention, the Mixer chamber may include: magnetic micro beads which are inserted or contained in the mixer chamber; and a magnet which is disposed at an upper or lower portion of the Mixer chamber to exert an attractive force on the magnetic micro bead, wherein, in a state that the magnet is not moved, a rotation of the bio memory disc or a repetition of forward and inverse rotations of the bio memory disc induces a motion of the magnetic micro beads in the mixer chamber due to an attractive force of the magnet, so that the liquid material can be mixed.

In the bio memory disc according to the present invention, the liquid material may be mixed by alternately rotating the bio memory disc clockwise and counterclockwise.

In the bio memory disc according to the present invention, the liquid material may be mixed by alternately rotating and stopping the bio memory disc.

In the bio memory disc according to the present invention, the chamber may comprise: at least one preparation chamber for preparing a serum (plasma) sample or a antigen sample; at least one buffer chamber for temporarily storing or diluting the serum (plasma) sample or the antigen sample with a diluting solution; at least one Ag-Ab reaction chamber having capture probes for an Ag-Ab reaction with the prepared antigen sample which are fixed in an array on a substrate; and/or at least one trash chamber for collecting sludge generated in a washing process.

In the bio memory disc according to the present invention, the chamber may comprise: at least one preparation chamber for preparing a DNA sample; at least one DNA amplification chamber for amplifying the prepared DNA sample or performing polymer chain reaction (PCR) amplification thereof; at least one buffer chamber for temporarily storing or diluting the DNA sample with a diluting solution; at least one hybridization chamber having assay-diagnosis capture probes for hybridization reaction with the DNA sample which are fixed in an array on a substrate; and/or at least one trash chamber for collecting sludge generated in a washing process.

In the bio memory disc according to the present invention, the chamber may be integrated with a heating means or a laser generating unit for heating the chamber so as to adjust on-off of DNA sample amplification or enzyme mechanism in the chamber.

In the bio memory disc according to the present invention, the DNA amplification chamber further may include a cooling wind hole for supplying to the DNA amplification chamber a wind generated on a surface of the bio memory disc during the rotation of the bio memory disc in a rotation cooling period.

In the bio memory disc according to the present invention, the chamber may further include a washing chamber for storing a washing solution used for a washing process.

In the bio memory disc according to the present invention, the chamber may further include a conjugate chamber for a liquid conjugate solution.

In the bio memory disc according to the present invention, the conjugate solution stored in the conjugate chamber may include a mixture of multiple types of conjugates which have a specific binding with multiple types of samples for multi-isotope analysis.

In the bio memory disc according to the present invention, the buffer chamber may store label particles which are bound with a serum (plasma) sample, a antigen sample, or a DNA sample to constitute a complex.

In the bio memory disc according to the present invention, the label particle may be a gold particle, a latex particle, a coloring particle, a fluorescent particle, a enzyme (or an enzyme linked antibody), or an radioactive isotope particle.

In the bio memory disc according to the present invention, the conjugate solution may be formed by coupling coloring particles, fluorescent particle, or radioactive isotope particles.

In the bio memory disc according to the present invention, the coloring particle may be a gold particle, a latex particle, or an enzyme In the bio memory disc according to the present invention, the label particles of the buffer chamber may be a liquid conjugate solution coupled with the coloring particles.

In the bio memory disc according to the present invention, the substrate of the assay site may have a porous surface.

In the bio memory disc according to the present invention, the substrate of the assay site may be has a surface having a large surface area obtained by using a surface treatment means for enlarging a surface area.

In the bio memory disc according to the present invention, the surface treatment means may be a surface coating means.

In the bio memory disc according to the present invention, the surface having a large surface area may be a surface having micro prominences and micro depressions.

In the bio memory disc according to the present invention, the fluid is transferred between the chambers by using one method selected from a capillary channel method, a hydrophilic-coated channel method, a fluid pumping method, and an air thermal expansion method using a pump heater.

In the bio memory disc according to the present invention, the pump heater illuminates a rear portion of a sample with a laser beam to generate heat so that the sample moves in the forward direction due to air expansion of the rear portion of the sample.

In the bio memory disc according to the present invention, the fluid transferring performed by the fluid pumping method is a fluid transferring by using "pumping fluid movement" or vibration of a piezo device.

In the bio memory disc according to the present invention, the fluid transfer can be performed by a "pumping fluid movement" that a movable permanent magnet under the disc repeatedly performs rapid approaching and separating movements with respect to the center of the hole, with the rotation of the disc stopped. For example, repetition of the rapid approaching and separating movements of the permanent magnet on the slider with respect to the center of the hole causes up and down movements of the film-like cylindrical magnet. Due to the up and down movements of the film-like cylindrical magnet, a pumping force is generated and exerted on the fluid, so that the fluid can flow. The fluid movement by the pumping force is called a "pumping fluid movement".

The pumping method using the piezo device is well known in the art, for example U.S. Pat. No. 4,939,405 titled as "Piezo-electric vibrator pump".

In the bio memory disc according to the present invention, the sample inlet is covered with a thin inlet cover, and wherein a syringe needle penetrates the inlet cover, so that the blood or the sample is injected into the preparation chamber through the syringe needle.

In the bio memory disc according to the present invention, the inlet cover is made of vinyl.

In the bio memory disc according to the present invention, the sample inlet is constructed with at least one capillary tube or a bundle thereof.

In the bio memory disc according to the present invention, the capillary tube is emptied by transferring the blood or the sample in the capillary tube to the preparation chamber due to the centrifugal force during the rotation of the bio memory disc.

In the bio memory disc according to the present invention, a sample inlet indicator is printed on an upper surface of the inlet cover by using offset printing, silk screen printing, sticker printing, or CD label printing.

In the bio memory disc according to the present invention, the sample inlet indicator includes a sample inlet circumferential circle and a sample inlet central point.

In the bio memory disc according to the present invention, the preparation chamber contains antithrombin.

In the bio memory disc according to the present invention, valve is constructed with a micro bead disposed at the fluid hole, a thin-film permanent magnet disposed over the micro bead, and a movable permanent magnet disposed under the micro bead.

In the bio memory disc according to the present invention, the movable permanent magnet is mounted on a slider which is disposed under the bio memory disc to move in the radial direction, and wherein the movable permanent magnet is controlled by a slider motor changing a position of the slider.

In the bio memory disc according to the present invention, the fluid hole of the valve is closed by an attractive force between the micro bead and a thin-film permanent magnet disposed over the micro bead, and wherein the fluid hole of the valve is opened by a stronger attractive force between the micro bead and a movable permanent magnet disposed under the micro bead.

In the bio memory disc according to the present invention, the micro bead is a thin-film cylindrical magnet or a magnetic ball.

In the bio memory disc according to the present invention, the micro bead is coated with a cushioned rubber such as a silicon rubber.

In the bio memory disc according to the present invention, a surface of the fluid hole is coated with a cushioned rubber such as a silicon rubber.

In the bio memory disc according to the present invention, the thin-film permanent magnet disposed over the micro bead is attached and fixed on an upper portion of the upper disc member.

In the bio memory disc according to the present invention, all the valves of the bio memory disc are closed by attractive forces between the micro beads and the thin-film permanent magnets disposed over the micro beads during a longtime delivery or storage period or a unused period.

In the bio memory disc according to the present invention, a magnetic material is used as a substitute for the thin-film permanent magnet disposed over the micro bead.

In the bio memory disc according to the present invention, a barcode pattern indicating product ID (identification) of the bio memory disc is constructed with a sequence of the optical reflectors or a sequence of openings or slots.

In the bio memory disc according to the present invention, a valve dedicated to control a flow rate of an influx of the trash chamber is not provided, and a chamber gap in the trash chamber is changed in order to prevent a backward flow.

In the bio memory disc according to the present invention, the change of the chamber gap in the trash chamber is obtained by combining at least one large chamber gap portion and at least one small chamber gap portion in the trash chamber.

The bio memory disc according to the present invention may further comprise a reference hole used for alignment of the bio memory disc at the time of manufacturing and assembling the bio memory disc.

In the bio memory disc according to the present invention, the assay site is integrated with a thin-film fluorescence detecting unit.

In the bio memory disc according to the present invention, the thin-film fluorescence detecting unit is integrated by stacking a substrate layer, a waveguide layer, a metal film, and a fluorescence sensor layer.

In the bio memory disc according to the present invention, the substrate layer includes an anchored capture probe for performing specific binding with a fluorescence-labeled bio material.

In the bio memory disc according to the present invention, the substrate layer includes a n×m array of anchored multiple-type capture probes.

In the bio memory disc according to the present invention, elements of the n×m array of the substrate layer are individually addressed and read out through a sequential excitation of fluorescence labels of the elements by scanning of a laser beam generated from an excitation laser unit and through sensing of a fluorescence intensity generated from each of the excited fluorescence labels by a fluorescence sensor layer.

In the bio memory disc according to the present invention, the fluorescence sensor layer of the thin-film fluorescence detecting unit is constructed with a photo sensor for sensing light intensity. The thin-film fluorescence detecting unit may further comprise a buffer layer.

In the bio memory disc according to the present invention, at least one selected from the substrate layer, the waveguide layer, the metal film, and the fluorescence sensor layer of the thin-film fluorescence detecting unit is formed in a corrugated shape.

The corrugated shaped layers have a function of collecting fluorescences emitted from the fluorescence-labeled bio material in a direction, so that can detect a small amount of fluorescence.

In the bio memory disc according to the present invention, the assay site is a n×m array of the thin-film fluorescence detecting units.

In the bio memory disc according to the present invention, elements of the n×m array of the thin-film fluorescence detecting unit are individually addressed and read out through a sequential excitation of fluorescence labels of the elements by scanning of a laser beam generated from an excitation laser unit and through sensing of a fluorescence intensity generated from each of the excited fluorescence labels by a fluorescence sensor layer.

In the bio memory disc according to the present invention, the substrate layer of the thin-film fluorescence detecting unit is a porous membrane.

In the bio memory disc according to the present invention, the assay site is integrated with QCM (quartz crystal microbalance) detecting unit.

The technology for detecting a specific binding between two different bio molecules using the QCM detecting unit is well known in the art, for example U.S. Pat. No. 4,735,906 titled as "sensor having piezoelectric crystal for microgravimetric immunoassays".

In the bio memory disc according to the present invention, the QCM detecting unit is constructed with a quartz member and overlapped electrodes which are is disposed to face each other with the quartz member interposed therebetween.

In the bio memory disc according to the present invention, the QCM detecting unit is constructed with a crystalline silicon and overlapped electrodes which are is disposed to face each other with the crystalline silicon member interposed therebetween by using a semiconductor manufacturing process.

In the bio memory disc according to the present invention, the assay site is searched based on a difference between a resonance frequency measured before a reaction and a resonance frequency measured after the reaction and the dehydrating or drying of the assay site due to a high speed rotation of the bio memory disc.

In the bio memory disc according to the present invention, the overlapped electrodes of the QCM detecting unit are disposed in a shape of inter-digit.

In the bio memory disc according to the present invention, the assay site is read out by using an SPR (surface plasmon resonance) detecting unit including a light source an a optic system.

The SPR detecting unit is well known for detecting a specific binding of a capture probe by measuring a change of thickness or refractive index of an assay site in the art, for example U.S. Pat. No. 4,844,613 titled as "Optical surface plasmon sensor device".

In the bio memory disc according to the present invention, the substrate layer of the assay site is constructed by coating a gold film on a surface of a grating or a micro prism.

In the bio memory disc according to the present invention, the substrate layer of the assay site is constructed with a groove pattern coated with gold on a surface of the bio memory disc.

In the bio memory disc according to the present invention, the SPR detecting unit performs scanning in a predetermined range of incident angle $\theta_{in}$ at every time of starting reading out of the assay site to determine an optimal incident angle $\theta_{opt}$ where a contrast of light intensity between references spots of the assay site is maximized and, after introducing of the sample to the assay site, photographs a change in the light intensity of a 2-D array of the assay site with a CCD or CMOS camera to obtained a real-time SPR image.

In the bio memory disc according to the present invention, the SPR detecting unit performs scanning in a predetermined range of incident angle $\theta_{in}$ at every time of starting reading out of the assay site to fix the incident angle $\theta_{in}$ as an optimal incident angle $\theta_{opt}$ where a contrast of light intensity between references spots of the assay site is maximized and obtains an SPR image intensity difference by comparing an after-reaction SPR image photographed after introducing of the sample to the assay site with a before-reaction SPR image.

In the bio memory disc according to the present invention, the SPR detecting unit performs scanning in a predetermined range of incident angle $\theta_{in}$ at every time of starting reading out of the assay site to fix the incident angle $\theta_{in}$ as an optimal incident angle $\theta_{opt}$ where a contrast of light intensity between references spots of the assay site is maximized and obtains a time-varying SPR image intensity difference by comparing an after-reaction SPR image photographed in a predetermined time interval after introducing of the sample to the assay site with a before-reaction SPR image.

In the bio memory disc according to the present invention, the SPR detecting unit performs scanning in a predetermined range of incident angle $\theta_{in}$ at every time of starting reading out of the assay site to determine an optimal incident angle $\theta_{opt}$ where a contrast of light intensity between references spots of the assay site is maximized and, after introducing of the sample to the assay site, measures a sensorgram of each element of an array of the assay site.

In the bio memory disc according to the present invention, the SPR detecting unit repeats a scanning operation in a predetermined range ($\theta_{min} \leq \theta_{opt} \leq \theta_{max}$) of incident angle $\theta_{in}$ in a predetermined time interval after introducing of the sample to the assay site to measure a time-varying SPR angle or a time-varying SPR angle shift of each element of the array of the assay site.

In the bio memory disc according to the present invention, a data including an SPR image intensity difference, a sensorgram, an SPR angle, and an SPR angle shift measured in a predetermined time interval by the SPR detecting unit is reconstructed by using curve fitting or interpolation.

In the bio memory disc according to the present invention, an incident angle $\theta_{in}$ scanning operation of the SPR detecting unit is performed by precision rotation of the bio memory disc, radial movement of a slider with the bio memory disc stopped, azimuthal movement of the slider, forward, backward, leftward, and rightward movements of a light source, or tilt adjustment of the light source.

In the bio memory disc according to the present invention, the precision rotation of the bio memory disc for the incident angle $\theta_{in}$ scanning operation is performed by a slot determining means or an FG signal determining means.

In the bio memory disc according to the present invention, the radial or azimuthal movement of the slider for the incident angle $\theta_{in}$ scanning operation is performed by moving the slider on which the light source is mounted.

In the bio memory disc according to the present invention, the forward, backward, leftward, and rightward movements of the light source or the tilt adjustment of the light source is performed by controlling an electromagnet coupled with the light source which is mounted on the slider.

In the bio memory disc according to the present invention, the forward, backward, leftward, and rightward movements of the light source or the tilt adjustment of the light source is performed by controlling a shape memory alloy coupled with the light source which is mounted on the slider.

In the bio memory disc according to the present invention, the forward, backward, leftward, and rightward movements of the light source or the tilt adjustment of the light source is performed by controlling a piezo device coupled with the light source which is mounted on the slider.

In the bio memory disc according to the present invention, the light source is constructed with at least one LED or laser diode.

In the bio memory disc according to the present invention, the light source and the optic system is mounted on the slider.

In the bio memory disc according to the present invention, the optic system further comprises: a reference photo sensor for sensing an intensity $I_r$ of a reference light from the light source; an SPR photo sensor for sensing an intensity $I_s$ of a reflected light of the assay site; and a driving circuit for obtaining a ratio of signals of the two sensors and outputting an SPR sensing signal.

In the bio memory disc according to the present invention, the optic system further comprises: a collimator for obtaining a parallel light from a light of the light source; a lens used for detecting a reflected light of the assay site; a polarizing beam splitter for extracting an S-polarization component and a P-polarization component; two SPR photo sensors for sensing the two polarization components; and a driving circuit for obtaining a ratio of signals of the two sensors and outputting an SPR sensing signal.

In the bio memory disc according to the present invention, the assay site is searched based on a difference between an SPR sensing signal measured before a reaction and an SPR sensing signal measured after the reaction and the dehydrating or drying of the assay site due to a high speed rotation of the bio memory disc.

In the bio memory disc according to the present invention, the substrate of the Ag-Ab reaction chamber or the hybridization chamber is constructed with a strip or a porous membrane.

In the bio memory disc according to the present invention, the strip further comprises absorbent pads at both ends thereof.

In the bio memory disc according to the present invention, the strip further comprises a conjugate pad and absorbent pad at both ends thereof.

In the bio memory disc according to the present invention, the conjugate pad is formed by attaching a conjugate solution in a dried form on the conjugate pad.

In the bio memory disc according to the present invention, the conjugate is coupled with a coloring particle, a fluorescent particle, or a radioactive isotope particle.

In the bio memory disc according to the present invention, the coloring particle is gold, a latex particle, or an enzyme In the bio memory disc according to the present invention, the conjugates of the conjugate pad are coupled with the plasma sample, the antigen sample, the DNA sample prepared from the preparation chamber to constitute a complex, and after that, forms a specific binding with the capture probes on the assay site.

In the bio memory disc according to the present invention, the substrate layer of the assay site is constructed in a spotted array or a multi-lined form where a plurality of the capture probes having a specific binding with a complex are spotted or aligned.

In the bio memory disc according to the present invention, the strip further comprises a conjugate pad and a absorbent pad at both end thereof and a sample pad or a pre-filtration pad.

In the bio memory disc according to the present invention, the substrate layer of the assay site is constructed with at least one test line, at least one reference line, and at least one control line, with at least one test spot, at least one reference spot, and at least one control spot, or with at least one test spot, at least one reference line, and at least one control line.

In the bio memory disc according to the present invention, the reference line or the reference spot is obtained by setting a strength of the binding reaction to the sample to be close to a cutoff value in order to easily determine negative or positive reactivity.

In the bio memory disc according to the present invention, the number of the reference lines or the number of the reference spots is set to be two or more in order to easily determine negative or positive reactivity by using interpolation and, after that, the strengths of the binding reaction are set.

In the bio memory disc according to the present invention, the strength of the specific binding reaction between the capture probe and the complex is obtained based on a fluorescence intensity of a fluorescent particle, a color intensity of a coloring particle, a radioactivity intensity, a change of an electrical signal in an electro-chemical reaction, a shift of an SPR angle, an SPR image intensity difference, or a change $\Delta f$ in a resonance frequency of a QCM detecting unit.

In the bio memory disc according to the present invention, the determination of the negative or positive reactivity is performed based on a difference of a strength of the specific binding reaction between a test line and a reference line, a difference of a strength of the specific binding reaction between a test spot and a reference spot, or a difference of a strength of the specific binding reaction between the test spot and the reference line.

In the bio memory disc according to the present invention, a result of reaction in the assay site is observed with an unaided eye or an aided eye through an aperture on an upper (front) or lower (rear) surface of the bio memory disc.

In the bio memory disc according to the present invention, a quantitative analysis or a qualitative analysis of a result of the Ag-Ab reaction is performed by adjusting an introducing time of the Ag-Ab reaction and a time interval of the washing process or the drying process for the Ag-Ab reaction chamber.

In the bio memory disc according to the present invention, a quantitative analysis or a qualitative analysis of a result of the hybridization reaction is performed by adjusting an introducing time of the hybridization reaction and a time interval of the washing process or the drying process for the hybridization reaction chamber.

In the bio memory disc according to the present invention, the bio memory disc is used as a cartridge type bio memory disc contained in a cartridge.

In the bio memory disc according to the present invention, the cartridge-type bio memory disc further includes a central cap disposed at a disc aperture to be easily engaged and mounted on a turntable.

In the bio memory disc according to the present invention, the cartridge-type bio memory disc further includes: a cartridge grip; and a hole which a prominence disposed on the tray of the bio memory disc drive apparatus is to be inserted into.

In the bio memory disc according to the present invention, the cartridge-type bio memory disc is assembled by interposing the bio memory disc having the central cap between upper and lower covers of a cartridge and pressing the upper and lower covers.

In the bio memory disc according to the present invention, a central aperture for exposing the sample inlet indicator is formed at the center of the upper cover.

In the bio memory disc according to the present invention, the lower cover includes an opening.

In the bio memory disc according to the present invention, the cartridge grip is printed with a barcode pattern indicating product ID.

In the bio memory disc according to the present invention, the upper cover of the cartridge is a transparent cover.

In the bio memory disc according to the present invention, the bio memory disc is coupled with a necklace or a wristlet.

In the bio memory disc according to the present invention, the bio memory disc is received in a necklace-type cartridge or a wristlet-type cartridge.

In the bio memory disc according to the present invention, the necklace-type cartridge or the wristlet-type cartridge is provided with a portion of receiving a solar cell or a battery for supplying power to the bio memory disc.

According to another aspect of the present invention, there is provided a bio memory disc drive apparatus comprising: the bio memory disc according to the present invention; a spindle motor for rotating the bio memory disc; a slider on which a movable permanent magnet and at least one detecting unit for reading out the assay site are mounted, wherein the detecting unit is selected from an optical measurement unit, a image sensor unit, a electro-chemical measurement unit, a impedance measuring unit, a bio pit detecting unit, a fluorescence detecting unit, a radioactivity detecting unit, a SPR detecting unit, and a QCM (quartz crystal microbalance); a slider motor for controlling movement of the slider; a central controller for controlling the aforementioned components; and a body for supporting the bio memory disc drive apparatus.

In the bio memory disc drive apparatus according to the present invention, the slider is provided with a bio optical pickup module including a detecting unit for reading the assay site, a movable permanent magnet, and an optical pickup device including a CD reader or a DVD reader.

In the bio memory disc drive apparatus according to the present invention, the central controller performs: (i) controlling a spindle motor to rotate or stop the bio memory disc; (ii) controlling the slider motor to move a detecting unit disposed on the slider; (iii) controlling opening and closing of the valve of the bio memory disc to move the movable permanent magnet; and (iv) determining which of an optical disc including a CD, a CD-R, a game CD, and a DVD and a bio memory disc is currently loaded on the bio memory disc drive apparatus; wherein, (v) if the optical disc is loaded on the bio memory disc drive apparatus, the central controller performs operations of the optical disc including transmitting contents read out by using the optical pickup device from the optical disc to a storage unit or an input/output unit, transmitting a to-be-written content to the optical pickup device, or transmitting read/write control signals to components, wherein (vi) if the bio disc is loaded on the bio memory disc drive apparatus, the central controller performs operations for controlling the lab-on-a-chip process, and wherein (vii) if the memory disc is loaded on the bio memory disc drive apparatus, the central controller performs controlling reading of contents stored in the semiconductor memory or writing of contents in the semiconductor memory.

In the bio memory disc drive apparatus according to the present invention, the optical pickup device or the bio optical pickup module reads out a groove pattern, a data pattern, or a barcode pattern at a specific position of the bio memory disc to allow the central controller to determine which of a bio disc, a memory disc, and an optical disc is currently loaded on the bio memory disc drive apparatus.

In the bio memory disc drive apparatus according to the present invention, further comprising a memory IC card slot used for inserting the memory IC card into the bio memory disc drive apparatus.

In the bio memory disc drive apparatus according to the present invention, the memory IC card stores personal encryption information or a reaction result and history of the assay site.

In the bio memory disc drive apparatus according to the present invention, personal encryption verification is completed by inserting the memory IC card into the memory IC card inserting slot, so that operations of the bio memory disc drive apparatus are enabled.

According to another aspect of the present invention, there is provided a bio memory disc drive apparatus comprising: a memory disc according to the present invention; a detaching/attaching means and a mounting means for loading the memory disc; a optical communication unit for providing an optical interface with a memory optical conversion module on the memory disc; a memory disc controller for controlling the memory disc; and a body of the digital book which is designed to be a folding type.

In the bio memory disc drive apparatus according to the present invention, the digital book further includes a speaker and a microphone so as to convert and reproduce an audio content stored in the semiconductor memory or converts audio to a digital audio content and store the digital audio content in the semiconductor memory.

In the bio memory disc drive apparatus according to the present invention, the digital book further includes an image sensor so as to capture and store image contents in the semiconductor memory.

In the bio memory disc drive apparatus according to the present invention, the digital book further includes an LCD display unit so as to display image contents reproduced from the semiconductor memory.

In the bio memory disc drive apparatus according to the present invention, the digital book further includes a digital multimedia broadcast receiver, a TV/radio receiver, or a mobile-phone transceiver in a body of the digital book so as to perform a digital multimedia broadcast function, a TV/radio receiving function, a mobile-phone transceiving function, or an electric calculating function.

In the bio memory disc drive apparatus according to the present invention, the digital book further includes a mirror.

In the bio memory disc drive apparatus according to the present invention, the digital book further includes an IR receiver.

In the bio memory disc drive apparatus according to the present invention, the digital book further includes a key pad associated with a digital book function.

In the bio memory disc drive apparatus according to the present invention, a key pad of the digital book includes at least one selected from a play button, a record button, a search button, a forward button, a reverse button, a stop button, a pause button, a power button, a conversation button, a conversation stop button, a menu button, a ten-key button, a camera on button, a TV on/off button, a TV channel up/down button, a volume up/down button, a recording button, and a keyboard button.

In the bio memory disc drive apparatus according to the present invention, the digital book further includes a plurality of semiconductor memories in the body of the digital book.

In the bio memory disc drive apparatus according to the present invention, the key pad of the digital book further includes a multi-functional button including a jog shuttle button and four directional arrow buttons.

In the bio memory disc drive apparatus according to the present invention, further comprising a disc input/output unit which provides an interface for uploading contents of the memory disc 100b to an external digital information storage device (for example, a PC) or a display apparatus (for example, a TV or a LCD monitor) or downloading digital information from the external digital information storage device or the display apparatus.

In the bio memory disc drive apparatus according to the present invention, a reference prominence which is engaged with a reference hole of the memory disc to perform optical alignment between the optical communication unit and the memory optical conversion module at the time of top loading of the memory disc is provided to the detaching/attaching means and the mounting means.

In the bio memory disc drive apparatus according to the present invention, the content of the memory disc is reproduced, edited, or stored by using the button of the digital book.

In the bio memory disc drive apparatus according to the present invention, the bio memory disc drive apparatus according to the present invention is included in the body of the digital book, so that the bio disc is top-loaded on the detaching/attaching means to perform a nucleic acid hybridization assay function, an immuno-assay function, or a remote diagnosis function.

In the bio memory disc drive apparatus according to the present invention, the image sensor unit further includes a reflecting mirror for illuminating the assay site, so that a reflected image is captured by an image sensor.

In the bio memory disc drive apparatus according to the present invention, the image sensor unit further includes at least one LED (light emitting diode) for illumination.

In the bio memory disc drive apparatus according to the present invention, an assay site searching process for optical alignment between the image sensor unit and the assay site is performed before the image sensor unit captures an image of the assay site.

In the bio memory disc drive apparatus according to the present invention, a permanent magnet used for the optical alignment is provided on the bio memory disc.

In the bio memory disc drive apparatus according to the present invention, further comprising a slot detecting means or an FG signal determining means.

In the bio memory disc drive apparatus according to the present invention, the slot detecting means is constructed by using light reflected from an optical reflector or light transmitted through an opening.

In the bio memory disc drive apparatus according to the present invention, the slot detecting means using the reflected light is constructed with the optical reflector and a transmitting member and a receiving member of an optical pickup device.

In the bio memory disc drive apparatus according to the present invention, the slot detecting means reads out a barcode pattern indicating product ID of the bio memory disc by using the reflected light.

In the bio memory disc drive apparatus according to the present invention, the rotation, the rotation angle, and the rotation number of the bio memory disc is detected by the slot detecting means and the FG signal determining means so that a azimuthal direction valve searching operation, a memory optical conversion module searching process, or an assay site searching process is performed.

The FG signal is well illustrated in the data sheet of Mitsubishi semiconductor M63022FP (Spindle motor and 5ch actuator driver). The FG signal is a pulse signal synchronized in a Hall sensor of a spindle motor. The FG signal determining means can detect the rotation, the rotation angle, and the rotation number of the bio memory disc by measuring and analyzing the number of pulse in the central controller. Therefore, the slot detecting means and the FG signal determining means can increase the accuracy and speed of the azimuthal azimuthal direction valve searching operation.

In the bio memory disc drive apparatus according to the present invention, a difference of strengths of the binding reaction of the assay sites is obtained by analyzing image information captured by an image sensor unit.

In the bio memory disc drive apparatus according to the present invention, the central controller enhances the image information of a reference line (or a reference spot) and a test line (or a test spot) captured by the image sensor unit to calculate a value of the difference of the strength of the binding reaction and displays the value or a grade-designated result on a display apparatus or the enhanced image information on the display apparatus.

In the bio memory disc drive apparatus according to the present invention, the central controller enhances image information of a reference line (or reference spot) and a test line (or test spot) captured by the image sensor unit to calculate a value of the difference between the strength of the binding reaction, and remotely transmits the value, a grade-designated result, or the enhanced image information.

In the bio memory disc drive apparatus according to the present invention, the image information of the reference line (or the reference spot) and the test line (or the test spot) is enhanced by adjusting darkness, lightness, or contrast.

In the bio memory disc drive apparatus according to the present invention, further comprising a light source including a glow lamp for supplying light to a solar cell on the bio memory disc.

In the bio memory disc drive apparatus according to the present invention, further comprising a wireless power supply unit for actuating an induction coil on the bio memory disc to generate and store a sufficient electricity in a condenser on the bio memory disc.

In the bio memory disc drive apparatus according to the present invention, further comprising a light source including a glow lamp, a laser generating unit, or a heating means used for adjusting DNA amplification or enzyme mechanism in the chamber.

In the bio memory disc drive apparatus according to the present invention, a rotation cooling operation where the bio memory disc is rotated at a high speed to cool the chamber of the bio memory disc is performed so as to adjust DNA amplification of the enzyme mechanism.

In the bio memory disc drive apparatus according to the present invention, further comprising a non-contact interface for allowing the bio memory disc drive apparatus to receive a result of reading out the assay site using an electro-chemical detecting unit, an impedance measuring unit, a fluorescence detecting unit, a radioactivity detecting unit, an SPR detecting unit, and a QCM detecting unit or contents of the semiconductor memory.

In the bio memory disc drive apparatus according to the present invention, the non-contact interface is an optical interface between the optical communication unit on the bio memory disc drive apparatus and the memory optical conversion module on the bio memory disc.

In the bio memory disc drive apparatus according to the present invention, the optical communication unit is constructed with an optical pickup device of the bio memory disc drive apparatus.

In the bio memory disc drive apparatus according to the present invention, further comprising an optical pickup device for reading out an optical disc including an audio CD, a CD-R, a game CD, and a DVD.

In the bio memory disc drive apparatus according to the present invention, further comprising:
an optical pickup device for reading out an optical disc (for example: an audio CD, a CD-R, a game CD, and a DVD); and
a bio optical pickup module including an optical communication unit for providing an optical interface to a memory optical conversion module on the bio memory disc.

In the bio memory disc drive apparatus according to the present invention, the bio optical pickup module further includes a laser generating unit, an excitation laser unit, a slot detecting means, or an image sensor unit.

In the bio memory disc drive apparatus according to the present invention, the image sensor unit reads out a barcode pattern indicating product ID of the bio memory disc.

In the bio memory disc drive apparatus according to the present invention, the bio optical pickup module and the movable permanent magnet are disposed on the slider so that positions thereof are controlled by controlling the slider motor.

In the bio memory disc drive apparatus according to the present invention, further comprising an input/output unit for providing a result of reading the assay site to an external computer through a remote communication network or receiving a control command from the computer.

In the bio memory disc drive apparatus according to the present invention, the input/output unit has a USB (universal serial bus) communication protocol, an IEEE 1394 communication protocol, an ATAPI communication protocol, an SCSI communication protocol, or an Internet communication protocol.

In the bio memory disc drive apparatus according to the present invention, the bio memory disc drive apparatus is interfaced with a PC through a SCSI communication protocol input/output unit.

In the bio memory disc drive apparatus according to the present invention, a memory optical conversion module searching process for optical alignment between the optical communication unit and the memory optical conversion module is performed before a time of reading contents of the semiconductor memory or writing digital information in the semiconductor memory.

In the bio memory disc drive apparatus according to the present invention, a permanent magnet used for the optical alignment between the optical communication unit and the memory optical conversion module is disposed on the bio memory disc.

In the bio memory disc drive apparatus according to c the present invention, at the time of reading the semiconductor memory, the optical communication unit operates as an optical receiver and the memory optical conversion module operates as an optical transmitter, and wherein, at the time of writing the digital information in the semiconductor memory, the optical communication unit operates as an optical receiver and the memory optical conversion module operates as an optical transmitter.

In the bio memory disc drive apparatus according to the present invention, the bio optical pickup module including the excitation laser unit performs a 2-D laser scanning operation on the assay site by repeating radial movement of the slider and rotation of the bio memory disc in an assay site reading process so that 2-D read information of a 2-D array of the assay site is obtained by the detecting unit.

In the bio memory disc drive apparatus according to the present invention, elements of an array of the assay sites are spatially addressed by the excitation laser unit during the rotation of the bio memory disc, wherein the strengths of the binding reaction are read out by the detecting units corresponding to the elements, and wherein a result of the reading is converted into an optical signal by the memory optical conversion module and transmitted to the optical communication unit.

In the bio memory disc drive apparatus according to the present invention, elements of an array of the assay sites are excited by semiconductor lasers which are integrated on the bio memory disc so as to correspond to the elements, wherein electrical signals proportional to the strengths of the binding reaction are detected by the detecting units corresponding to the elements and transmitted to the memory optical conversion module, and wherein the memory optical conversion module converts the electrical signals to optical signals and transmits a result of the reading of the assay sites to an optical communication unit.

In the bio memory disc drive apparatus according to the present invention, the image sensor unit captures an image of the humidity sensing chamber stores the captured image of the humidity sensing chamber in a storage unit.

In the bio memory disc drive apparatus according to the present invention, the central controller analyzes the image of the humidity sensing chamber, and wherein, if the bio memory disc is determined to be exposed to humidity, the central controller (i) informs a user of the fact, (ii) records the fact as a history management item together with time information and production ID of the bio memory disc in a storage unit, or (iii) transmits the fact to an after-service center for the bio memory disc through the input/output unit.

In the bio memory disc drive apparatus according to the present invention, the body for supporting the bio memory disc drive apparatus allows the bio memory disc to be top-loaded, front-loaded, side-loaded, or back-loaded.

In the bio memory disc drive apparatus according to the present invention, the bio memory disc drive apparatus is assembled with a main body of a personal computer.

In the bio memory disc drive apparatus according to the present invention, further comprising a display unit which displays an operating state of the bio memory disc drive apparatus, a type of loaded disc that is an optical disc, a bio disc, or a memory disc, and a result of reading or diagnosis of the bio memory disc.

In the bio memory disc drive apparatus according to the present invention, the display unit is a LCD monitor, a LCD TV, or an LED display apparatus.

In the bio memory disc drive apparatus according to the present invention, the main body of the personal computer provides a user with a GUI (graphic user interface) corresponding to the type of loaded disc that is an optical disc, a bio disc, or a memory disc.

In the bio memory disc drive apparatus according to the present invention, the body of the bio memory disc drive apparatus is integrated with a plurality of the bio memory disc drive apparatuses for loading a plurality of the bio memory discs simultaneously.

In the bio memory disc drive apparatus according to the present invention, the bio memory disc drive apparatus integrated with a plurality of the bio memory disc drive apparatuses further comprises an input/output port for providing an interface with a computer or an external apparatus for controlling a plurality of the bio memory disc drive apparatuses.

In the bio memory disc drive apparatus according to the present invention, the input/output port has a USB (universal serial bus) communication protocol, an IEEE 1394 communication protocol, an ATAPI communication protocol, or an Internet communication protocol.

In the bio memory disc drive apparatus according to the present invention, the body of the bio memory disc drive apparatus is constructed in a double-deck-type where two decks are provided with the bio memory disc drive apparatuses or a combo type.

In the bio memory disc drive apparatus according to the present invention, the bio memory disc drive apparatus is integrated with a TV including an LCD TV, a PDP TV, and a CRT TV.

In the bio memory disc drive apparatus according to the present invention, the TV is provided with an Internet input/output port so that a result of the reading or diagnosis of the bio memory disc performed by the bio memory disc drive apparatus is transmitted to a doctor so as to perform a remote diagnosis.

In the bio memory disc drive apparatus according to the present invention, the TV displays an operating state of the bio memory disc drive apparatus, a type of loaded disc that is an optical disc, a bio disc, or a memory disc, and a result of reading or diagnosis of the bio memory disc.

In the bio memory disc drive apparatus according to the present invention, the TV provides a user with an GUI (graphic user interface) corresponding to the type of loaded disc that is an optical disc, a bio disc, or a memory disc.

In the bio memory disc drive apparatus according to the present invention, the TV is controlled by using a remote controller so as to provide a user with an GUI (graphic user interface) corresponding to the type of loaded disc that is an optical disc, a bio disc, or a memory disc.

In the bio memory disc drive apparatus according to the present invention, the TV further comprises a messenger which periodically informing a user of a time of periodic test or diagnosis through an e-mail or a window on a screen of the TV so as to easily perform follow-up management.

In the bio memory disc drive apparatus according to the present invention, the bio memory disc drive apparatus mounted on the main body of the personal computer has a function as an HDD (hard disc drive) which reads data stored in the semiconductor memory on the bio memory disc, transmits the data to the main body of the personal computer, receives the data from the main body of the personal computer, and stores the data in the semiconductor memory on the bio memory disc.

According to another aspect of the present invention, there is provided an assay method using the bio memory disc drive apparatus according to the present invention, comprising steps of: loading the bio memory disc on the bio memory disc drive apparatus; reading out the product ID of the bio memory disc; driving the bio memory disc according to a control protocol corresponding to the read product ID; assaying the assay site by using position information and array information of the assay site according to the product ID if the read product ID is of a bio disc; displaying a result of diagnosis and assay of the assay site.

In the assay method according to the present invention, further comprising a step of analyzing an image of the assay site obtained after the reaction of the capture probe and the sample, performing determination of a negative or positive reactivity, presence of potential risk group, or a value thereof according to the strength of the binding reaction, and outputting a result of the analysis.

In the assay method according to the present invention, further comprising steps of: if the read product ID is a bio memory disc, reading a digital data stored in the semiconductor memory on the bio memory disc according to the control protocol corresponding to the read product ID to reproduce the digital data; transmitting the reproduced digital data to the bio memory disc drive apparatus through an optical interface between the memory optical conversion module and the optical communication unit; and outputting the transmitted digital data to an audio apparatus, a display apparatus including an LCD TV, a PDP TV, and a CRT TV, or other storage media.

In the assay method according to the present invention, further comprising steps of: if the read product ID is a bio memory disc, reading a digital data from the semiconductor memory on the bio memory disc or writing a digital data in the semiconductor memory according to the control protocol corresponding to the read product ID; transmitting the read digital data to the bio memory disc drive apparatus through an optical interface between the memory optical conversion module and the optical communication unit; and transmitting the to-be-written digital data to the semiconductor memory through the optical interface between the memory optical conversion module and the optical communication unit.

In the assay method according to the present invention, further comprising a step of: if an optical disc including CD and DVD is loaded on the bio memory disc drive apparatus, reproducing or reading the optical disc by using the optical pickup device.

In the assay method according to the present invention, further comprising a messenger step of periodically informing a user of a time of periodic test or diagnosis through an e-mail, a telephone, or a window on a monitor of the personal computer, or a mobile phone so as to easily perform follow-up management.

In the assay method according to the present invention, further comprising a visiting service step, wherein a bio memory disc associated person periodically visits a user of the bio memory disc to inform the user of a time of periodic test or diagnosis or to provide a diagnostic or medical advice so as to easily perform follow-up management.

In the assay method according to the present invention, wherein the visiting service step comprises a service step of taking away or collecting a used bio memory disc.

According to another aspect of the present invention, there is provided an assay method using the bio memory disc drive apparatus according to the present invention, comprising: a preparation step of preparing a DNA sample from blood, a cell, or an RNA; a DNA amplification step of amplifying the prepared DNA sample; a hybridization step of performing a hybridization reaction of a DNA obtained by the DNA amplification with capture probes arrayed on the assay site (hybridization chamber); and an assay site reading step of reading the assay site by using an optical measurement unit, an electro-chemical measurement unit, an impedance measuring unit, an image sensor unit, a bio pit detecting unit, a fluorescence detecting unit, a radioactivity detecting unit, a QCM detecting unit, or an SPR detecting unit.

According to another aspect of the present invention, there is provided an assay method using the bio memory disc drive apparatus according to the present invention, comprising steps of: separating a DNA or an RNA from blood or a cell; amplifying the DNA; performing a hybridization reaction of the DNA in a hybridization chamber; and transferring a washing solution to the hybridization chamber and washing the hybridization chamber with the washing solution.

In the assay method according to the present invention, in the separating of the DNA or the RNA, after a chemical process using a lysis buffer, the bio memory disc is rotated at a high speed, so that the DNA or the RNA is separated from the sample by using centrifugal separation.

In the assay method according to the present invention, further comprising a labeling step of labeling the DNA with a label.

In the assay method according to the present invention, further comprising a step of reading a result of the reaction in the hybridization chamber, converting the result of reaction into an optical signal in a memory optical conversion module, and transmitting the optical signal to an optical communication unit.

In the assay method according to the present invention, in the DNA amplification step, the DNA is amplified by heating and cooling the bio memory disc through a high speed rotation or repeating the heating and cooling.

According to the another aspect of the present invention, there is provided an assay method using the bio memory disc drive apparatus according to the present invention, comprising steps of: separating serum (plasma) or antigen from through a centrifugal separation by rotating the bio memory disc at a high speed; transferring the antigen to an assay site (a Ag-Ab reaction chamber); performing incubation so as to activate an Ag-Ab reaction of the antigen with a capture probe (an immuno probe); transferring a washing solution to the assay chamber and washing the assay chamber with the washing solution.

According to the another aspect of the present invention, there is provided an assay method using the bio memory disc drive apparatus according to the present invention, comprising steps of: separating serum (plasma) or antigen from through a centrifugal separation by rotating the bio memory disc at a high speed; reacting the antigen with a label and performing incubation so as to form a label-Ag complex; transferring the label-Ag complex to an assay site (an Ag-Ab reaction chamber); performing incubation so as to activate an Ag-Ab reaction of the label-Ag complex with a capture probe (an immuno probe); and transferring a washing solution to the assay chamber and washing the assay chamber with the washing solution.

According to the another aspect of the present invention, there is provided an assay method using the bio memory disc drive apparatus according to the present invention, comprising steps of: transferring serum or plasma to a Ag-Ab reaction chamber (an assay site) and performing a an Ag-Ab reaction; and transferring a washing solution to the Ag-Ab reaction chamber and washing the Ag-Ab reaction chamber with the washing solution.

In the assay method according to the present invention, the serum or plasma is separated from a sample by rotating the bio memory disc at a high speed through centrifugal separation.

In the assay method according to the present invention, further comprising a step of transferring a conjugate solution to the Ag-Ab reaction chamber before or after the Ag-Ab reaction.

In the assay method according to the present invention, further comprising a step of reading a result of the Ag-Ab reaction in the assay site by using an optical measurement unit, an electro-chemical measurement unit, an impedance measuring unit, an image sensor unit, a bio pit detecting unit, a fluorescence detecting unit, a radioactivity detecting unit, a QCM detecting unit, or an SPR detecting unit.

In the assay method according to the present invention, further comprising a step of transferring a fluid through a channel coated with a hydrophilic material.

In the assay method according to the present invention, further comprising a step of drying the assay site through a centrifugal force by rotating the bio memory disc at a high speed.

In the assay method according to the present invention, further comprising a step of reading a result of the reaction in the Ag-Ab reaction chamber, converting the result of the reaction into an optical signal by a memory optical conversion module, and transmitting the optical signal to an optical communication unit.

In the assay method according to the present invention, further comprising a step of observing a result of the reaction in the Ag-Ab reaction chamber or the hybridization chamber with an unaided eye.

According to the another aspect of the present invention, there is provided an assay method using the bio memory disc drive apparatus according to the present invention, comprising steps of: sampling blood through a blood sampling tool by a user of the bio memory disc and injecting the blood into a preparation chamber through a sample inlet to store the blood in the preparation chamber; loading the bio memory disc on the bio memory disc drive apparatus and separating serum (or plasma) and blood clot from the blood in the preparation chamber by rotating the bio memory disc at a high speed through centrifugal separation; opening a valve to transfer the separated serum (or plasma) to a buffer chamber and diluting the serum (or plasma) with a diluting solution; stopping the bio memory disc and opening a valve to transfer a diluted serum (or plasma) stored in a buffer chamber through a V-shaped channel coated with a hydrophilic material; when the serum (or plasma) is transferred up to a sample pad of a strip, that is, a end of the V-shaped channel, dropping the plasma (or plasma) on the sample pad of the strip through fluid pumping transferring by using the valve; diffusing the dropped serum (or plasma) through capillary phenomenon due to porosity of the strip to specifically reacting the serum (or plasma) with the capture probe on the strip during the diffusion of the serum (or plasma); drying the strip by rotating the bio memory disc at a high speed; opening a valve to transfer a washing solution stored in a washing chamber through the V-shaped channel coated with the hydrophilic material; when the washing solution is transferred up to the sample pad of the strip, that is, the end of the V-shaped channel, dropping the washing solution on the sample pad of the strip through fluid pumping transferring by using the valve; diffusing the dropped washing solution through the capillary phenomenon due to the porosity of the strip to remove non-specifically reacted components from a surface of the strip during the diffusion of the washing solution; drying the strip by rotating the bio memory disc at a high speed; and reading a result of the reaction on the strip by using an optical measurement unit, an electro-chemical measurement unit, an impedance measuring unit, an image sensor unit, a bio pit detecting unit, a fluorescence detecting unit, a radioactivity detecting unit, a QCM detecting unit, or an SPR detecting unit.

In the assay method according to the present invention, further comprising steps of: displaying a diagnosis result according to the result of the reaction and a prescription on a computer monitor; automatically or manually connecting to a doctor through an Internet to remotely transmit the diagnosis result and a questionnaire sheet to the doctor; a patient waiting a prescription of the doctor.

BRIEF DESCRIPTION OF THE DRAWINGS

The above and other objects, features and other advantages of the present invention will be more clearly understood from the following detailed description taken in conjunction with the accompanying drawings, in which;

FIG. 10A is a view illustrating an embodiment of an outer appearance of a bio memory disc drive apparatus;

BEST MODE FOR CARRYING OUT THE INVENTION

Hereinafter, embodiments of the present invention are described in detail with reference to the accompanying drawings.

In the embodiment, a disc on which only the lab-on-a-chip process system is disposed is called a bio disc; a disc on which only the semiconductor memory is called a memory disc; and the bio disc and the memory disc are collectively called a bio memory disc.

In a valve for controlling a flow or flow rate of a fluid on the bio disc according to the present invention, a channel is opened and closed by using a micro bead which is disposed in a fluid hole of the bio disc, wherein the micro bead is moved by a force between a permanent magnet disposed at an upper portion of the bio disc and a movable permanent magnet disposed at a lower portion of the bio disc. The construction and operations of the valve are well disclosed in the aforementioned prior patent applications.

Figure 1A:
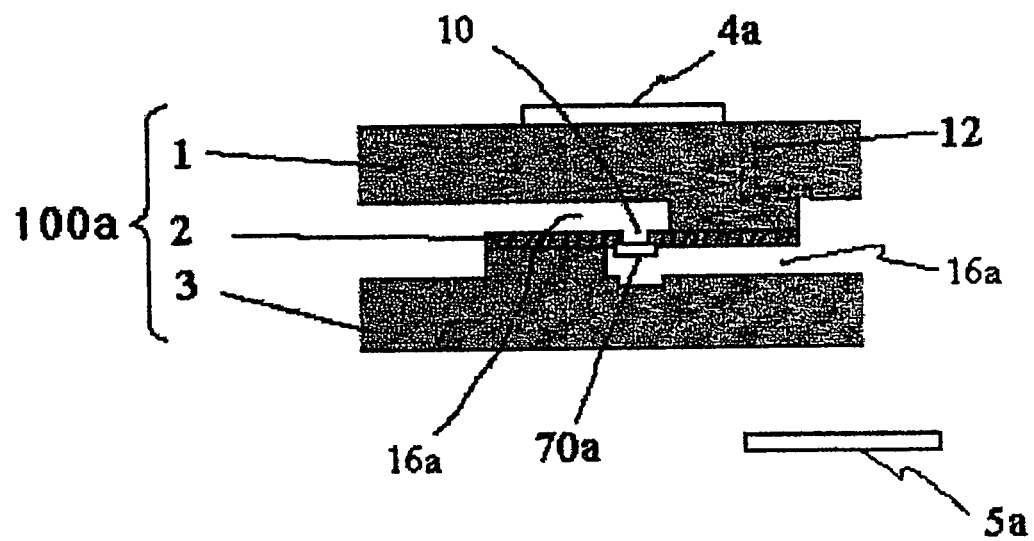
FIGS. 1A and 1B are cross-sectional views illustrating an embodiment of a bio disc having a thin-film valve device using a thin-film cylindrical magnet provided within a fluid hole.
Figure 1B:
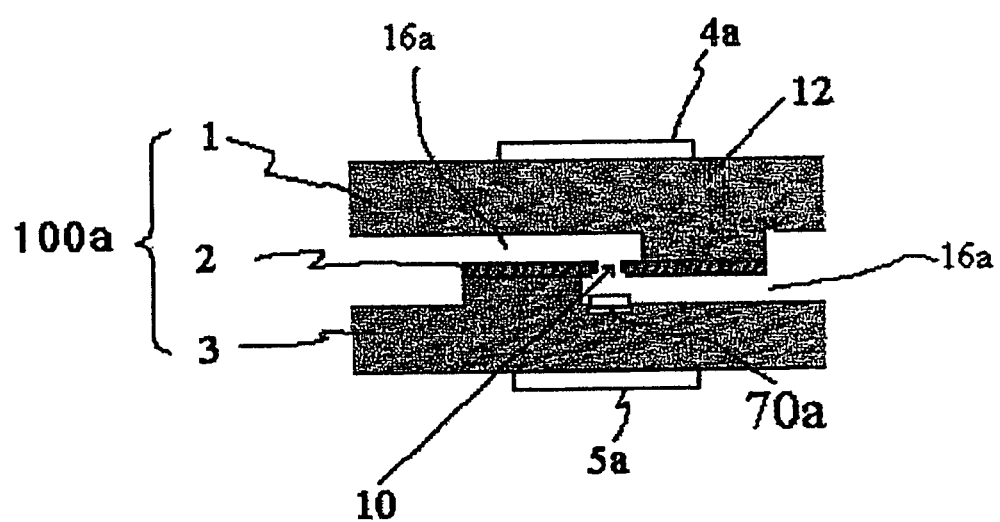

FIGS. 1A and 1B are cross-sectional views illustrating an embodiment of a bio disc 100a having a thin-film valve device using a thin-film cylindrical magnet 70a provided within a fluid hole 10.

The bio disc 100a includes an upper disc member 1, an intermediate disc member 2, and a lower disc member 3. In an injection pressing process for the members, a plurality of channels through a fluid can flow on a surface of the disc, a plurality of chambers for storing a buffer solution, and a plurality of fluid holes for connecting the channels are formed. The members are attached thereto to constitute one body of the bio disc 100a.

FIG. 1A illustrates a case where the fluid hole 10 is closed by a thin-film cylindrical magnet 70a so as to disconnect the channel 16a. FIG. 1B illustrates a case where the fluid hole 10 is opened so as to connect the channel 16a. As shown in FIG. 1A, in order to disconnect the channel 16a by closing the fluid hole 10, a movable permanent magnet 5a is firstly separated from a center of the fluid hole 10, and the thin-film cylindrical magnet 70a is pulled up due to an attractive force of an upper permanent magnet 4a, so that the fluid hole 10 is closed. In other words, the valve is closed by the attractive force between the upper permanent magnet 4a and the thin-film cylindrical magnet 70a. On the contrary, as shown in FIG. 1B, in order to connect the channel 16a by opening the fluid hole 10, the movable permanent magnet 5a is moved toward the center of the fluid hole 10, the thin-film cylindrical magnet 70a is pulled down due to an attractive force. In other words, the valve is opened by the attractive force between the movable permanent magnet 5a and the thin-film cylindrical magnet 70a that is larger than the attractive force between the upper permanent magnet 4a and the thin-film cylindrical magnet 70a. For the reason, the magnetic field of the movable permanent magnet 5a may be designed to be larger than that of the upper permanent magnet 4a.

In the present invention, the upper permanent magnet 4a may be fixed on the upper disc member 1, and the lower permanent magnet 5a may be a movable permanent magnet. In addition, in the present invention, an exhaust hole 12 may be disposed on the upper disc member 1, so that the fluid can flow through the channel 16a without pressure when the value is opened. In addition, the channel and the chamber may be disposed and connected in a spiral shape so that the fluid can be easily transferred to a neighbor chamber through the fluid hole 10 due to the centrifugal force generated by the rotation of the bio disc 100a when the valve is opened.

In the bio memory disc according to the embodiment, the upper permanent magnet 4a may be fixed on an upper portion of the upper disc member 1. Therefore, due to the attractive magnetic force between the thin-film cylindrical magnet 70a and the upper permanent magnet 4a, all the valves of the bio disc 100a can be always closed during a longtime delivery or storage period FIGS. 1C and 1D are cross-sectional views illustrating another embodiment of a bio disc 100a having a thin-film valve device using a micro bead 70a provided within a fluid hole 10.

The bio disc 100a includes an upper disc member 1, an intermediate disc member 2, and lower disc member 3. Unlike the bio disc shown in FIGS. 1A and 1B, a plurality of channels through the fluid can flow, a plurality of chambers for storing a buffer solution, and a plurality of fluid holes for connecting the channels are formed on only the intermediate disc member 2. The upper and lower disc members 1 and 3 are attached to the intermediate disc member 2 to constitute one body of the bio disc 100a. In this case, since the injection pressing process for forming the fluid holes, the channels, and the chambers are performed on only the intermediate disc member 2, it is possible to reduce production cost in comparison with the bio disc shown in FIGS. 1A and 1B. In addition, since any pressing process is not required for the upper and lower disc members 1 and 2, a thin sheet type of disc can be used. Therefore, it is possible to further reduce a thickness of the bio disc 100a.

Figure 1C:
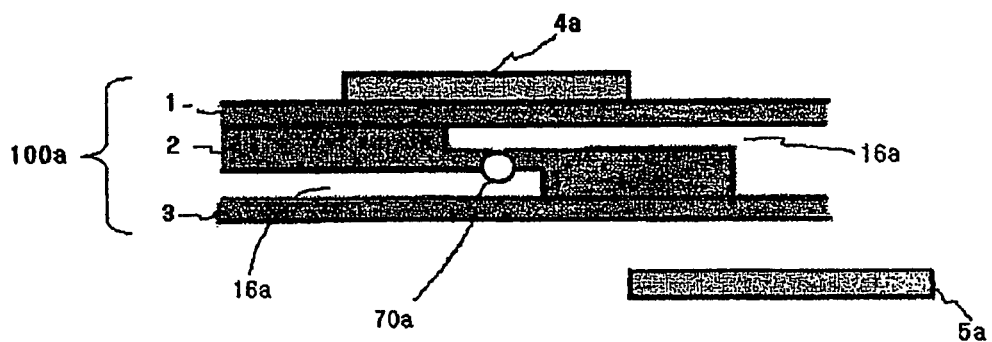
FIGS. 1C and 1D are cross-sectional views illustrating another embodiment of a bio disc having a thin-film valve device using a micro bead provided within a fluid hole.
Figure 1D:
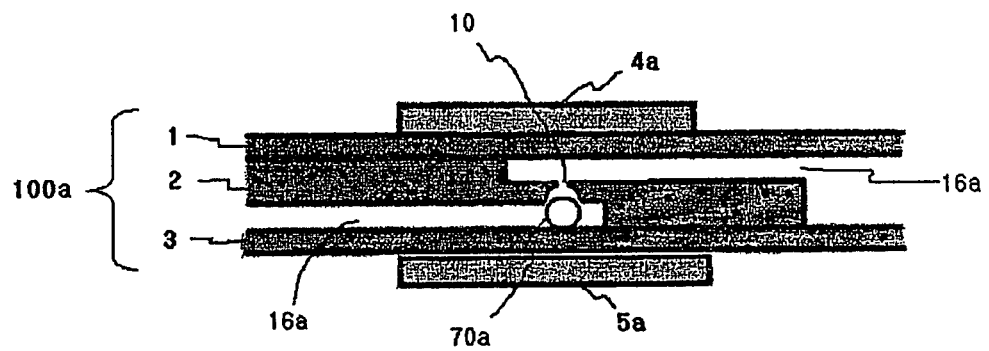

FIG. 1C illustrates a case where the fluid hole 10 is closed by a micro bead 70a so as to disconnect the channel 16a. FIG. 1D illustrates a case where the fluid hole 10 is opened so as to connect the channel 16a. Reference numeral 5a denotes a movable permanent magnet for controlling opening and closing of the micro bead 70a, and reference numeral 4a denotes an upper permanent magnet.

Figure 1E:
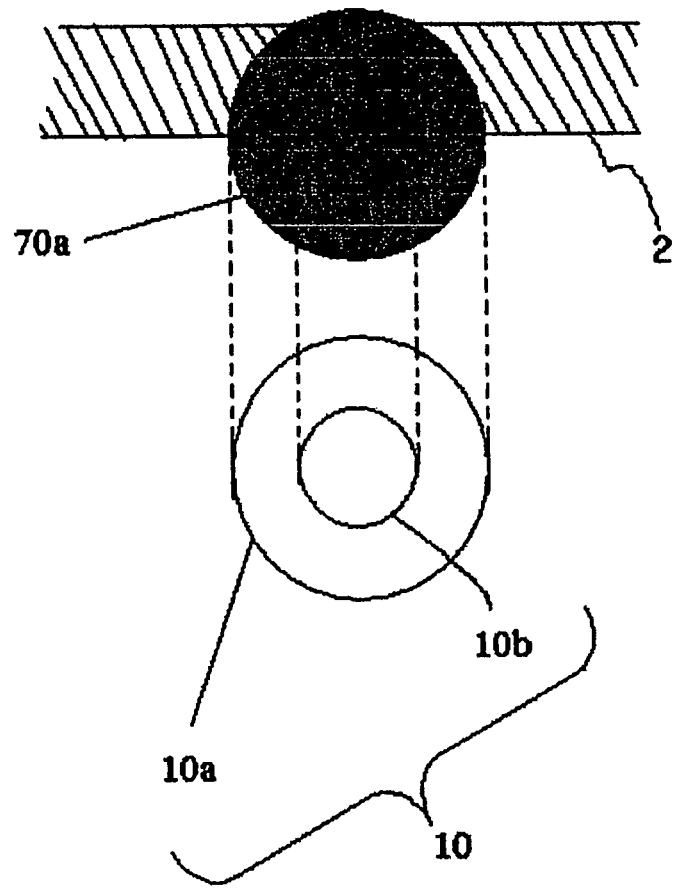
FIG. 1E is an enlarged partial cross-sectional view illustrating the fluid hole of the thin-film valve device using the micro bead in the above embodiment.

FIG. 1E is an enlarged partial cross-sectional view illustrating the fluid hole 10 of the thin-film valve device using the micro bead 70a. Reference numeral 10 denotes the fluid hole of the intermediate disc member 2 which contacts the micro bead 70a. The fluid hole 10 is designed to have a curvature corresponding to the micro bead 70a in order to prevent leakage of the fluid when the fluid hole 10 is closed.

Reference numerals 10a and 10b denote outer and inner apertures of the fluid hole 10, respectively. The curvature between the outer and inner apertures 10a and 10b is designed to match the curvature of the micro bead 70a. However, in this case, a force larger than the surface tension between the micro bead 70a and the fluid hole 10 is needed to draw out the micro bead 70a from the fluid hole 10 so as to open the fluid hole 10. The surface tension is generated between a fluid on the surface of the fluid hole 10 and the surface of the micro bead 70a. Due to the surface tension, the fluid hole 10 is hard to open. In particular, if the fluid is a viscous material, the fluid hole 10 is further hard to open.

Figure 1F:
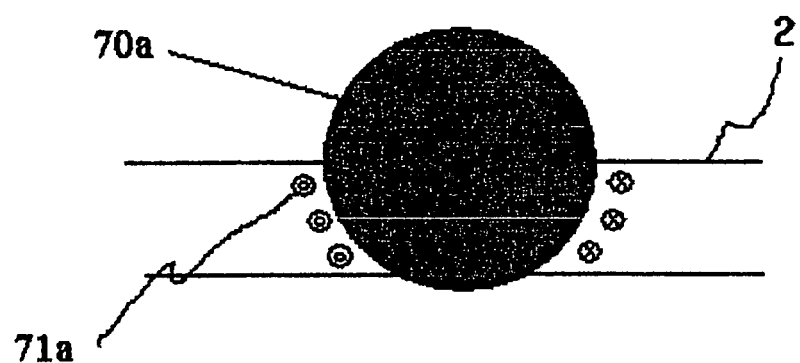
FIGS. 1F and 1G are cross-sectional views illustrating still another embodiment of a bio disc having a thin-film valve device using a micro bead provided within a fluid hole and a valve heater buried in an intermediate disc member, so that the valve heater can remove surface tension between the micro bead and a fluid to easily open the fluid hole.
Figure 1G:
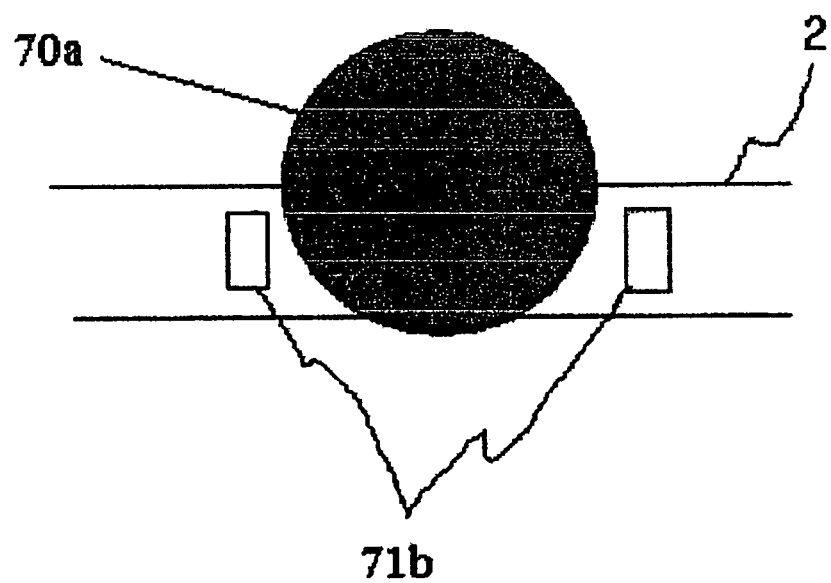

FIGS. 1F and 1G are cross-sectional views illustrating still another embodiment of a bio disc having a thin-film valve device using a micro bead provided within a fluid hole and a valve heater buried in the intermediate disc member 2, so that the valve heater can remove the surface tension between the micro bead 70a and the fluid to easily open the fluid hole 10.

FIG. 1F illustrates a case where a coil 71a is wound and buried along the circumference of the fluid hole 10 of the intermediate disc member 2. When a current flows through the coil 71a, heat is generated. Due to the heat, the surface tension is removed, so that the fluid hole 10 can be easily opened. More specifically, the heat generated around the fluid hole 10 expands air or the fluid so that the surface tension can be removed. Accordingly, the fluid hole 10 can be easily opened.

FIG. 1G illustrates a case where a laser array 71b is buried along the circumference of the fluid hole 10. When the laser array 71b is turned on, heat is generated. Due to the heat, the surface tension is removed, so that the fluid hole can be easily opened. The laser array is constructed by connecting a plurality of laser generating devices in parallel.

In the preferred embodiment of the present invention, the micro bead may be a thin-film cylindrical magnet or a magnetic ball which is coated with a cushioned rubber such as a silicon rubber.

In the preferred embodiment of the present invention, the upper permanent magnet may be constructed with a magnetic material.

In the present invention, instead of the coating of the cushioned rubber, a thin-film rubber may be inserted between the thin-film cylindrical magnet and the fluid hole.

The coating of the cushioned rubber or the inserting of the thin-film rubber is provided so as to prevent leakage of a fluid when the valve is closed.

Figure 2A:
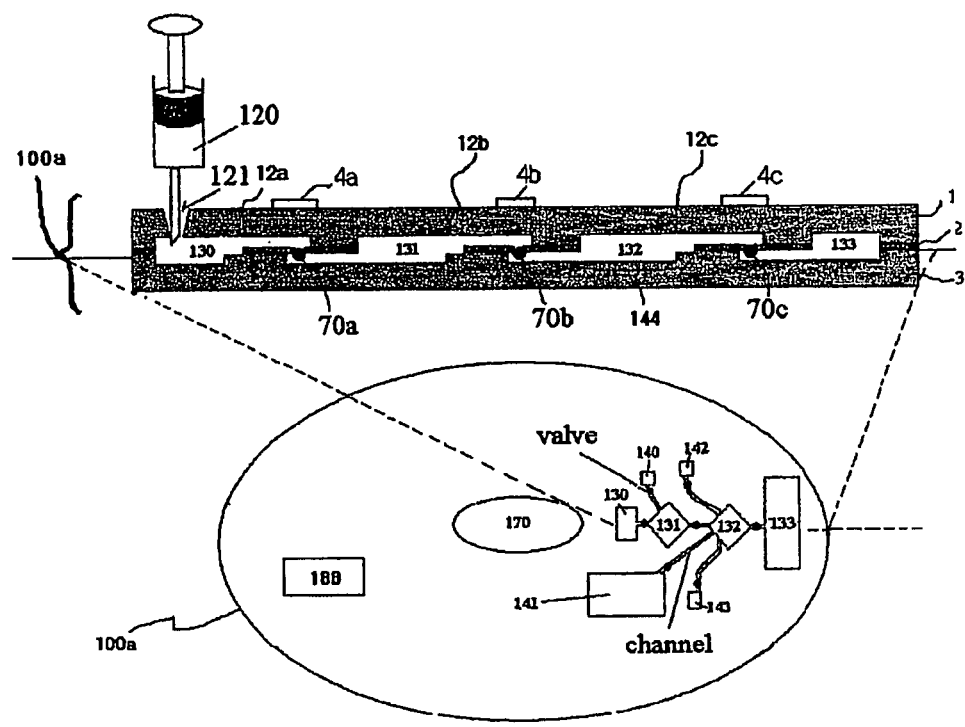
FIGS. 2A and 2B are views illustrating an embodiment of a bio disc in which a lab-on-a-chip process system is integrated and a bio memory disc drive apparatus which controls the bio disc.
Figure 2B:
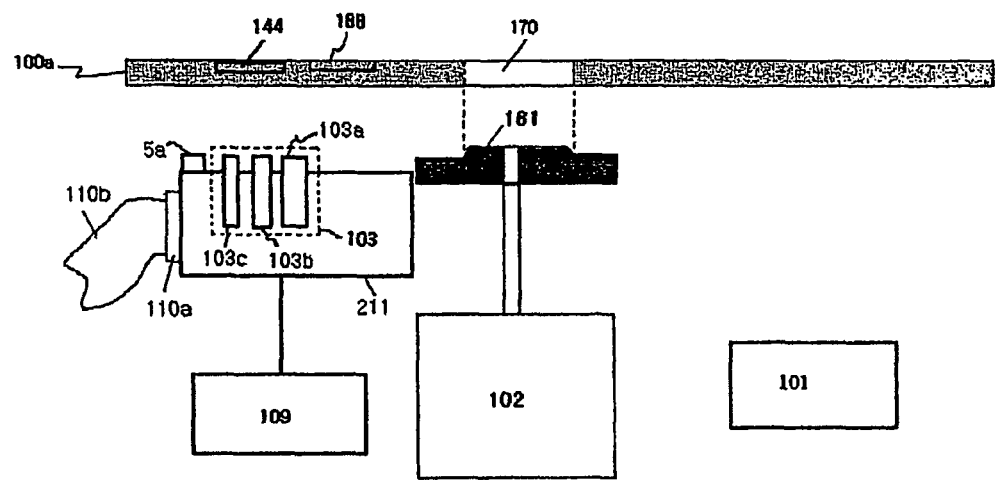

FIGS. 2A and 2B are views illustrating an embodiment of a bio disc in which a lab-on-a-chip process system is integrated and a bio memory disc drive apparatus which controls the bio disc. in the embodiment, the lab-on-a-chip process system includes chambers for storing various buffer solutions used for assay and performing various chemical reactions, channels for transferring the fluid and buffer solutions, and thin-film value devices for opening and closing the channels.

Reference numerals 12a, 12b, and 12c denote exhaust holes.

In the present invention, a body of the bio disc 100a may be made of plastic, PMMA, glass, mica, silica, silicon wafer, or others. In terms of flexibility and cost, the plastic and the silicon wafer are preferably used.

The micro beads 70a, 70b, and 70c are independently controlled by magnet fields between the upper permanent magnets 4a, 4b, and 4c the movable permanent magnet 5a, respectively. Reference numeral 120 denotes a pipette, a syringe, a lancet, or other sample injection means. Reference numeral 121 denotes a sample inlet. Reference numeral 170 denotes a disc central aperture. Reference numeral 130 denotes a preparation chamber where a preparation process for preparing a DNA sample from blood or a cell or preparing a DNA sample through reverse-transcription of RNA is performed. Reference numeral 131 denotes a DNA amplification chamber where a DNA amplification process is performed. Reference numeral 132 denotes a hybridization chamber where a hybridization process is performed. The hybridization chamber is an assay site where an array of capture probes for assay and diagnosis of the amplified DNA are attached on a substrate. Reference numeral 133 denotes a trash chamber for collecting sludge generated in the washing process. Reference numeral 211 denotes a slider on which the movable permanent magnet 5a and a BOPM 103 are mounted. The slider 211 is mechanically connected to a slider motor 109.

Reference numeral 140 denotes a chamber for storing a buffer solution including polymerazes, primers, and enzymes used for the DNA amplification process. Reference numerals 141, 142, and 143 denote chambers for storing enzymes used for the hybridization process. Reference numeral 144 denotes a fluorescence detecting unit.

At the starting or ending time of the processes (the preparation process, the DNA amplification process, the hybridization process, and the washing process), the valve is opened by moving the movable permanent magnet 5a disposed on the slider 211 toward the center of the fluid hole of the valve. The fluid can be transferred through a hydrophilic-coated channel due to a centrifugal force during the rotation of the bio disc. Since the fluid is a hydrophilic material, the fluid can be easily transferred through the narrow hydrophilic-coated channel due to the capillary phenomenon.

Reference numeral 103a denotes an optical pickup device for replaying a general optical disc such as CD and DVD, and reference numeral 103b denotes an optical communication unit. Reference numeral 103c denotes an excitation laser unit. The optical pickup device 103a, the optical communication unit 103b, and the excitation laser unit 103c are combined or integrated into a bio optical pickup module (BOPM) 103.

The excitation laser unit 103c excites a fluorescence-labeled confined signal element. At this time, the fluorescence detecting unit 144 obtains reading information of the assay site 132.

In the bio memory disc drive apparatus according to the embodiment, the BOPM 103 including the excitation laser unit 103c performs a 2-D laser scanning operation on the assay site 132 by repeating radial movement of the slider 211 and rotation of the bio disc 100a so that 2-D reading information of the two-dimensional array of the assay site 132 can be obtained by the fluorescence detecting unit 144.

Firstly, the slider 211 moves to locate the excitation laser unit 103c at the innermost position of the assay site. Next, in the state that the excitation laser unit 103c is turned on, the bio disc 100a is slowly rotated, and inner positions of the assay site are read out. Next, the excitation laser unit 103c is moved by ΔR outwards, and the entire assay site is read out. A series of the process is called an assay site reading process. The ΔR denotes a short distance in the radial direction.

Reference numeral 188 denotes a memory optical conversion module which converts the reading information on the assay site 133 detected by the fluorescence detecting unit 144 into an optical signal and transmits the optical signal to the optical communication unit 103b through an optical interface scheme.

Reference numeral 110b denotes a flexible cable for electrically connecting a central controller 101 to the BOPM 103 through a wafer or harness 11a to transmit control signals to the BOPM 103 on the slider 211.

Reference numeral 181 denotes a turntable on which the bio memory disc 100 is mounted. The central aperture 170 of the disc is engaged with the turntable 181 in a front, top, side, or back loading scheme.

Instead of the fluorescence detecting unit 144, an optical measurement unit, an electro-chemical detecting unit, an impedance measuring unit, a quartz crystal microbalance (QCM) unit, a surface plasmon resonance (SPR) unit, and a radioactivity detecting unit may be used to read out the assay site.

In the bio memory disc according to the embodiment, the memory optical conversion module 188 converts an electrical signal corresponding to the reading result of the assay site read by the optical measurement unit, the electro-chemical detecting unit, the impedance measuring unit, the QCM unit, the SPR unit, the fluorescence detecting unit, or the radioactivity detecting unit to an optical signal and transmits the optical signal to the optical communication unit 103b in wireless manner. Reference numeral 102 denotes a spindle motor for rotating the turntable 181.

Figure 2C:
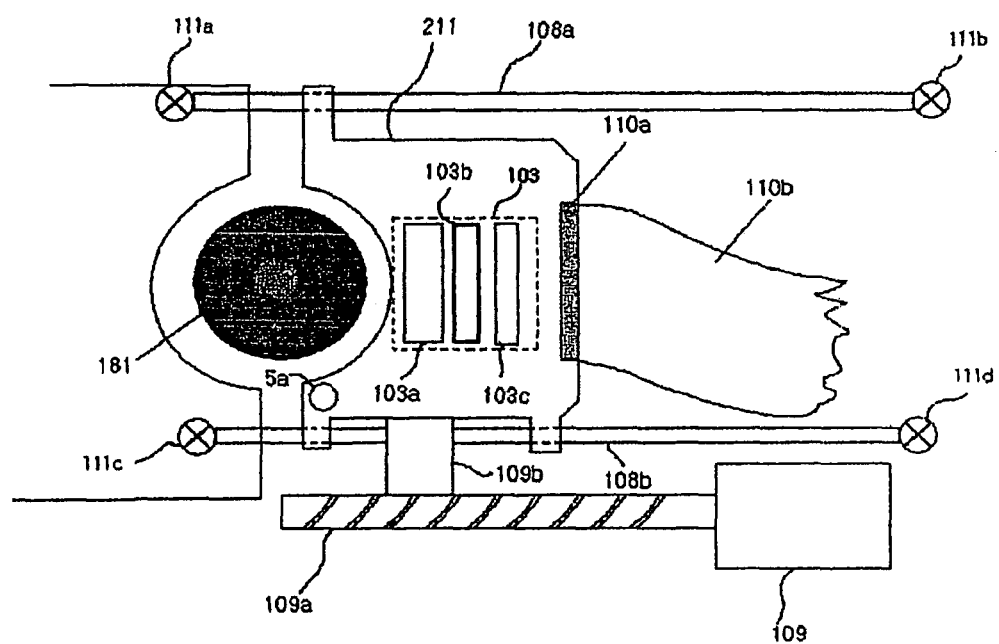
FIG. 2C is a plan view illustrating an embodiment of a slider on which a BOPM and a movable permanent magnet are disposed.

FIG. 2C is a plan view illustrating an embodiment of a slider 211 on which the BOPM 103 and the movable permanent magnet 5a are disposed;

The slider 211 is connected to worm gear connecting portions 109a and 109b connected to a shaft of the slider motor 109, so that the movement of the slider 211 can be controlled by the rotation of the slider motor 109.

The slider is slidingly moved by using the slide arms 108a and 108b as a guide. The slide arms 108a and 108b are engaged with a body of the bio memory drive apparatus by using screws 111a, 111b, 111c, and 111d. Reference numeral 110b denotes the flexible cable which is connected through the wafer or harness 110a. Reference numeral 181 denotes a turntable rotated by the spindle motor 102.

Figure 2D:
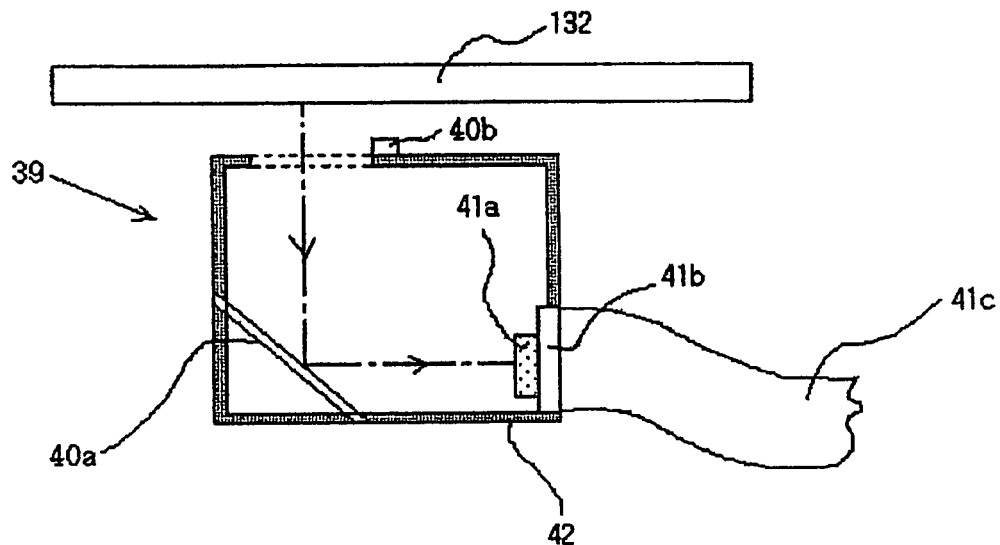
FIG. 2D is a cross-sectional view illustrating an image sensor unit for detecting an assay site.

FIG. 2D is a cross-sectional view illustrating an image sensor unit 39 for detecting an assay site 132.

Figure 2E:
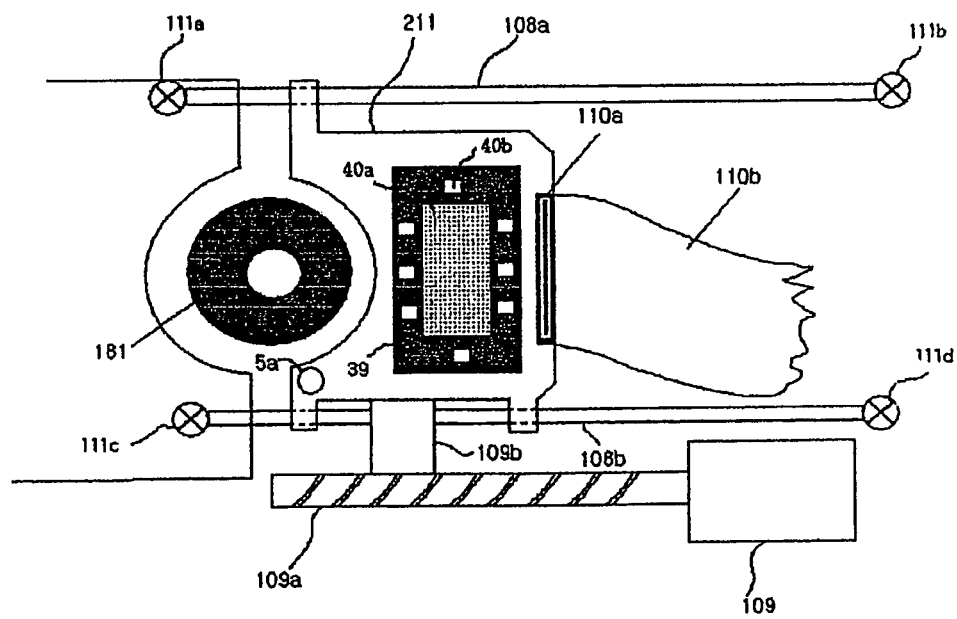
FIG. 2E is a plan view illustrating a slider on which the image sensor unit of FIG. 2D is disposed.

FIG. 2E is a plan view illustrating a slider on which the image sensor unit of FIG. 2D is disposed.

The image sensor 41a captures an image of the assay site 132 reflected by a reflecting mirror 40a which illuminates the image sensor 41a. Reference numeral 41b denotes an image processor for converting the captured image information to a digital signal and performing image processing thereof. The processed image information is transmitted through a flexible cable 41c to the central controller 101. Reference numeral 42 denotes a body for supporting the image sensor unit 39. Reference numeral 40b denotes at least one light emitting diode (LED) used for illumination of the image sensor.

The movable permanent magnet 5a is disposed on the slider 21.

In the bio memory disc according to the embodiment, the slider 211 together with the BOPM 103, the movable permanent magnet 5a, and the image sensor unit 39 are disposed.

In the bio memory disc drive apparatus according to the embodiment, the image sensor unit 39 performs an assay site searching process before capturing the image of the assay site 132.

In the bio memory disc drive apparatus according to the embodiment, a permanent magnet 75 is disposed on the bio memory disc in order to easily perform the optical alignment between the image sensor unit 39 and the assay site 132.

When the permanent magnet 75 meets the movable magnet 5a, the bio disc 100a is stopped due to the attractive force between the two magnets, so that the optical alignment between the image sensor unit 39 and the assay site 132 can be obtained. Accordingly, the assay site searching process is completed.

The assay site searching process is similar to the memory optical conversion module searching process using the optical alignment between the optical communication unit 103b and the memory optical conversion module 188. Therefore, detailed description thereof is omitted.

Figure 3A:
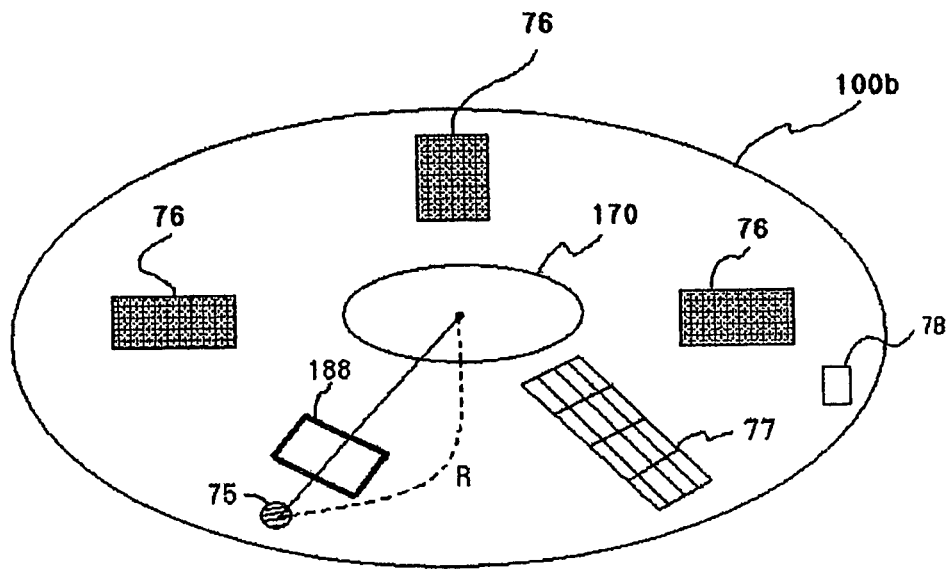
FIGS. 3A to 3C are schematic perspective views illustrating embodiments of a bio memory disc on which a plurality of semiconductor memories are integrated.
Figure 3B:
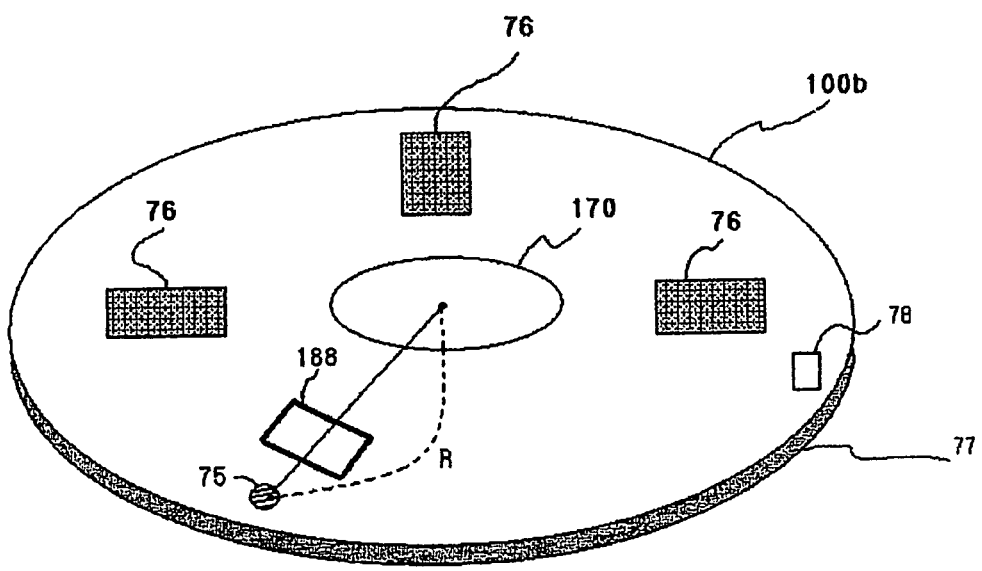
Figure 3C:
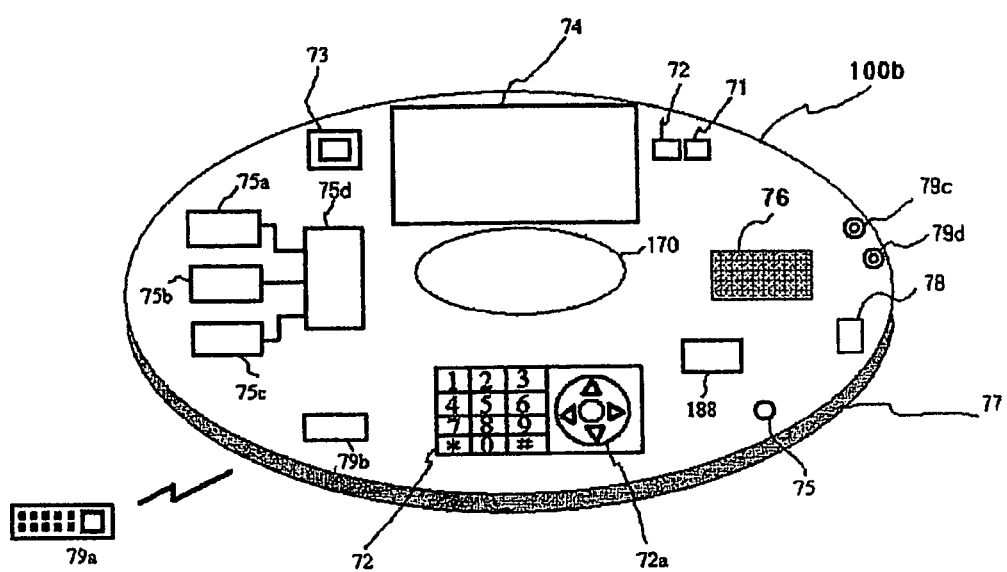

FIGS. 3A to 3C are schematic perspective views illustrating embodiments of a memory disc 100b on which a plurality of semiconductor memories 76 are integrated.

In the embodiment, the memory disc 100b is preferably constructed with a silicon wafer for the convenience of integration of the semiconductor memories.

Reference numeral 76 denotes a semiconductor memory. The digital information is converted to an optical signal by a memory optical conversion module 188 and transmitted to the optical communication unit 103.

The memory optical conversion module 188 receives the digital information from the optical communication unit 103b and converts the digital information to an electrical signal to store the electrical signal in the semiconductor memory 76.

Reference numeral 77 denotes a solar cell for supplying power to components of the memory disc 100b.

In the embodiment shown in FIG. 3A, the solar cell 77 is integrated in a portion of the memory disc 100b. Alternatively, in the embodiment shown in FIG. 3B, the solar cell 77 is formed on the entire upper or lower surface of the memory disc 100b or on both of the surfaces. In this case, the solar cell 77 can be formed on a large area, so that a large amount of power can be generated and supplied.

Reference numeral 78 denotes a disc input/output unit. The disc input/output unit provides an interface for uploading contents of the memory disc 11b to an external digital information storage device (for example, a PC) or a display apparatus (for example, a TV or a LCD monitor) or downloading digital information from the external digital information storage device or the display apparatus.

In the bio memory disc according to the embodiment, the disc input/output unit 78 may have a universal serial bus (USB) communication protocol, an IEEE 1394 communication protocol, or an Internet communication protocol.

Referring to FIG. 3C, the memory disc 100b may further includes a multimedia reproducing function, a multimedia storing function, and a multimedia connecting function.

In the bio memory disc according to the embodiment, the memory disc 100b may further include a speaker 71b and a microphone 71a for converting audio information stored in the semiconductor memory 76 to an analog signal to reproduce audio or converting the audio information to a digital audio information to store the digital audio information in the semiconductor memory 76.

In the bio memory disc according to the present invention, the memory disc 100b may further include an image sensor 73 which stores image information in the semiconductor memory 76.

In the bio memory disc according to the present invention, the image sensor 73 may be a CCD sensor or a CMOS.

In the bio memory disc according to the present invention, the bio memory disc 100b may further include an LCD display unit which displays the image information reproduced from the semiconductor memory 76.

In the bio memory disc according to the embodiment, the bio memory disc 100b may further include a digital multimedia broadcast function, a TV/radio receiving function, or an electric calculating function.

In the bio memory disc according to the embodiment, the bio memory disc 100b may further include a mobile-phone transceiving function.

In the bio memory disc according to the embodiment, the bio memory disc 100b may further include a mirror.

In the bio memory disc according to the embodiment, the bio memory disc 100b may further include an IR receiver 79b.

Reference numeral 79a denotes a remote controller for transmitting a command signal to the bio memory disc 100b through the IR receiver 79b.

In the bio memory disc according to the embodiment, the bio memory disc 100b may further include function-associated key pads 72.

In the bio memory disc according to the embodiment, the key pad 72 may includes one or more buttons selected from a play button, a record button, a search button, a forward button, a reverse button, a stop button, a pause button, a power button, a conversation button, a conversation stop button, a menu button, a ten-key button, a camera on button, a TV on/off button, a TV channel up/down button, a volume up/down button, and a recording button.

In the bio memory disc according to the embodiment, the key pad 72 of the digital book 100c may further include a multi-functional button 72a including a jog shuttle button and four directional arrow buttons. Reference numeral 75 denotes a permanent magnet. Reference numeral 79c denotes a connector connected to a DC jack for supplying a DC power. Reference numeral 79d denotes a connection hole into which an ear phone is inserted.

Reference numerals 75a, 75b, and 75c denote a DMB receiver, a TV/radio receiver, and a mobile-phone transceiver, respectively. Reference numeral 75d denotes a memory disc controller that is a micro-programmed controller for controlling components of the memory disc.

Figure 3D:
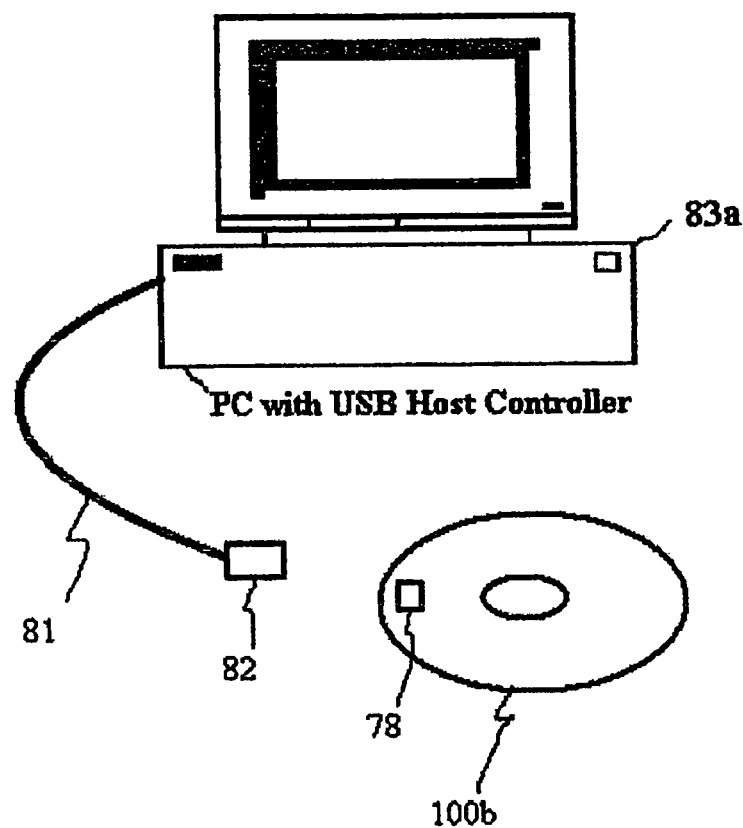
FIG. 3D is a schematic view illustrating a bio memory disc having a disc input/output unit and a PC connected through the disc input/output unit.
Figure 3E:
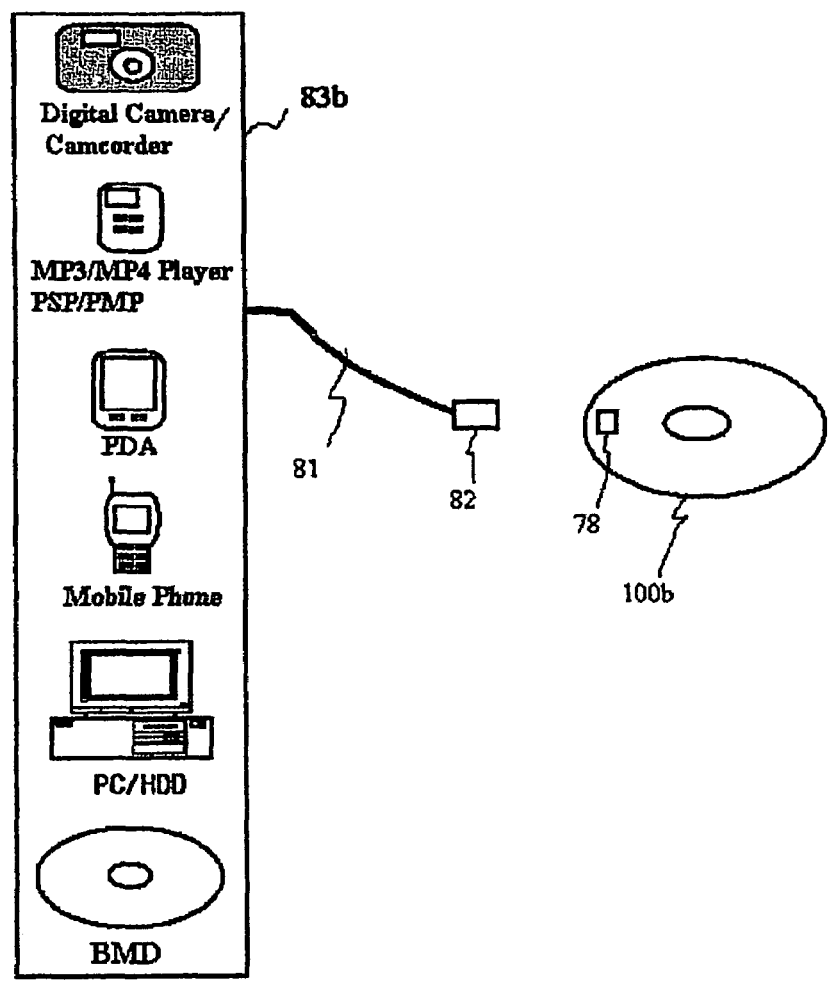
FIG. 3E is a schematic view illustrating a bio memory disc having a disc input/output unit and various external digital information storage devices connected through the disc input/output unit.

FIG. 3D is a schematic view illustrating a memory disc 100b having a disc input/output unit 78 and a PC 83a connected through the disc input/output unit. FIG. 3E is a schematic view illustrating a memory disc 100b having a disc input/output unit 78 and various external digital information storage devices 83b connected through the disc input/output unit Reference numeral 82 denotes a universal serial bus (USB) socket or an IEEE 1394 socket, and reference numeral 81 denotes a cable therefor. Through the disc input/output unit 78, digital information can be downloaded or uploaded between the memory disc 100b the PC 83a or other external digital information storage devices 83b.

Figure 3F:
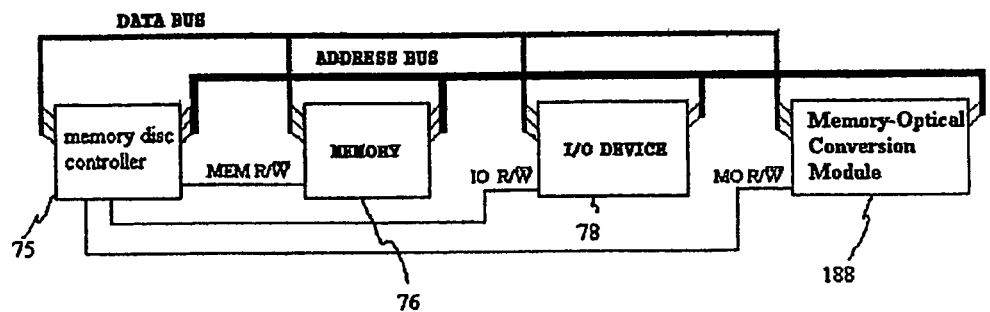
FIG. 3F is a system block diagram illustrating a bio memory disc.

FIG. 3F is a system block diagram illustrating the aforementioned memory disc 100b. Reference numeral 75 denotes a memory disc controller for controlling the semiconductor memory 7 integrated on the memory disc 100b, the memory optical conversion module 188, the disc input/output unit 78, and components of the memory disc 100b.

The memory disc controller 75 outputs control signals to the semiconductor memory 76, the memory optical conversion module 188, and the disc input/output unit 78), and the components of the memory disc 100b through an address bus and a data bus.

In the memory disc according to the embodiment, a memory optical conversion module searching process for optical alignment for an optical interface between the optical communication unit 103b and the memory optical conversion module 188 may be performed before a time of reading contents of the semiconductor memory 76 or writing digital information in the semiconductor memory 76.

In the bio memory disc according to the embodiment, the memory disc 100b may further include a permanent magnet 75 for easily performing optical alignment between the optical communication unit 103b and the memory optical conversion module 188.

Figure 3G:
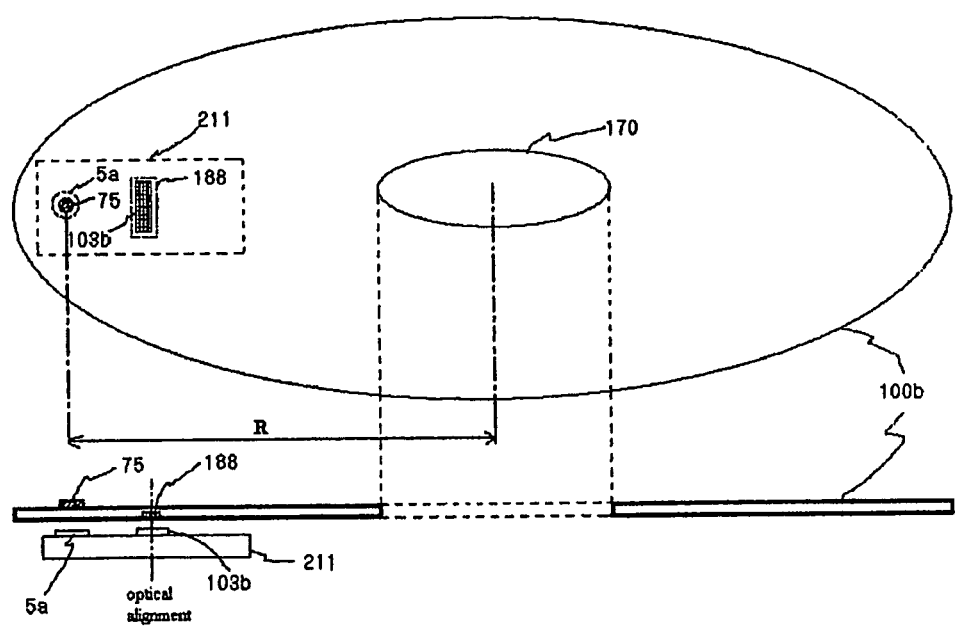
FIG. 3G is a view illustrating an example of an optical alignment between an optical communication unit and a memory optical conversion module.

FIG. 3G is a view illustrating an example of an optical alignment between the optical communication unit 103b and the memory optical conversion module 188.

The optical alignment is performed by using the memory optical conversion module searching process as follows.

Sine the permanent magnet 75 is apart from the center of the disc by a distance R, the movable permanent magnet 5a is moved by the distance R from the center by the slider 211, and the permanent magnet 75 is searched during repetition of short rotating and stopping of the memory disc 100b. While the permanent magnet 75 is searched, the permanent magnet 75 and the moveable permanent magnet 5a meet each other. At this time, due to the attractive force, the memory disc 100b is not rotated, so that the optical communication unit 103b is optically aligned with the memory optical conversion module 188. At the memory optical conversion module searching process is completed.

At the time of reading the semiconductor memory 76, the optical communication unit 103b serves as an optical receiver, and the memory optical conversion module 188 serves as an optical transmitter.

On the other hand, at the time of storing or writing the digital information in the semiconductor memory 76, the optical communication unit 103b serves as the optical transmitter, and the memory optical conversion module 188 serves as the optical receiver.

Figure 3H:
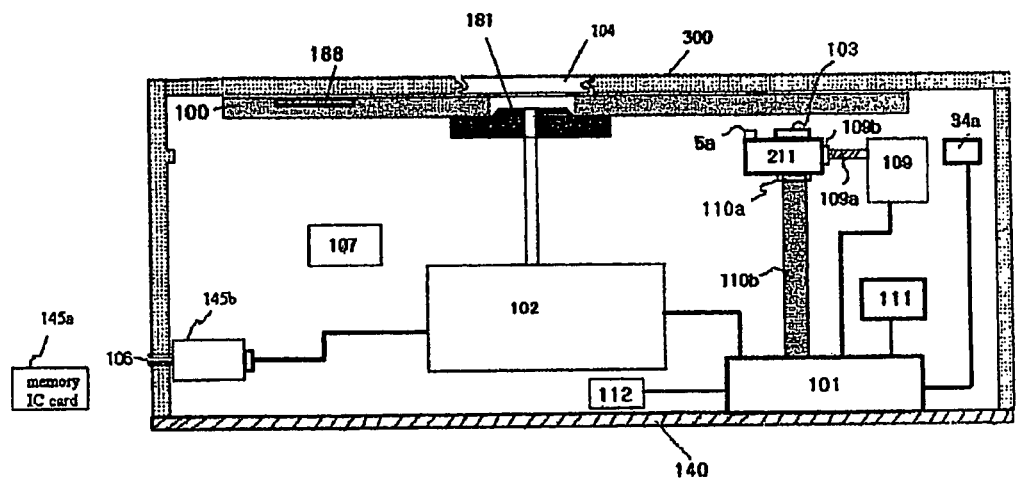
FIG. 3H is a schematic diagram illustrating an embodiment of a bio memory disc drive apparatus provided with a slider.

FIG. 3H is a schematic diagram illustrating an embodiment of a bio memory disc drive apparatus provided with the slider 211 shown in FIG. 2C which is used to control the aforementioned bio disc 100a, the aforementioned bio memory disc 100b, or a general optical disc such as CD and DVD;

Reference numeral 300 denotes a body of supporting the bio memory disc drive apparatus. A circuit board 140 is engaged with the body 300 of the bio memory disc drive apparatus in a lower surface thereof. A central controller 101 for controlling the bio memory disc drive apparatus and a storage unit 112 or an input/output unit 111 are disposed on the circuit board 140. The central controller 101) controls the spindle motor 120 to rotate or stop the bio memory disc 100. In addition, the central controller 101 controls the movement of the bio optical pickup module 103 disposed on the slider 211 by using the slider motor 109. In addition, the central controller 101 controls the movement of the permanent magnet 5a to open and close the valve of the bio memory disc. Since the permanent magnet 5a is disposed to close to the center of the fluid hole of the bio disc 100a, the permanent magnet 5a can effectively exerts the attractive force on the micro bead 70a in the bio disc 100a when the valve is opened.

In addition, the central controller 101 determines which of an optical disc including a CD, a CD-R, a game CD, and a DVD and a bio memory disc 100 is currently loaded on the bio memory disc drive apparatus. If the optical disc is loaded on the bio memory disc drive apparatus, the central controller 101 performs operations of the optical disc including transmitting contents read out by using the optical pickup device 103a from the optical disc to the storage unit 112 or the input/output unit 111, transmitting a to-be-written content to the optical pickup device 103a, or transmitting read/write control signals to the components. If the bio disc 100a is loaded on the bio memory disc drive apparatus, the central controller 101 performs operations for controlling the lab-on-a-chip process. If the memory disc 100b is loaded on the bio memory disc drive apparatus, the central controller 101 performs controlling reading of contents stored in the semiconductor memory 76 or writing of contents in the semiconductor memory 76.

The slider 211 is connected to worm gear connecting portions 109a and 109b connected to a shaft of the slider motor 109, so that the movement of the slider 211 can be controlled by the rotation of the slider motor 109.

Reference numeral 110b denotes a flexible cable for electrically connecting a central controller 101 to the BOPM 103 through a wafer or harness 11a to transmit control signals to the BOPM 103 on the slider 211.

In the bio memory disc drive apparatus according to the embodiment, the optical pickup device 103a or the bio optical pickup module 103 reads out a groove pattern, a data pattern, or a barcode pattern at a specific position of the bio memory disc 100 to allow the central controller 101 to determine which of a bio disc, a memory disc, and an optical disc is currently loaded on the bio memory disc drive apparatus.

The reading result of the assay site 132 detected by an optical measurement unit, an image sensor unit, an electrochemical measurement unit, an impedance measuring unit, a bio pit detecting unit, a fluorescence detecting unit, a radioactivity detecting unit, an SPR (surface plasmon resonance) detecting unit, or an QCM (quartz crystal microbalance) detecting unit is converted into an optical signal by the memory optical conversion module 188, and the optical signal is transmitted to the optical communication unit 103b. The optical signal is transmitted to the central controller 101, the storage unit 112, or the input/output unit 111 through the flexible cable 110b connected to the slider 211.

Reference numeral 34a denotes the slot determining means. In addition, the memory disc drive apparatus according to the embodiment may further include an IC card inserting slot 106 through which the memory IC card 145a is inserted into the bio memory disc drive apparatus. Information stored in the inserted memory IC card 145a is read out through a memory card reader 145b. Instead of the memory IC card, a USB memory stick may be used.

In the bio memory disc drive apparatus according to the embodiment, the memory IC card 145a stores personal encryption information or a reaction result and history of the assay site.

In the bio memory disc drive apparatus according to the embodiment, personal encryption verification is completed by inserting the memory IC card 145a into the memory IC card inserting slot 106, so that operations of the bio memory disc drive apparatus are enabled.

Reference numeral 181 denotes the turntable. Reference numeral 104 denotes an auxiliary turntable for preventing slip of the disc during the rotation of the turntable. Reference numeral 107 denotes a light source for illuminating a solar cell 77 on the bio memory disc.

Figure 3I:
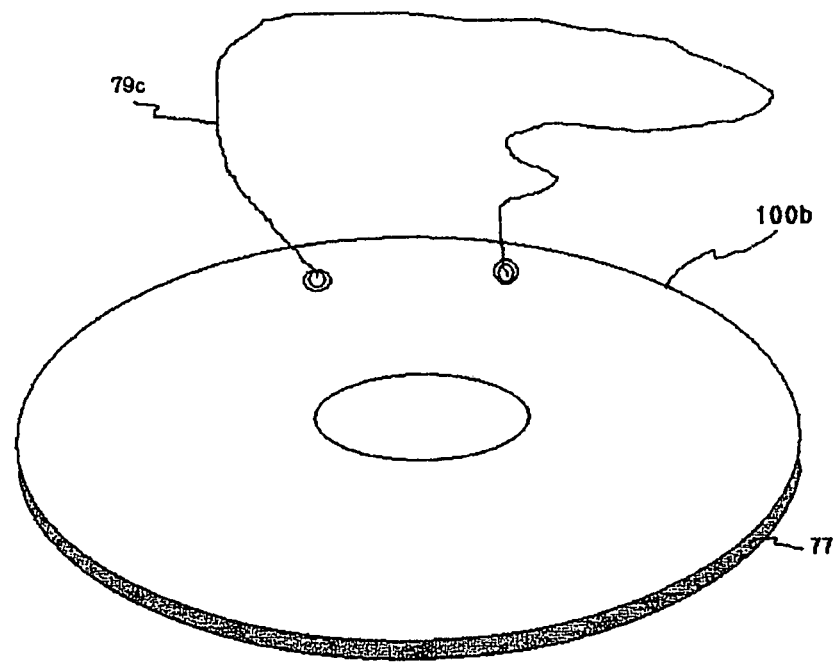
FIG. 3I is a view illustrating a necklace suspended with the bio memory disc according to an embodiment of the present invention.

FIG. 3I is a view illustrating a necklace suspended with the memory disc 100b according to an embodiment of the present invention.

Figure 3J:
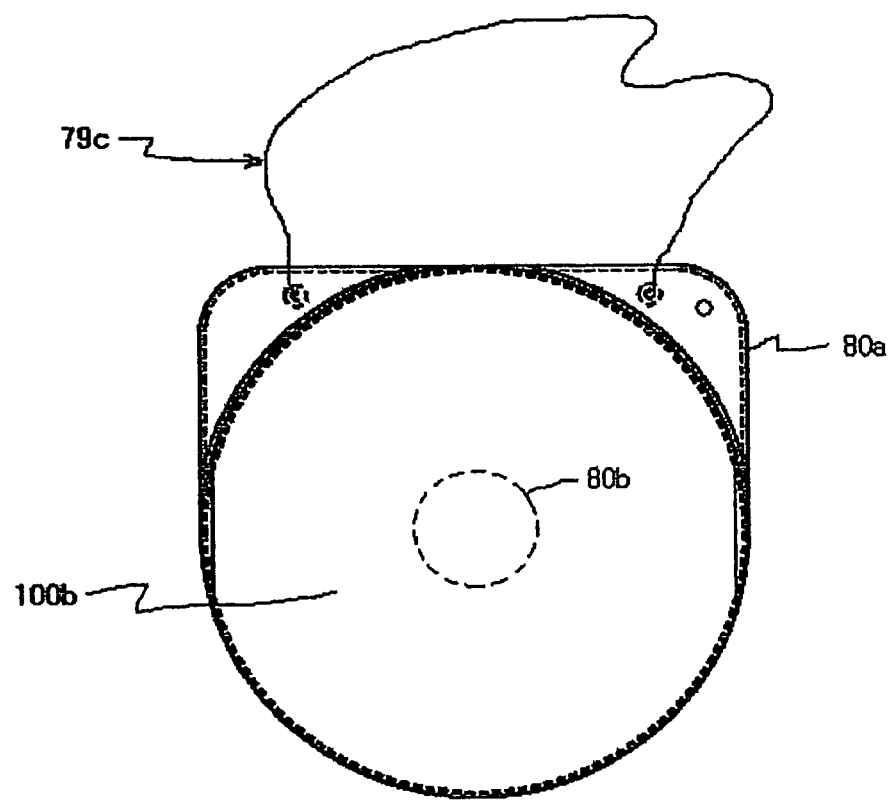
FIG. 3J is a view illustrating a wristlet suspended with the bio memory disc according to an embodiment of the present invention.

FIG. 3J is a view illustrating a wristlet suspended with the memory disc 100b according to an embodiment of the present invention. Reference numeral 79c denotes a necklace or a wristlet. Referring to FIG. 3J, the bio memory disc 100b is provided to the necklace or the wristlet. Reference numeral 80b denotes a central prominence on the cartridge which serves as a detaching/attaching means engaged with the disc aperture 170 of the memory disc 100b.

In the present invention, the necklace-type or wristlet-type cartridge may be further provided with a receiving portion for the solar cell or battery for supplying power to the bio memory disc.

Figure 3K:
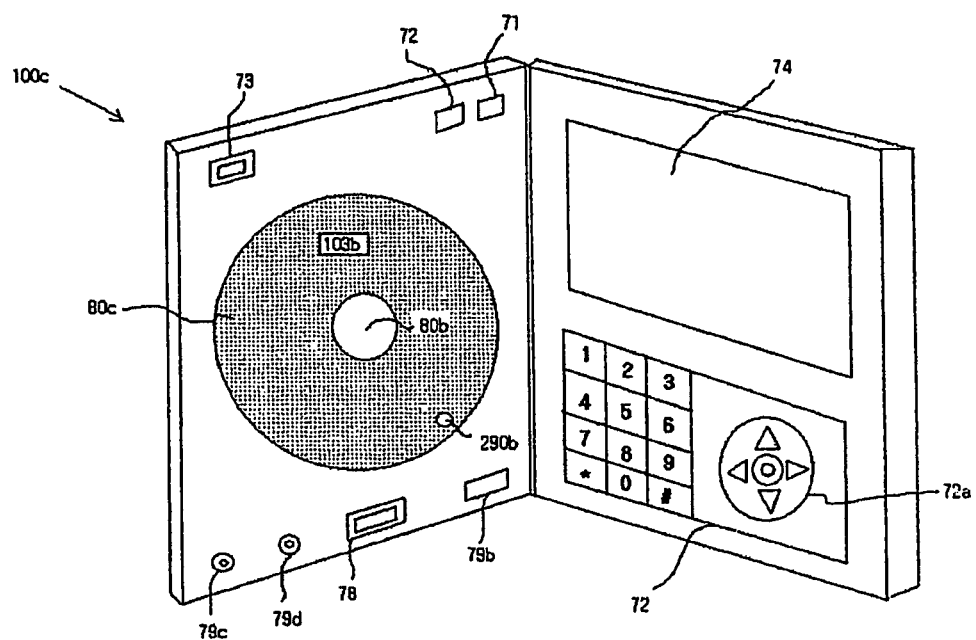
FIGS. 3K to 3M illustrate embodiments of a digital book.
Figure 3L:
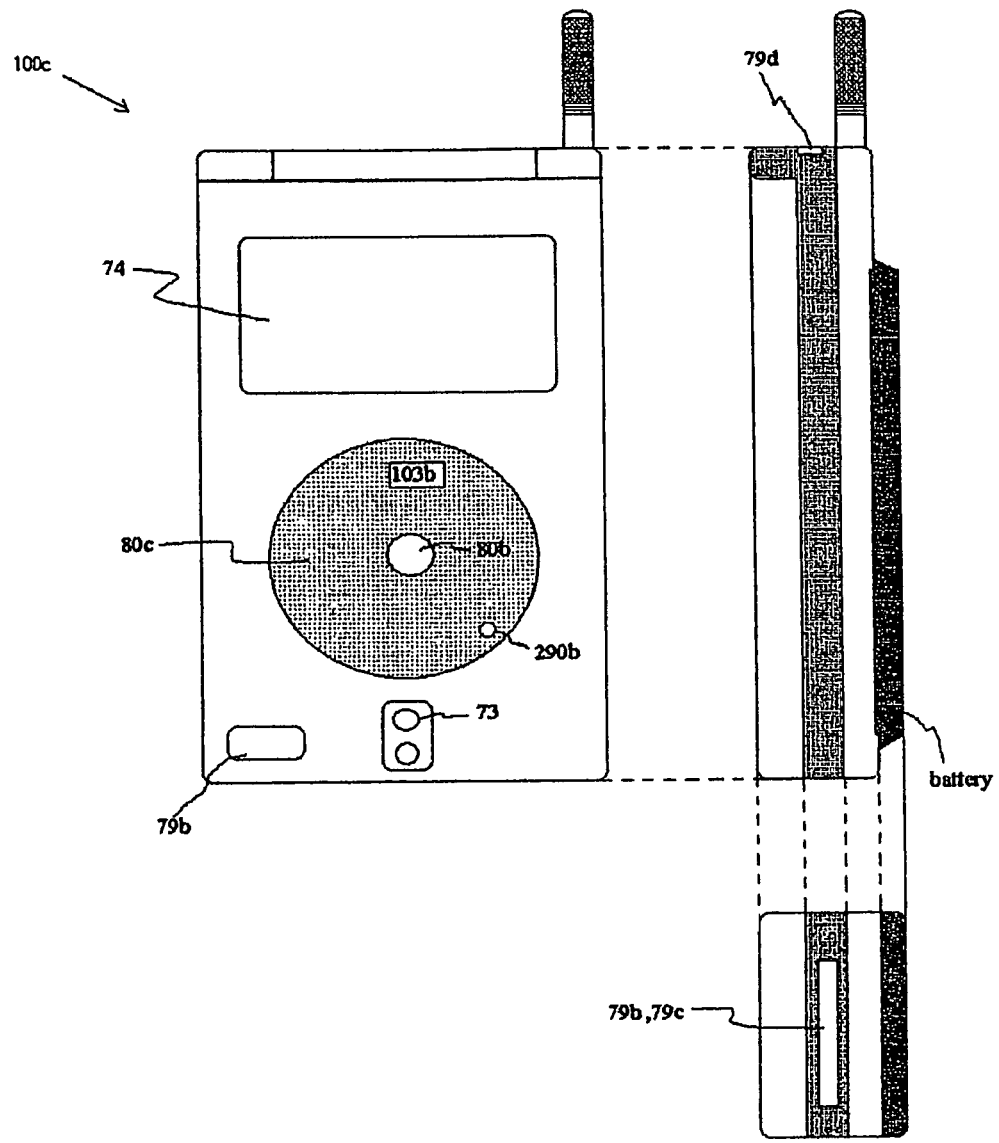
Figure 3M:
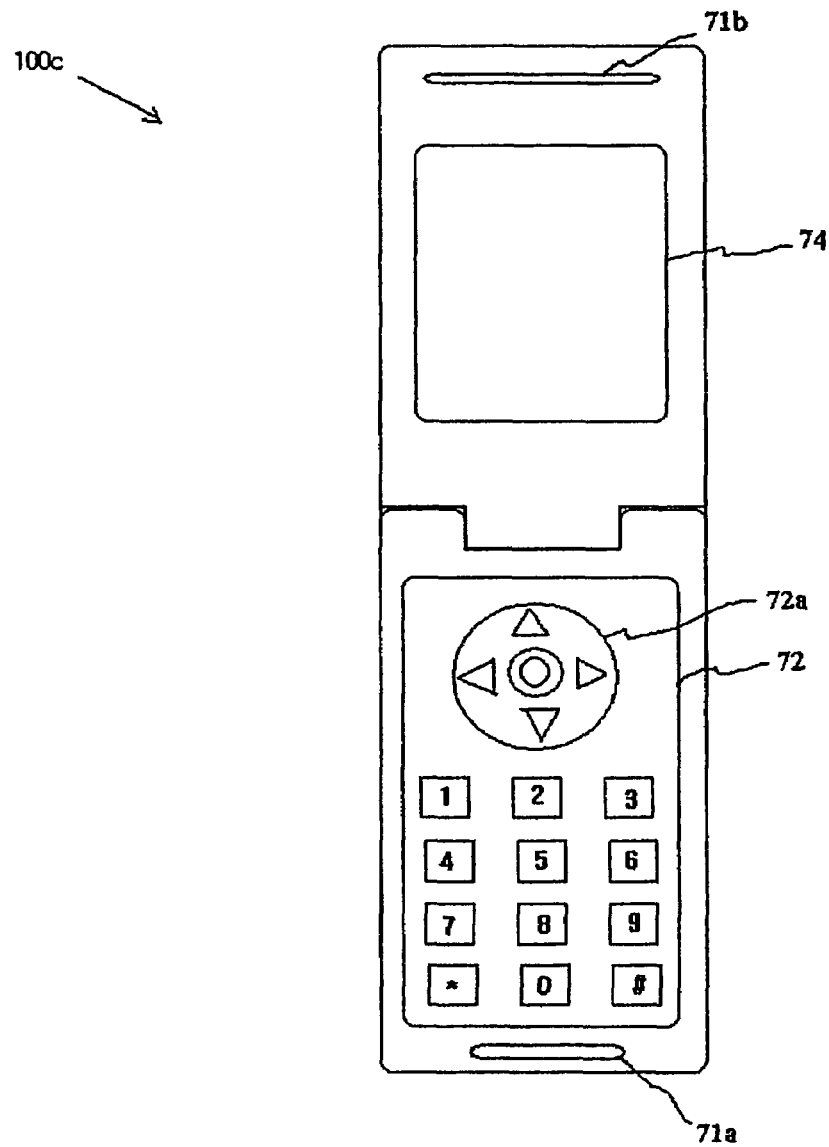

FIGS. 3K to 3M illustrate embodiments of a digital book in which the bio memory disc 100b shown in FIG. 3A or 3B or the aforementioned bio disc 100a can be mounted by a detaching/attaching means 80b and a mounting means 80c.

The digital book can be folded and unfolded like a general book.

The digital book has functions of reproducing, editing, and storing contents in the bio memory disc 100b. In addition, a student can use the digital book instead of a general book in a bag, so that the student can conveniently make a study, do homework, perform telecommunication, and access the Internet. In other word, the digital book provides the integrated multimedia function.

The digital book 100c further includes a speaker 71b and a microphone 71a to convert audio contents in the semiconductor memory 76 into an analog signal so as to reproduce audio or to convert the audio signal into digital audio information so as to store the digital audio information in the semiconductor memory 76.

The digital book 100c may further include an image sensor 73 for sensing image information and storing the image information in the semiconductor memory 76.

In the embodiment, the image sensor 73 may be a CCD sensor or a CMOS sensor.

The digital book 100c may further include an LCD display unit 74 for displaying the image information reproduced in the semiconductor memory 76.

The digital book 100c may further include a digital multimedia broadcast (DMB) function, a TV/radio receiving function, or an electric calculating function.

The digital book 100c may further include a mobile-phone transceiving function.

The digital book 100c may further include a mirror.

The digital book 100c may further include an IR receiver 79b.

The digital book 100c may further include a key pad 72 associated with functions of the digital book.

The key pad 72 of the digital book 100c may include one or more buttons selected form a play button, a record button, a search button, a forward button, a reverse button, a stop button, a pause button, a power button, a conversation button, a conversation stop button, a menu button, a ten-key button, a camera on button, a TV on/off button, a TV channel up/down button, a volume up/down button, and a recording button.

The digital book 100c may further include a plurality of the semiconductor memories 76.

In addition, the key pad 72 of the digital book 100c may further include a multi-functional button 72a including a jog shuttle button and four directional arrow buttons.

Reference numeral 78 denotes a disc input/output unit. The disc input/output unit provides an interface for uploading contents of the bio memory disc 100b to an external digital information storage device (for example, a PC) or a display apparatus (for example, a TV or a LCD monitor) or downloading digital information from the external digital information storage device or the display apparatus.

Reference numeral 79c denotes a connector connected to a DC jack for supplying a DC power. Reference numeral 79d denotes a connection hole into which an ear phone is inserted.

Although not shown in FIG. 3K, a bio memory disc controller for controlling the DMB receiver, the TV/radio receiver, the mobile-phone transceiver, and components of the bio memory disc is built in the digital book 100c.

In addition, the memory disc controller is optically interfaced with the optical communication unit 103b disposed in the body of the digital book 100c through the memory optical conversion module 188.

Reference numeral 290b denotes a reference prominence which is engaged with a reference hole 290a of the memory disc 100b to perform optical alignment between the optical communication unit 103b and the memory optical conversion module 188 at the time of mounting the memory disc 100b on the detaching/attaching mean 80b and the mounting mean 80c. The reference prominence together with the detaching/attaching mean and the mounting mean is disposed in the body of the digital book 100c. The mounting mean 80c may be formed on a surface of the body of the digital book 100c in an engraved shape so as to mounting the memory disc. The detaching/attaching mean 80b has a mechanism for being engaged with the central aperture of the memory disc.

The bio memory disc drive apparatus shown in FIG. 3H is included in the body of the digital book 100c, so that the bio disc 100a is top-loaded on the detaching/attaching means 80b to perform a nucleic acid hybridization assay function, an immuno-assay function, or a remote diagnosis function. In this case, the detaching/attaching means 80b has a function as the turntable 181. Namely, the detaching/attaching means 80b is designed to be connected to the shaft of the spindle motor 102, so that the detaching/attaching means 80b can be rotated separately from the body of the digital book 100c.

FIGS. 3L and 3M are views illustrating an embodiment of a mobile phone modified from the aforementioned digital book 100c.

Figure 4A:
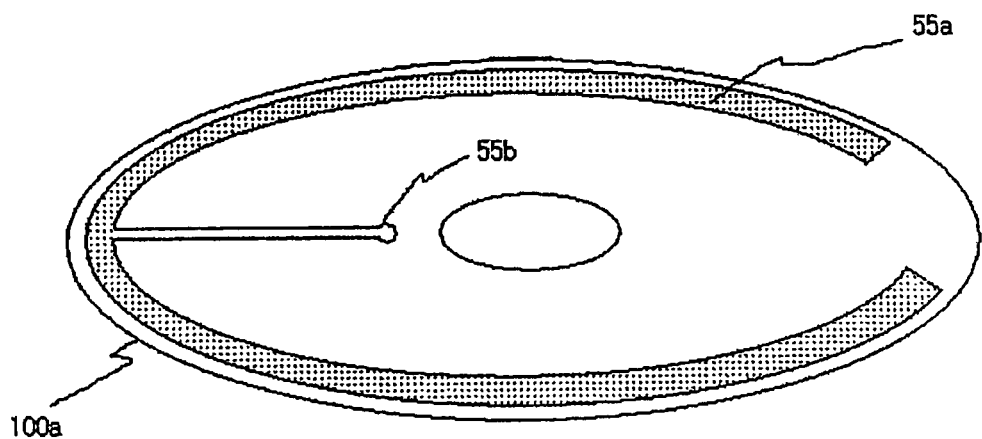
FIG. 4A is a view illustrating an embodiment of a liquid automatic balancing system (ABS) chamber.

FIG. 4A is a view illustrating an embodiment of a liquid automatic balancing system (ABS) chamber 55a which is constructed in a form of doughnut along a circumference of a bio disc 100a. The doughnut form can be partially deleted at a part of which weight is higher than the other parts. Sine the liquid ABS chamber 55a contains a liquid material, the liquid ABS chamber 55a can compensate for a warbling of the bio disc 100a due to eccentricity of the bio disc 100a during rotation of the bio disc 100a by using the fluidity of the liquid material. The liquid ABS chamber 55a can maintain a horizontality of the bio disc 100a to stabilize the rotation of the bio disc 100a and to minimize noise during the rotation of the bio disc 100a. Reference numeral 55b denotes an ABS inlet for injecting the liquid material into the liquid ABS chamber 55a.

FIG. 4B to 4F are views illustrating an embodiment of a preparation chamber 130 and an excess chamber 90.

Reference numeral 70a denotes a valve, and reference numeral 91 denotes an outlet of the excess chamber 90.

Figure 4B:
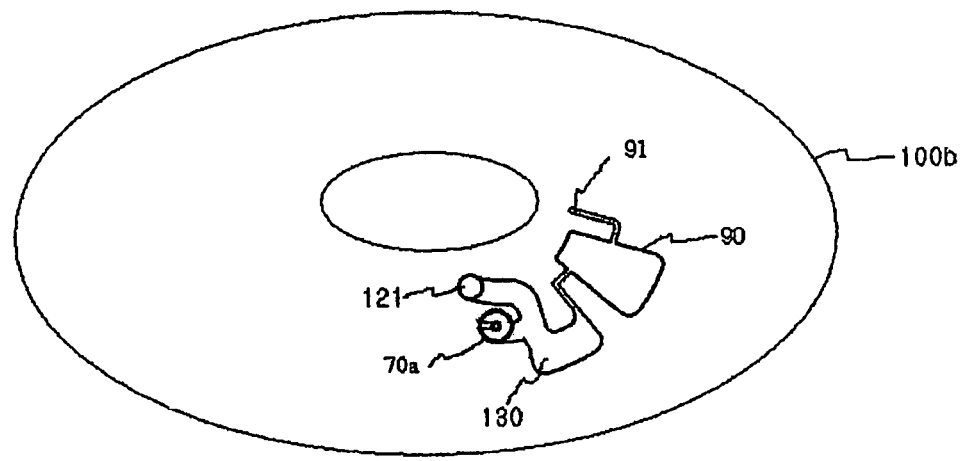
FIG. 4B to 4F are views illustrating an embodiment of a preparation chamber and an excess chamber.
Figure 4C:
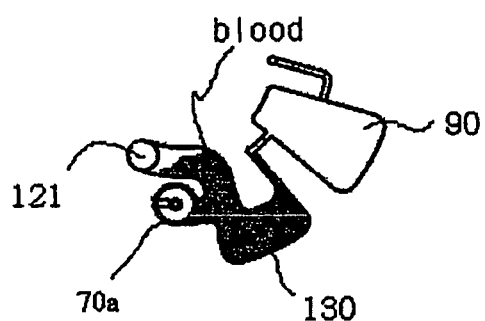
Figure 4D:
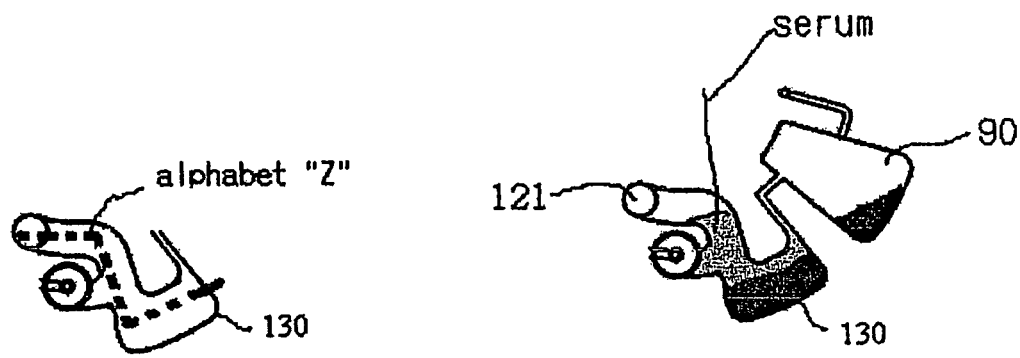

Referring to FIG. 4B, the preparation chamber 130 is disposed on the bio memory disc 100a. A sample inlet 121 for injecting a sample is provided to the preparation chamber 130. An excessively injected sample of the preparation chamber 130 is transferred to the excess chamber 90, so that a fixed quantity of sample can be contained in the preparation chamber 130. Referring to FIG. 4C, blood is injected into the preparation chamber 130 through the sample inlet 121 before centrifugal separation. The blood is injected in the state that the valve 70 is closed. The blood injected though the sample inlet 121 is separated into serum (or plasma) and blood clot through the centrifugal separation. Generally, a ⅓ of a human blood is the serum (or plasma). The serum and the blood clot centrifugally separated from the blood through a high speed rotation of the bio memory disc 100b are shown in FIG. 4D. The upper portion of the preparation chamber 130 is the serum (or plasma). According to the embodiment, the preparation chamber 130 is a Z-shaped chamber. In this case, as much as the serum (or plasma) can be contained in the preparation chamber after the centrifugal separation. When the bio memory disc 100b is rotated in the state that the valve 70a is opened, only the serum (or plasma) can be transferred to the next camber. If a large amount of the serum (or plasma) is not contained, it is very different to separate and transfer only the serum (or plasma) to the next chamber.

In the bio memory disc according to the embodiment, the preparation chamber 130 may further include a gauge or a level indicating means for informing an operator of a minimum amount of the injected sample (or blood).

In the bio memory disc according to the embodiment, the gauge or the level indicating means may be a fixed quantity indicating line 94 drawn on the preparation chamber.

Figure 4E:
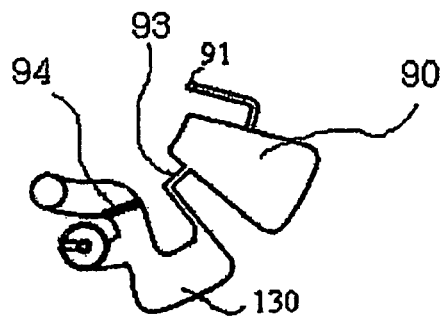

Referring to FIG. 4E, the fixed quantity indicating line 94 of the preparation chamber 130 is drawn as a black line.

In the bio memory disc according to the embodiment, the fixed quantity indicating line 94 may be the black line 94 drawn on the preparation chamber 130.

The bio memory disc according to the embodiment may further include the aforementioned excess chamber 90 for containing an excessively injected sample so that only the fixed quantity of sample can be contained in the preparation chamber 130. Reference numeral denotes an outlet of the excess chamber 90.

In the bio memory disc according to the embodiment, the excess chamber allows a level of a fixed quantity channel 93 to match the fixed quantity indicating line 94, so that the excessive quantity of sample over the fixed quantity indicating line 94 can be transferred to the excess chamber 90 through the fixed quantity channel 93.

In the bio memory disc according to the embodiment, the excessive quantity of sample (or blood) can be transferred to the excess chamber 90 through the fixed quantity channel 93 due to a centrifugal force during the rotation of the bio memory disc.

Figure 4F:
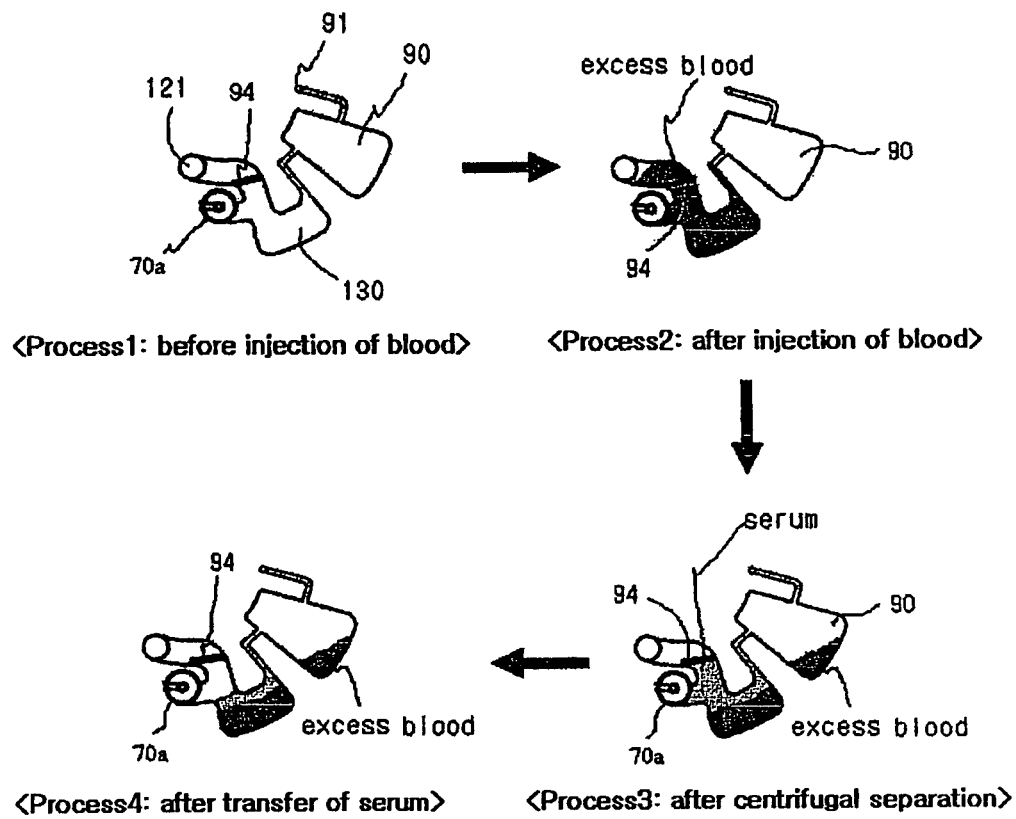

FIG. 4F illustrates processes for injecting the sample and separating the serum (or plasma) from the sample in the preparation chamber 130. Process 2 illustrates a state that a blood exceeding the fixed quantity indicating line 94 is injected into the preparation chamber 130. Process 3 illustrates a state of the centrifugal separation that the excessively injected quantity of blood exceeding the fixed quantity indicating line 94 is transferred to the excess chamber 90 and the fixed quantity of blood is separated into the serum and the blood clot. Process 4 illustrates a state that the valve 70a is opened, so that only the serum (or plasma) is transferred to the next chamber.

Figure 4G:
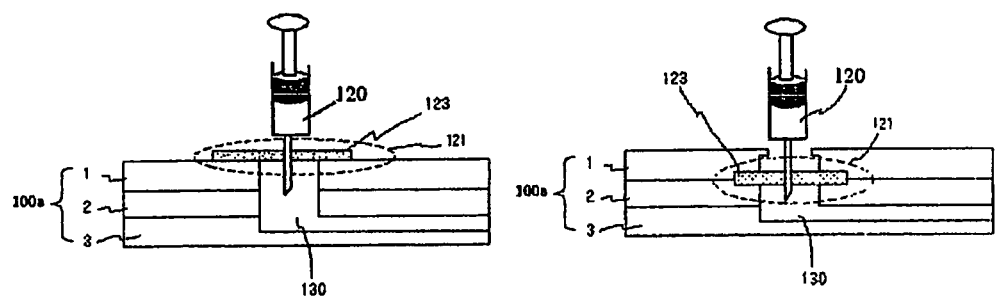
FIGS. 4G to 4H are views illustrating embodiments of the sample inlet.
Figure 4H:
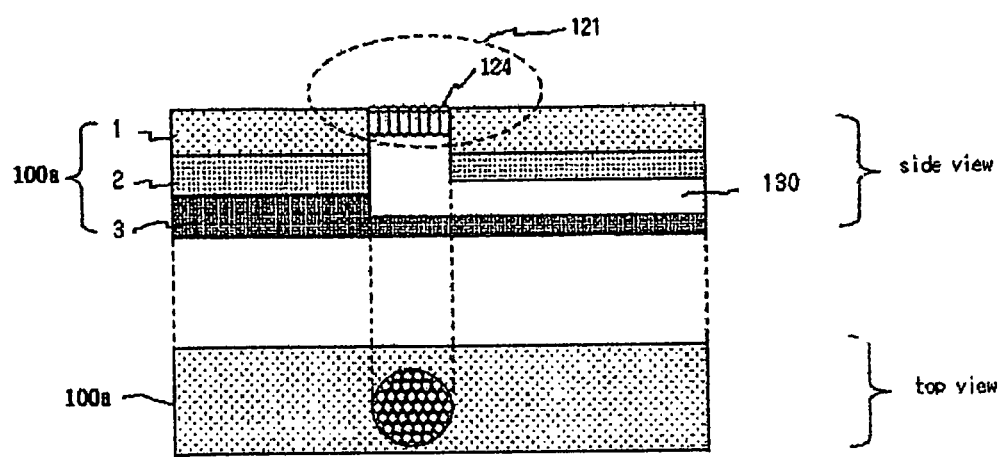

FIGS. 4G to 4H are views illustrating embodiments of the sample inlet 121.

Referring to FIG. 4G, the sample (or blood) is injected into the preparation chamber 130 through a syringe needle that penetrate an inlet cover 123.

In the bio memory disc according to the embodiment, the sample inlet 121 may be covered with a thin inlet cover 123, and a need of a syringe may penetrate the inlet cover 123 so that the sample (or blood) is injected into the preparation chamber 130 through the needle.

In the bio memory disc according to the embodiment, the inlet cover 123 may be made of vinyl.

In the bio memory disc according to the embodiment, the sample inlet 121 is constructed with a least one capillary tube 124 or a bundle of the capillary tubes, so that the sample (or blood) contacting the sample inlet 121 is automatically sucked into the preparation chamber 130 due to capillary phenomenon.

Figure 4I:
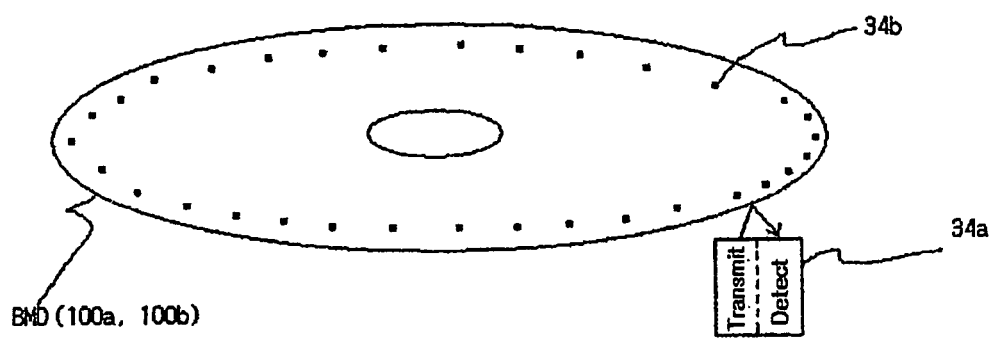
FIGS. 4I and 4J are views illustrating embodiments of a bio memory disc where a plurality of slots are disposed along the circumference of the bio memory disc.
Figure 4J:
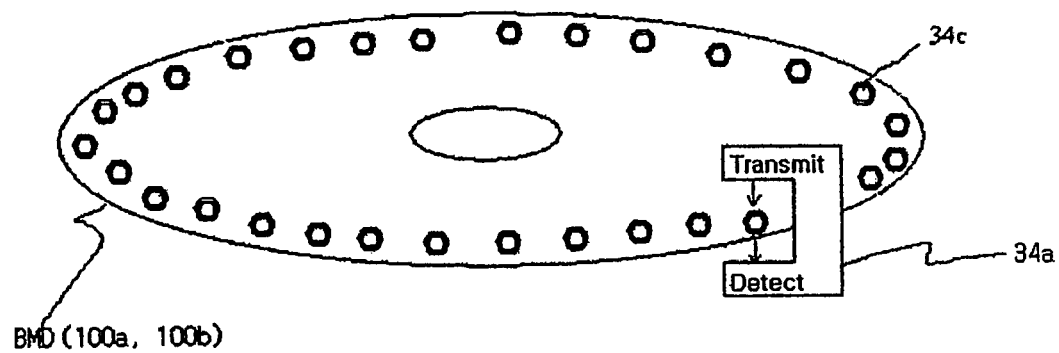

FIGS. 4I and 4J are views illustrating embodiments of bio memory discs where a plurality of slots 34b or 34c are disposed along the circumference of the bio memory disc so as to be used to detect rotation, rotation angle, and rotation number of the bio memory disc 100. FIG. 4I illustrates a bio memory disc provided with a light reflective type slot detecting means. FIG. 4J illustrates a bio memory disc provided with an light transmissive type slot detecting means. Reference numeral 34b denote an optical reflector as a type of slot, and reference numeral 34c denotes an opening as another type of slot. Reference numeral 34a denotes a slot detecting means for detecting the slots.

In the bio memory disc according to the embodiment, the slots 34b or 34c may be disposed along the circumference of the bio memory disc in various slot sizes and intervals, so that the rotation angle and the rotation number as well as the rotation of the bio memory disc can be detected.

The slots may be disposed with different slot sizes according to azimuthal angles. In this case, the slot sizes are detected by the slot detecting means 34a so that the rotation angle (azimuthal angle) of the bio memory disc can be detected. In addition, the slots may be disposed with different slot intervals. In this case, the slot intervals are detected by the slot detecting means 34a so that the rotation angle (azimuthal angle) of the bio memory disc can be detected.

For example, when the slot is detected, the slot detecting means 34a outputs an electrical signal of logic 1, and when the slot is not detected, the slot detecting means 34a outputs an electrical signal of logic 0. Therefore, during the rotation of the bio memory disc 100, the slot detecting means 34a outputs a sequence of pulses. A central controller 101 detects the pulses to determine the rotation or the rotation angle of the bio memory disc.

Since the rotation, the rotation angle, or the rotation number of the bio memory disc can be detected by the slot detecting means 43a or an FG signal determining means, the present invention can further improve accuracy and speed of the azimuthal valve detecting process in comparison to the prior art disclosed in Korean Patent Application No. 10-2005-0038765 titled by "digital bio disc, digital bio disc drive apparatus, and method therefor". Namely, the azimuthal direction valve searching operation is performed by rotating a spindle motor 102 at a low speed while a slider 211 is stopped or by repeating a shot rotation and a stop of the spindle motor. In this case, since the rotation angle and the rotation number of the bio memory disc can be detected by the slot detecting means 34a, the short rotation of the spindle motor can be controlled.

In the bio memory disc according to the embodiment, the azimuthal direction valve searching operation may be performed by using the slot detecting means 34a or the FG signal determining means.

In addition, since the short rotation of the spindle motor can be controlled by using the slot detecting means 34a or the FG signal determining means, an optical alignment between the optical communication unit 100b and the memory optical conversion module 188 can be easily performed. In other words, a memory optical conversion module detecting process can be easily performed.

Figure 4K:
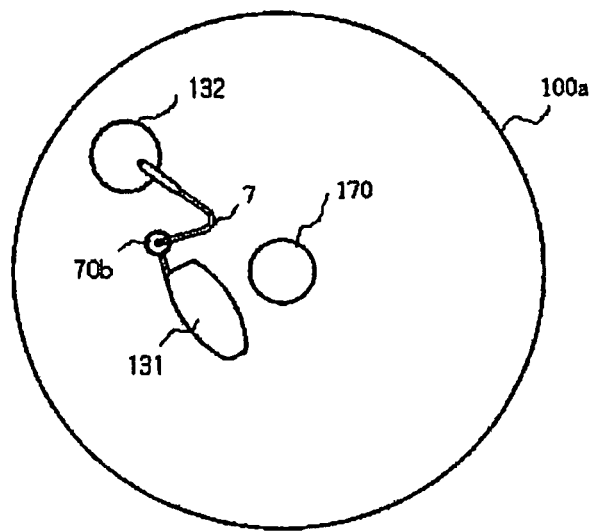
FIGS. 4K to 4M are views illustrating embodiments of a liquid valve.
Figure 4L:
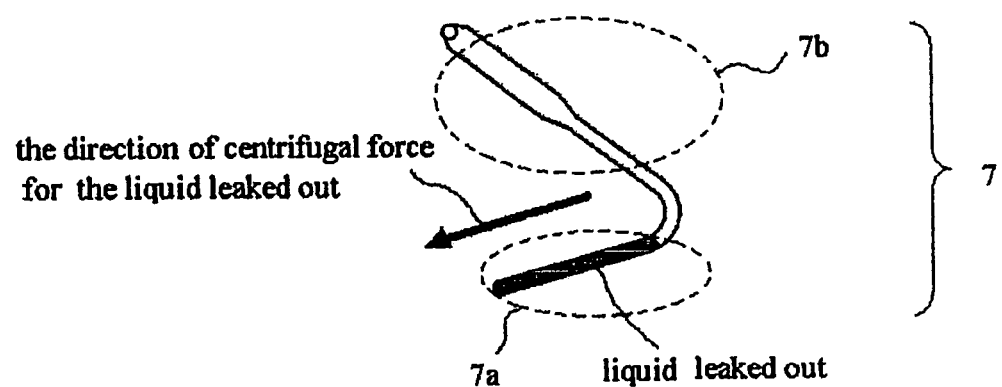
Figure 4M:
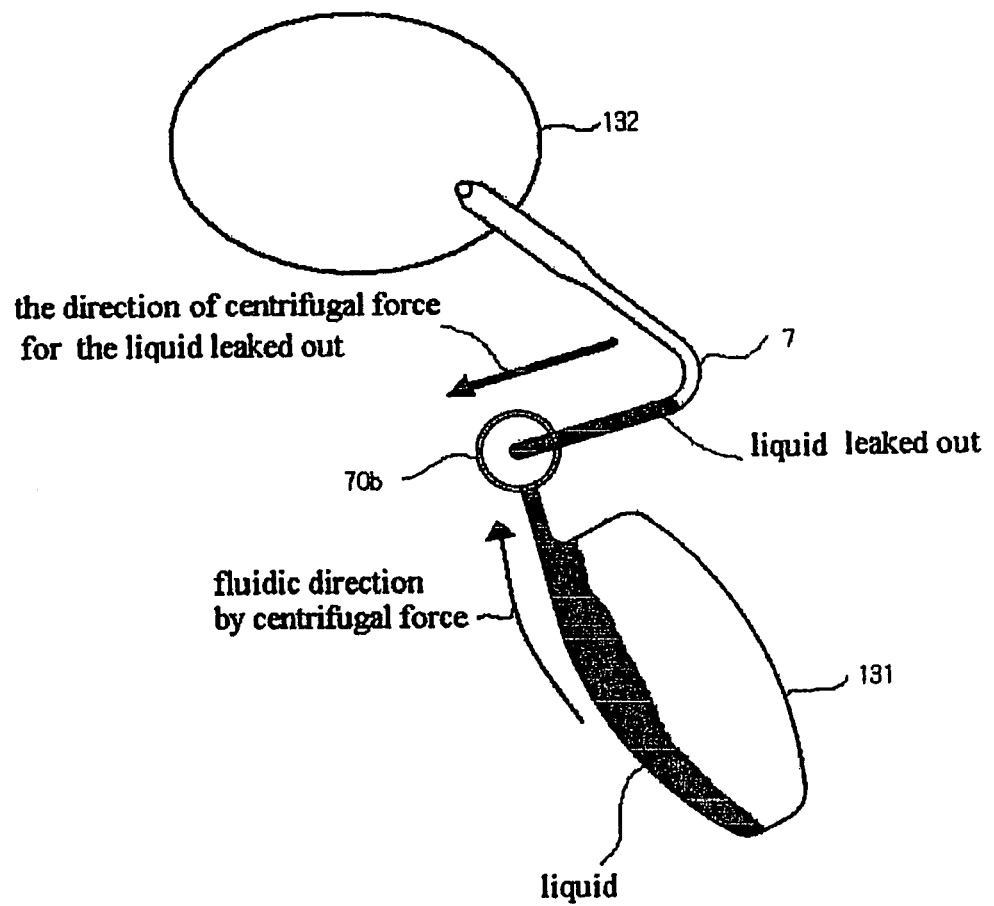

FIGS. 4K to 4M are views illustrating embodiments of a liquid valve for preventing leakage of a liquid material during a high speed rotation of the bio memory disc.

In a case where the liquid is leaked out from the chamber 131 due to malfunction of the valve 70b during the rotation of the bio disc 100a, the transfer of the leaked liquid into the next chamber 132 can be prevented by a V-shaped channel 7 disposed at the outlet of the valve 70b.

FIGS. 4K to 4M are detailed views illustrating a V-shaped channel provided with a liquid valve. The V-shaped channel 7 is mainly divided into the liquid valve 7a (the former half of the V) and a channel portion 7b (the latter half of the V) and its angle point is oriented toward the center of the bio disc 100a. The liquid valve 7a is operated as follows. When the valve 70b is malfunctioned during the high-speed rotation of the bio disc, the liquid valve 7a is filled with the liquid leaked out from the chamber 131. Once the liquid valve 7a is filled, a centrifugal force is exerted to the liquid contained in the liquid valve in the radial direction, so that the liquid cannot be leaked out from the valve 70b. Moreover, the leaked liquid can be withdrawn toward the chamber 131 due to the centrifugal force.

In other words, in a case where some of the liquid is leaked out from the chamber 131 during the high-speed rotation of the bio disc 100a, a force of leaking out the liquid and the centrifugal force of the leaked liquid are balanced with each other, so that the further liquid cannot be leaked out. The exertion of the centrifugal force on the leaked liquid for preventing the leakage of the liquid is referred to a liquid valve operation in the present invention.

The bio memory disc according to the embodiment may further comprises the liquid valve which is provided to the outlet of the aforementioned vale so as to prevent the leakage of the liquid during the high-speed rotation of the bio memory disc.

The bio memory disc according to the embodiment may further comprise the V-shaped channel 7 which is provided to the outlet of the aforementioned valve so as to prevent the leakage of the liquid during the high-speed rotation of the bio memory disc.

Figure 5A:
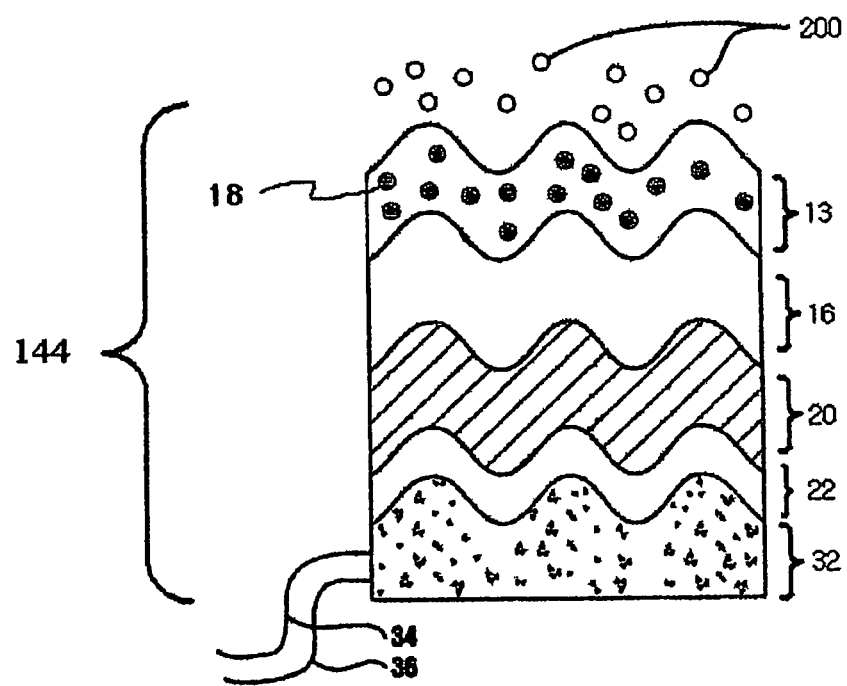
FIG. 5A is a view illustrating an embodiment of a fluorescence detecting unit.

FIG. 5A is a view illustrating an embodiment of a thin-film-structured fluorescence detecting unit 144 for reading out an assay site.

A fluorescence sensor is a device for sensing light emitted from a fluorescent material. After the fluorescent material is excited by an excitation laser, the fluorescence sensor senses the light emitted form the fluorescent material, so that the presence of the fluorescent material can be determined. The technique for sensing the fluorescent materials is well-known by the ordinarily skilled in the art.

In U.S. Pat. No. 4,649,280 (Mar. 10, 1987) and U.S. Pat. No. 5,006,716 (Apr. 9, 1991), there is disclosed a fluorescence detecting unit where a thin-film waveguide layer is integrally formed under a fluorescent material so as to improve performance of detecting light emitted from the fluorescent material. However, in this case, the fluorescence sensor is not integrated therein. In particular, in U.S. Pat. No. 5,841,143 (Nov. 24, 1998), there is disclosed a small-sized, high-performance fluorescence detecting unit where a fluorescence sensor and a noise filter are integrated in the aforementioned thin-film fluorescence detecting unit by using a very large scale integration (VLSI) technique. However, U.S. Pat. Nos. 4,649,280, 5,006,716, and 5,841,143 have two problems as follows. Firstly, an array of the assay site is not provided to the fluorescence detecting unit.

Recently, an array where different types of bio materials can be spatially addressed has been formed on a solid-state container. Due to an array of capture probes, a large number of assay items of a sample can be simultaneously assayed.

For example, there is a system where an array for capturing complementary assay items is fixed on the solid-state container. One of the systems is proposed by Fodor (Nature, Vol. 364, 1993. 8. 5). In the system, a short oligonucleotide probe attached on the solid-state container is complementarily bounded to a long DNA strand in a liquid sample. After that, a nucleotide sequence of the sample is calculated based on a collected hybridization data by a computer Therefore, there is needed an assay system having an assay site provided with a spatially addressable array in a sample format, capable of easily performing assay of multiple-type samples in a single fluid test sample or assay of single-type sample in a multiple fluid test sample by using a single step or minimum steps.

Secondly, in the aforementioned Patent Documents, a substrate layer for fixing the capture probes are not provided in the aforementioned thin-film fluorescence detecting unit. In the thin-film fluorescence detecting unit disclosed in the aforementioned Patent Documents, the topmost layer is the waveguide layer. When there is a gaseous or liquid fluorescent material on the waveguide layer, the fluorescent is detected. However, in general, an antibody or oligonucleotide probe is fixed as a capture probe on the substrate layer of the assay site, and the capture probe is specifically bound with a material in a fluorescence-labeled sample through an Ag-Ab reaction or hybridization process of the fluorescence-labeled sample. Therefore, a thin-film fluorescence detecting unit having no substrate layer cannot be used as the assay site of the bio memory disc.

The fluorescence detecting unit 144 according to the embodiment is constructed by stacking several thin films on a substrate layer.

The sample may be a fluorescence-labeled material 200 which may have a liquid state, a gas state, or a solid state.

Reference numerals 13, 16, 20, 22, and 32 denote the substrate layer, the waveguide layer, the metal film layer, the buffer layer, and the fluorescence sensor layer, respectively.

The waveguide layer, the metal film layer, the buffer layer, and the fluorescence sensor layer are disclosed in the aforementioned Patent Documents: U.S. Pat. No. 4,649,280 (Mar. 10, 1987), U.S. Pat. No. 5,006,716 (Apr. 9, 1991), and U.S. Pat. No. 5,841,143 (Nov. 24, 1998).

In addition, the corrugated shapes of the layers are described in detail in the Patent Documents.

Reference numeral 18 denotes a capture probe 18 fixed on the substrate layer.

Reference numeral 200 denotes a fluorescence-labeled antigen or fluorescence-labeled DNA sample, which has a specific binding with respect to the capture probe 18. An amount of the sample having a specific binding is proportional to an amount of the fluorescent material. Accordingly, qualitative analysis and quantitative analysis can be performed by using the fluorescence sensor layer 32. The intensity of fluorescence sensed by the fluorescence sensor layer 32 is converted into an electrical signal and output through electrical signal lines 34 and 36.

The electrical signal is transmitted through the electrical signal lines 34 and 36 to the memory optical conversion module 188. The memory optical conversion module 188 converts the electrical signal into an optical signal and transits the optical signal including a fluorescence reading result of the assay site to the optical communication unit 103b.

In the bio memory disc according to the embodiment, the assay site 132 may include a fluorescence detecting unit which is integrally constructed by stacking or integrating a substrate layer, a waveguide layer, a metal film, a buffer layer, and a fluorescence sensor layer.

In the bio memory disc according to the embodiment, the assay site 132 may include a fluorescence detecting unit which is integrally constructed by stacking or integrating a substrate layer, a waveguide layer, a metal film, a buffer layer, and a fluorescence sensor layer on a wafer by using a chemical process.

In the bio memory disc according to the embodiment, at least one selected from the substrate layer, the waveguide layer, the metal film, the buffer layer, and the fluorescence sensor layer of the assay site is stacked in a corrugated shape.

In the bio memory disc according to the embodiment, the fluorescence sensor layer 32 may be a photo sensor.

In the bio memory disc according to the embodiment, the substrate layer 13 of the fluorescence detecting unit 144 includes an array of multiple-type capture probes.

In the bio memory disc according to the embodiment, the assay site 132 includes an array of the fluorescence detecting units 144.

In the bio memory disc according to the embodiment, each element of the array of the fluorescence detecting units 144 is individually (spatially) addressed.

In the bio memory disc according to the embodiment, the individual (spatial) addressing of the elements in the array of the fluorescence detecting units 144 is performed by using an excitation laser scanning process.

In the bio memory disc according to the embodiment, the elements in the array of the fluorescence detecting units 144 is sequentially excited by the laser scanning process, and the intensity of the fluorescence emitted from the excited fluorescence label is sensed by the fluorescence sensor layer 32.

Figure 5B:
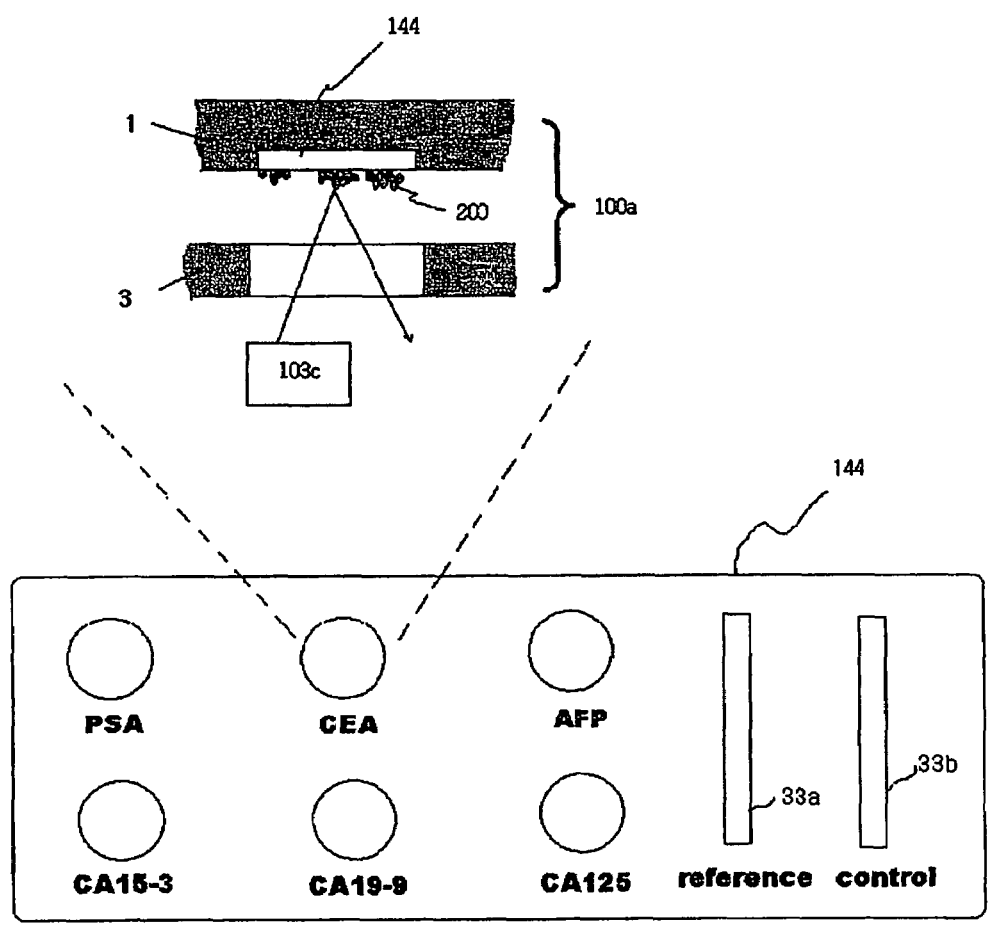
FIG. 5B is a view illustrating an embodiment of an assay site reading method which is implemented by a fluorescence detecting unit.

FIG. 5B is a view illustrating an embodiment of an assay site reading method which is implemented by the fluorescence detecting unit 144. As capture probes, 6-type of tumor markers are fixed in an array on the substrate layer 13. In the embodiment, six tumor markers AFP, PSA, CEA, CA19-9, CA125, and CA15-3 are fixed in the substrate layer 13.

Reference numeral 200 denotes a fluorescence-labeled antigen or a fluorescence-labeled DNA sample. An amount of the sample having a specific binding with the capture probes on the substrate layer 13 is proportional to an amount of the fluorescent material. The intensity of fluorescence emitted by the excitation laser unit 103c is sensed by the fluorescence sensor layer 32 and converted into an electrical signal. The electrical signal indicates the intensity of the fluorescence of the area spatially addressed by the excitation laser beam. The electrical signal is converted into an optical signal by the memory optical conversion module 188 and transmitted to the optical communication unit 103b.

In the embodiment, the assay site 132 may further include a reference line 33a and a control line 33b.

In the embodiment, the reference line 33a or the control line 33b may be constructed with spots.

In the embodiment, the fluorescence intensity of the reference line is set to a cutoff value of the fluorescence intensity so as to easily determine a negative or positive reactivity.

Figure 5C:
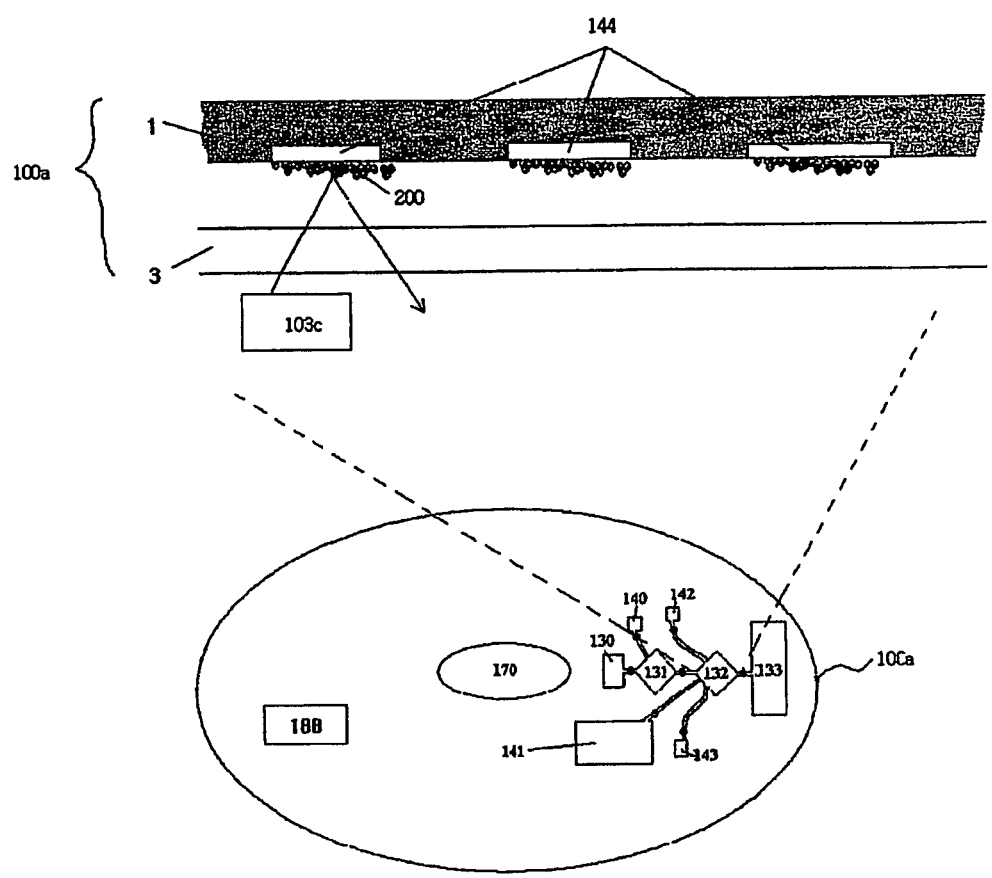
FIGS. 5C to 5E are views illustrating embodiments of an assay site in which a plurality of the fluorescence detecting units are integrated.
Figure 5D:
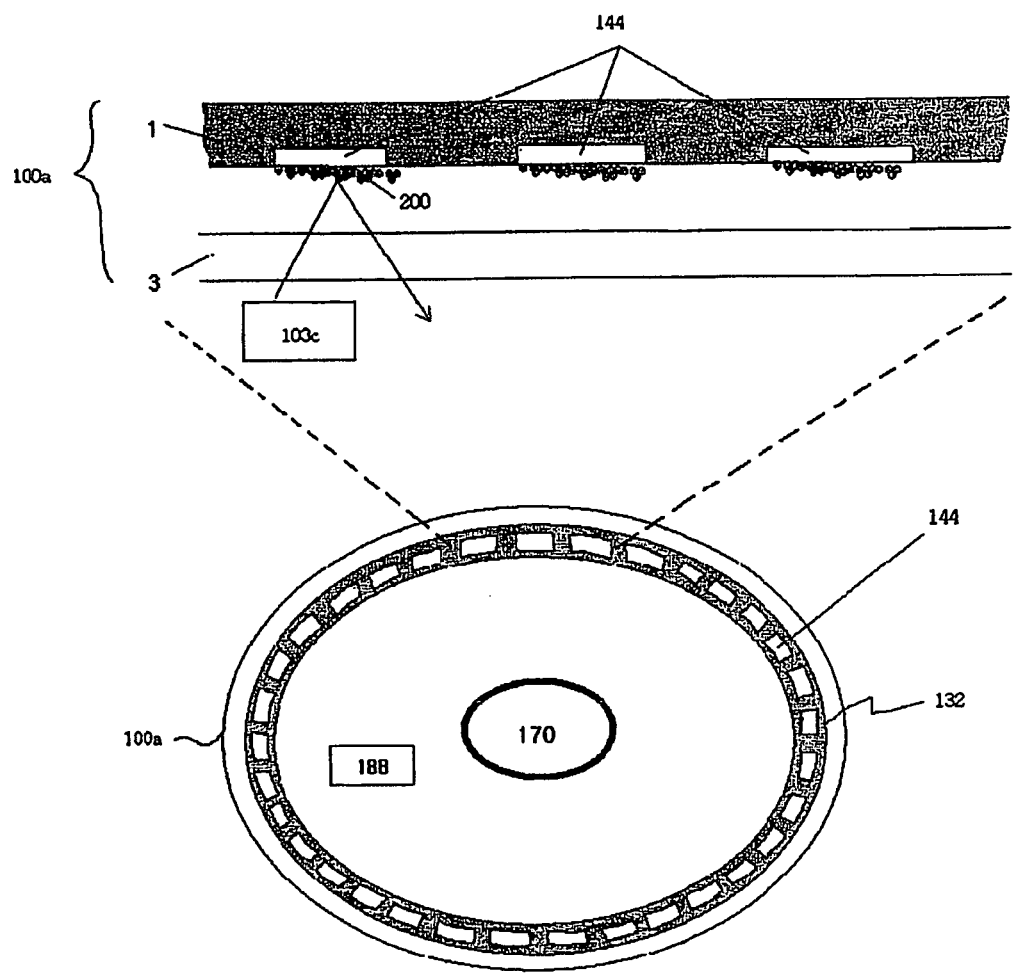
Figure 5E:
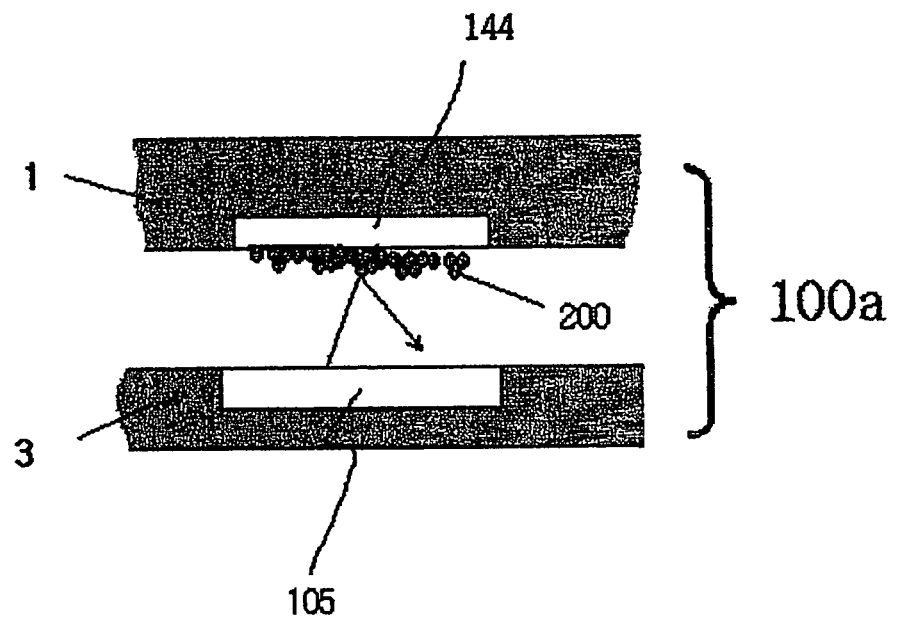

FIGS. 5C to 5E are views illustrating an embodiment of an assay site 132 in which a plurality of the fluorescence detecting units 144 are integrated. The substrate layer 13 of the fluorescence detecting unit 144 is spatially addressed by the excitation laser unit 103c, so that the intensity of the fluorescence of the substrate layer 13 of the fluorescence detecting unit 144 is sequentially read out. The reading result is converted into an optical signal by the memory optical conversion module 188, and the optical signal is transmitted to the optical communication unit 103b. Reference numeral 200 denotes a fluorescence-labeled antigen or a fluorescence-labeled DNA sample. The spatial addressing is performed by the rotation of the bio memory disc and the movement of the slider 211.

FIG. 5D is a view illustrating an embodiment of a bio memory disc 100a where an array of the fluorescence detecting units 144 is disposed along a circumference of the assay site 132. During the rotation of the bio memory disc, the fluorescence detecting units 144 are sequentially spatially addressed by the excitation laser unit 103c. The reading result is converted into an optical signal by the memory optical conversion module 188, and the optical signal is transmitted to the optical communication unit 103b.

FIG. 5E is a view illustrating an embodiment of a bio memory disc where elements of the array is disposed in one-to-one correspondence with semiconductor lasers 105.

The elements of the array is excited by the corresponding semiconductor lasers 104. An electrical signal proportional to the intensity of fluorescence is transmitted through electrical signal lines 34 and 36 to the memory optical conversion module 188. The memory optical conversion module 188 converts the electrical signal into an optical signal and transmits the optical signal as a reading result of the assay site to the optical communication unit 103b. According to the embodiment shown in FIG. 5E, the rotation of the bio memory disc and the movement of the slider 211 are not needed to perform the spatial addressing during the reading of the assay site. In addition, the elements of the array are directly scanned with the laser beam in the vicinity thereof, so that it is possible to further improve the performance of detecting the fluorescence.

In the bio memory disc according to the embodiment, the assay site includes an array of antibodies or DNAs is fixed as a capture probe on a porous membrane.

Preferably, the porous membrane is constructed by coating inter-digit electrodes on a surface of the porous membrane. The porous membrane may be a nitro-cellulose membrane or a nylon membrane. Preferably, the array is constructed by fixing myoglobin, CK-MB, or troponin I (TnI) as a coronary thrombosis marker.

Preferably, the array is constructed by fixing glutamine synthetase as an Alzheimer disease marker.

Figure 6A:
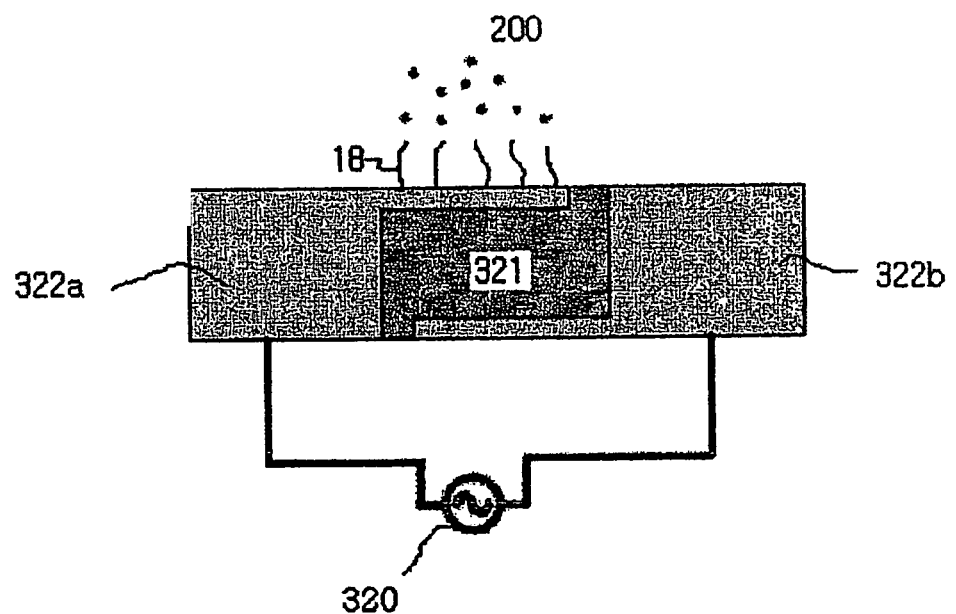
FIGS. 6A to 6C are views illustrating an embodiments of the QCM detecting unit.
Figure 6B:
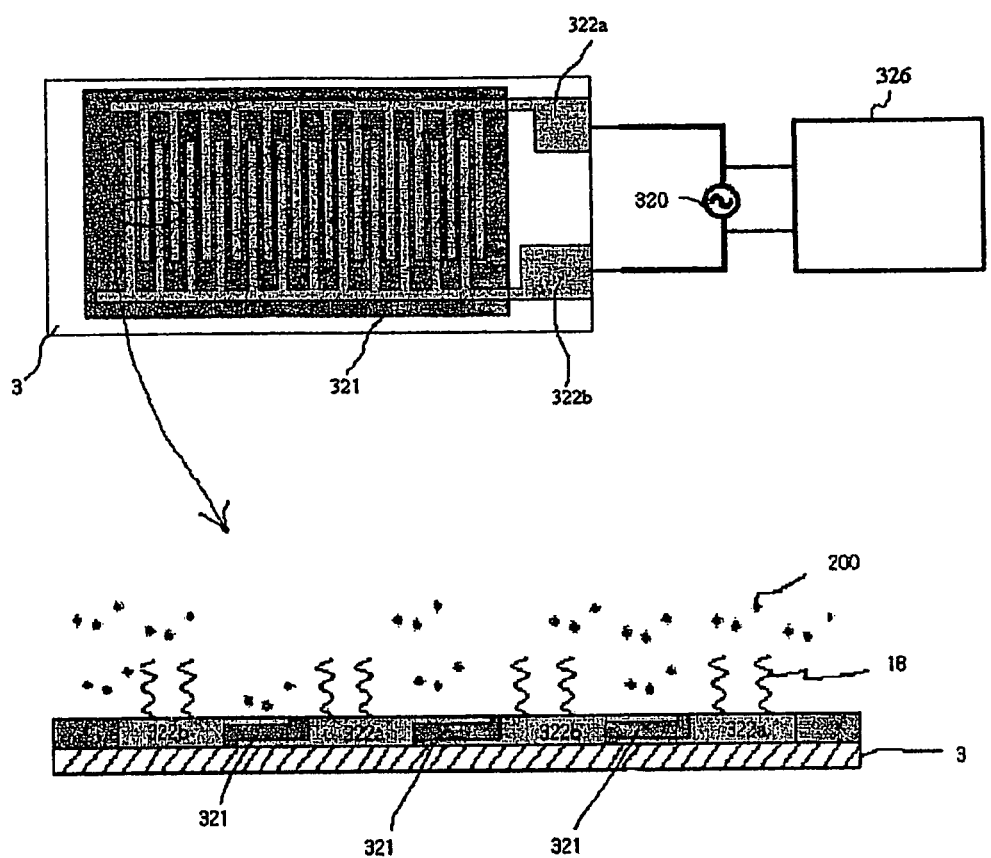
Figure 6C:
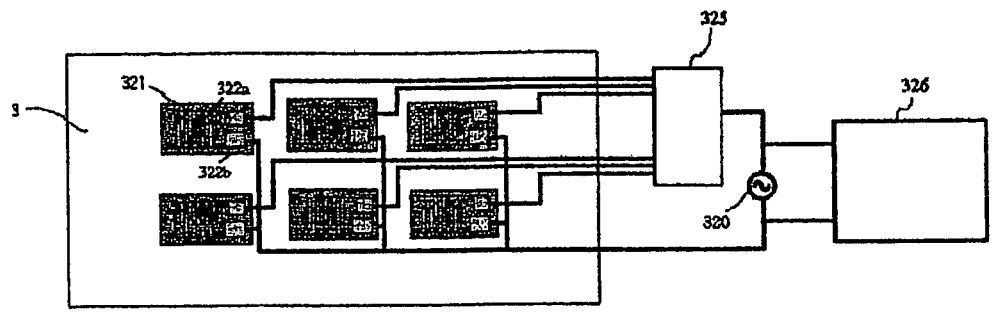

FIGS. 6A to 6C are views illustrating an embodiments of the QCM detecting unit.

The QCM detecting unit detects a resonance frequency change $\Delta f$ corresponding to an increase in weight caused from binding of different types of materials, so that a specific binding of the different types of materials can be read out.

The QCM detecting unit includes a quartz 321, overlapped electrodes 322a and 322b facing each other with the quartz 321 interposed, and an AC signal generator 320.

Reference numeral 18 denotes a capture probe. When the capture probe is specifically bound with the antigen or DNA sample 200, the weight thereof is increased, so that the resonance frequency is changed. The resonance frequency change is detected by the QCM detecting unit.

In the embodiment, the quartz 321 is made of silicon crystal. The quartz 321 is constructed by depositing the overlapped electrodes 322a and 322b on the silicon crystal by using a semiconductor manufacturing process.

Due to the overlapped electrodes 322a and 322b, the QCM detecting unit can be produced by using the semiconductor manufacturing process.

In the bio memory disc according to the embodiment, the QCM detecting unit may perform the detection after the assay site 132 of the bio memory disc is dehydrated or dried by the high speed rotation of the bio memory disc.

Measurement errors of the QCM detecting unit may be caused from humidity or the liquid state of the assay site. According to the present invention, the problem can be solved by the detection of the assay site after the dehydrating or drying thereof by the rotation of the bio memory disc.

FIG. 6B is a view illustrating an embodiment where the overlapped electrodes 322a and 322b of the QCM detecting unit are designed to be disposed in an inter-digit manner. The facing area between the two electrodes 322a and 322b is increased according to the number of digits, so that a sensitivity of the QCM detecting unit can be improved.

In addition, a change in resonance frequency caused from the reaction is measured by an impedance measurement unit 326, so that a degree of the specific binding can be quantitatively analyzed.

Reference numeral 3 denotes the lower disc.

In addition, in the present invention, the AC signal generator 320 may further include a digital-to-analog (D/A) converter for converting a digital signal of the impedance measurement unit 326 to an analog voltage signal so as to change a frequency of the AC signal generator 320. Preferably, the AC signal generator 320 may be a voltage controlled oscillator (VOC) that is controlled by using an analog voltage signal.

FIG. 6C is a view illustrating an embodiment where an array of the QCM detecting units shown in FIG. 6B is disposed. Reference numeral 325 denotes a multiplexer for sequentially selecting elements of the array. A resonance frequency change of each element selected by a multiplexer 326 is independently measured by an impedance measurement unit 326, so that a degree of a specific binding with the assay site can be quantitatively read out.

Figure 7A:
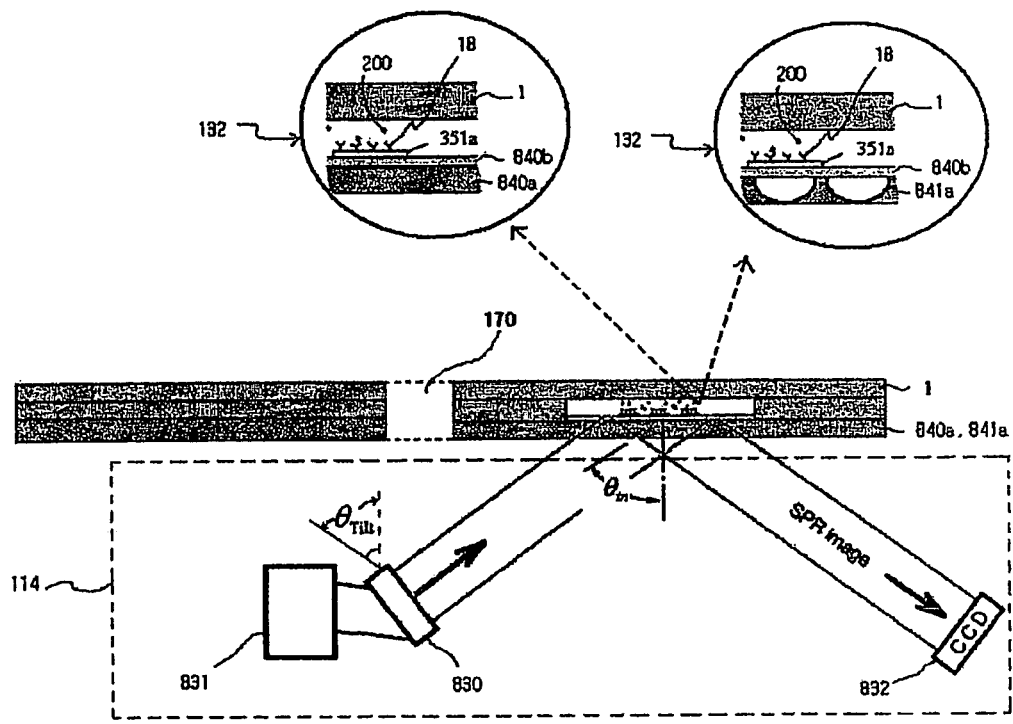
FIGS. 7A and 7B are views illustrating embodiments of a surface plasmon resonance (SPR) detecting unit.
Figure 7B:
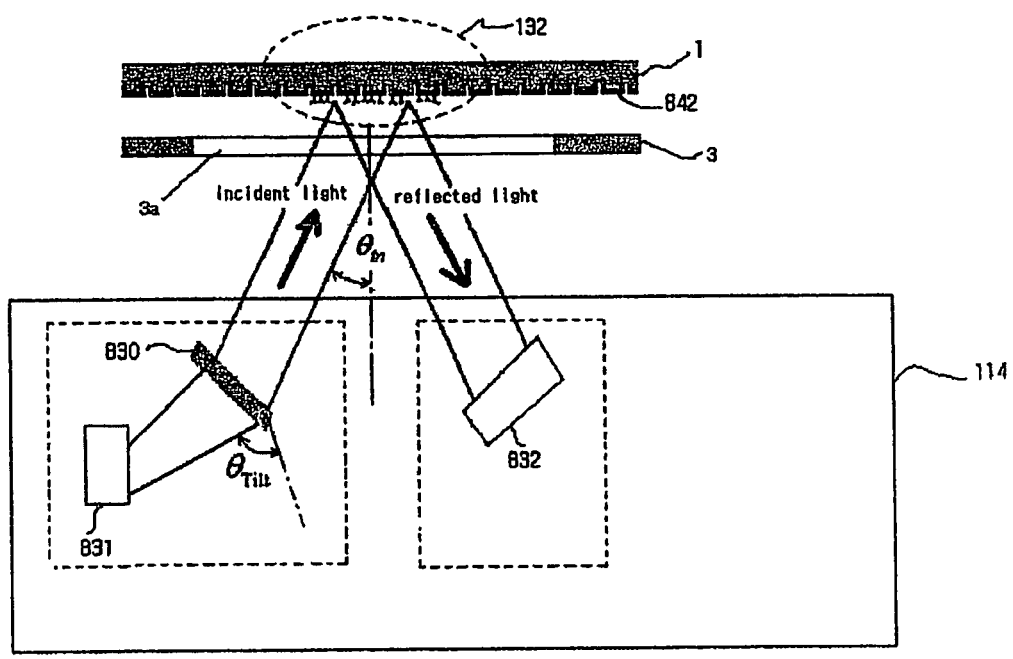

FIGS. 7A and 7B are views illustrating embodiments of a surface plasmon resonance (SPR) detecting unit.

When a wave vector of an incident wave, that is, a monochromatic P-polarized wave matches a wave vector of a surface plasmon wave at a predetermined angle of a varying incident angle $\theta_{in}$ over a total reflection angle, resonance is obtained. At the resonance, all the energy of the incident wave is absorbed into a metal. Therefore, light incident to a surface of the metal is not reflected but converted into the surface plasmon, so that the reflectance is dropped greatly. When a chemical reaction or a specific binding reaction with a capture probe occurs on the surface of the metal thin film, the condition of resonance is changed. As a result, the resonance angle or resonance wavelength is also shifted in proportion to a degree of the chemical reaction or the specific binding reaction.

Since the resonance wavelength shift occurs according to a change in composition of bio materials that are interacted with each other on a surface of a sample, the surface plasmon phenomenon can be effectively used to measure interaction between bio materials, that is, a binding affinity. In addition, the resonance wavelength shift increases in proportion to a change in a degree of the specific binding, so that it is possible to obtain a quantitative result. In addition, instead of the resonance wavelength shift, the resonance angle shift is measured so as to quantitatively analyze the binding affinity between different types of bio materials.

In a case where the surface plasmon resonance phenomenon is used for the immuno-assay, the surface of the metal is coated with an antibody which is responsive to a specific antigen, and the antigen is introduced. Next, light is illuminated so as to generate the surface plasmon resonance. Based on a proportional relation between the resonance wavelength (or angle) shift and an amount of the bound antigen, a concentration of the antigen can be measured.

In a case where the surface plasmon resonance phenomenon is used for the nucleic acid hybridization assay, the surface of the metal is coated with a capture probe which is responsive to complementary double strand of a specific DNA (or RNA) sequence, and the DNA (or RNA) sequence is introduced. Next, light is illuminated so as to generate the surface plasmon resonance. Based on a proportional relation between the resonance wavelength (or angle) shift and an amount of the bound DNA (or RNA) sequence, a concentration of the DNA (or RNA) sequence can be measured.

An SPR detecting unit using the surface plasmon resonance phenomenon, there are proposed (i) an SPR sensor using a diffraction grating, (ii) an SPR sensor using an optical waveguide, and (iii) a Kreschmann SPR sensor using a prism.

The Kreschmann SPR sensor (The determination of the optical constants of metals by excitation of surface plasmons, Z. Physics 241 1971) page 313-324) has various measurement parameters and high sensitivity. However, the Kreschmann SPR sensor is hard to miniaturize and integrate. In order to solve the problem, a metal diffraction-grating-based SPR sensor using a metal diffraction grating instead of the prism is disclosed by H. Raether in his article (Surface plasma oscillations and their applications, Phys. Thin Films 9 1977, page: 145-260).

A grating-based or grating-coupled SPR sensor using grooves are formed on a CD is disclosed in the article, titled, "A Surface plasmon resonance gas sensor in a compact disc format" (Sensors and Actuators B 56 1999, P254-258) written by W. A. Challener.

However, there are the following problems in that the diffraction-grating-based SPR sensor is adapted to the bio memory disc according to the present invention.

<Problems of Adaptation of the Diffraction-Grating-Based SPR Sensor to the Bio Memory Disc>

Measurement variable of the diffraction-grating-based SPR sensor is limited to only the light intensity unlike a prism-based SPR sensor. In case of the diffraction-grating-based SPR sensor, when the 2-D array of the assay sites is read out by using a 2-D CCD camera, an SPR image is obtained based on light intensity.

The interaction of the capture probe fixed on the 2-D array of the assay site results in the SPR angle shift where the reflected light is minimized. As a result, the reflectance is changed according to a degree of specific binding of the sample and the elements on the 2-D array of the assay site. Accordingly, there is a difference of the light intensity between the specifically bound element and the non-interacted element. The assay site can be quantitatively analyzed based on the difference. In order to obtain an optimized SPR image, before the reaction and after the reaction, the optic system needs to be designed to be set to an optimal incident angle where the contrast of the light intensity is maximized. However, the design is very difficult to implement.

In the bio memory disc drive apparatus according to the present invention, various bio memory discs are repeatedly loaded and ejected. Therefore, it is substantially impossible to set the optic system to the optimal incident angle $\theta_{opt}$ due to a mechanical variance of the bio memory disc and the bio memory disc drive apparatus. In addition, due to a longtime use, the use environments (temperature, humidity, etc.) of the bio memory disc drive apparatus may be changed, so that it is difficult to stably set the optic system to the optimal incident angle $\theta_{opt}$.

Namely, the optimal incident angle $\theta_{opt}$ is changed according to the bio memory disc, the bio memory disc drive apparatus, or the time of use thereof.

In the present invention, the SPR detecting unit performs scanning in a predetermined range of incident angle $\theta_{in}$ at every time of starting reading out of the assay site 132 of the to determine an optimal incident angle $\theta_{opt}$ where a contrast of light intensity between references spots of the assay site is maximized and, after introducing of the sample 200 to the assay site 132, photographs a change in the light intensity of a 2-D array of the assay site with a CCD or CMOS camera 832 to obtained a real-time SPR image.

In the bio memory disc according to the present invention, the SPR detecting unit sets the incident angle $\theta_{in}$ to the optimal incident angle $\theta_{opt}$, and after the sample 200 is introduced into the assay site, the SPR detecting unit obtains an SPR image intensity difference by comparing an after-reaction SPR image intensity with a before-reaction SPR image intensity.

In the bio memory disc according to the present invention, the SPR detecting unit sets the incident angle $\theta_{in}$ in to the optimal incident angle $\theta_{opt}$, and after the sample 200 is introduced into the assay site, the SPR detecting unit obtains a time-varying SPR image intensity difference by comparing an after-reaction SPR image intensity with a before-reaction SPR image intensity.

In the bio memory disc according to the present invention, the SPR detecting unit sets the incident angle $\theta_{in}$ to the optimal incident angle $\theta_{opt}$, and after the sample 200 is introduced into the assay site, the SPR detecting unit measures a sensorgram of each element.

In the bio memory disc according to the present invention, the SPR detecting unit repeats a scanning operation in a predetermined range of incident angle $\theta_{in}$ in a predetermined time interval after introducing of the sample to the assay site to measure a time-varying SPR angle or a time-varying SPR angle shift of each element of the array of the assay site.

The data measured in a predetermined time interval may be reconstructed by using curve fitting or interpolation.

The incident angle scanning operation of the SPR detecting unit is performed by precision rotation of the bio memory disc, radial movement of the slider 211 with the bio memory disc stopped, azimuthal movement of the slider 211, forward, backward, leftward, and rightward movements of a light source, or tilt adjustment of the light source. The slider 211 is moved by using the slider motor 109.

The precision rotation of the bio memory disc in the incident angle scanning operation is implemented by using a slot determining means or an FG signal determining means.

The precision rotation of the bio memory disc is implemented by fixing the light source 830 and rotating the spindle motor 102), so that the incident angle $\theta_{in}$ can be changed.

The radial or azimuthal movement of the slider in the incident angle scanning operation may be implemented by rotating the slider 211 on which the light source 830 is mounted.

The forward, backward, leftward, and rightward movements of the light source or tilt adjustment of the light source in the incident angle scanning operation may be implemented by controlling an electromagnet coupled with the light source 830 mounted on the slider 211.

An attractive force or a repulsive force generated by flowing a current through the electromagnet is used for a movement control means of the light source.

The forward, backward, leftward, and rightward movements of the light source or tilt adjustment of the light source in the incident angle scanning operation may be implemented by controlling a shape memory alloy coupled with the light source mounted on the slider 211.

The shape memory alloy is a member of which original shape can be recovered by applying heat or current. The deforming energy is used for the movement control means of the light source.

The forward, backward, leftward, and rightward movements of the light source or tilt adjustment of the light source in the incident angle scanning operation may be implemented by controlling a piezo device coupled with the light source mounted on the slider 211.

The piezo device is a member of which size is changed by applying a voltage. The deforming energy is used for the movement control means of the light source.

As the light source 830, at least one LED or laser diode may be used.

In the bio memory disc drive apparatus according to the embodiment, the optic system 114 may be mounted on the slider 211.

In addition, in the reading of the assay site 132, the assay site may be searched based on a difference between an SPR sensing signal measured before a reaction and an SPR sensing signal measured after the reaction and the dehydrating or drying of the assay site due to a high speed rotation of the bio memory disc.

FIG. 7A is a view illustrating an embodiment where the assay site 132 is read out from an SPR image by using a diffraction grating 840*a* or a micro prism 841*a*.

The diffraction grating 840*a* is constructed by coating a gold film 840*b* on a surface of a micro prism array 841*a* and fixing a capture probe 18 to a bio material linker 351*a*.

The light generated by a monochromatic, collimated, polarized light Source 830 is diffracted by the diffraction grating 840*a* or the micro prism array 841*a* and, after that, incident to the gold film 840*b* on the assay site 132 to form a surface plasmon on the surface of the gold film 840*b*.

At this time, the SPR image intensity is changed according to a degree of a specific binding between the sample 200 and the capture probe 18 on the surface of the gold film 840*b*.

Reference numeral 831 denotes the forward, backward, leftward, and rightward moving means or the tilt adjusting means. The incident angle $\theta_{in}$ can be changed by controlling the means.

Reference numeral 170 denotes a central aperture of the bio memory disc.

FIG. 7B is a view illustrating an embodiment where a groove pattern 842 constructed by coating gold (Au) on a surface of an upper disc member 1 made of plastic is used as a diffraction grating. The capture probe 18 is fixed on the surface of the gold-coated groove pattern 842. At the SPR angle $f_{SPR}$, the surface plasmon is formed on the surface of the gold-coated groove pattern 842. At this time, the reflectance is minimized. Accordingly, the intensity of the light reflected at the SPR angle is minimized. Since the SPR condition depends on a refractive index (or thickens) of a dialectic material on the surface of the gold-coated groove pattern 842 and that of the gold coated on the groove pattern 842, the specific binding reaction on the surface of the gold-coated groove pattern 842 can be quantitatively analyzed.

Figure 7C:
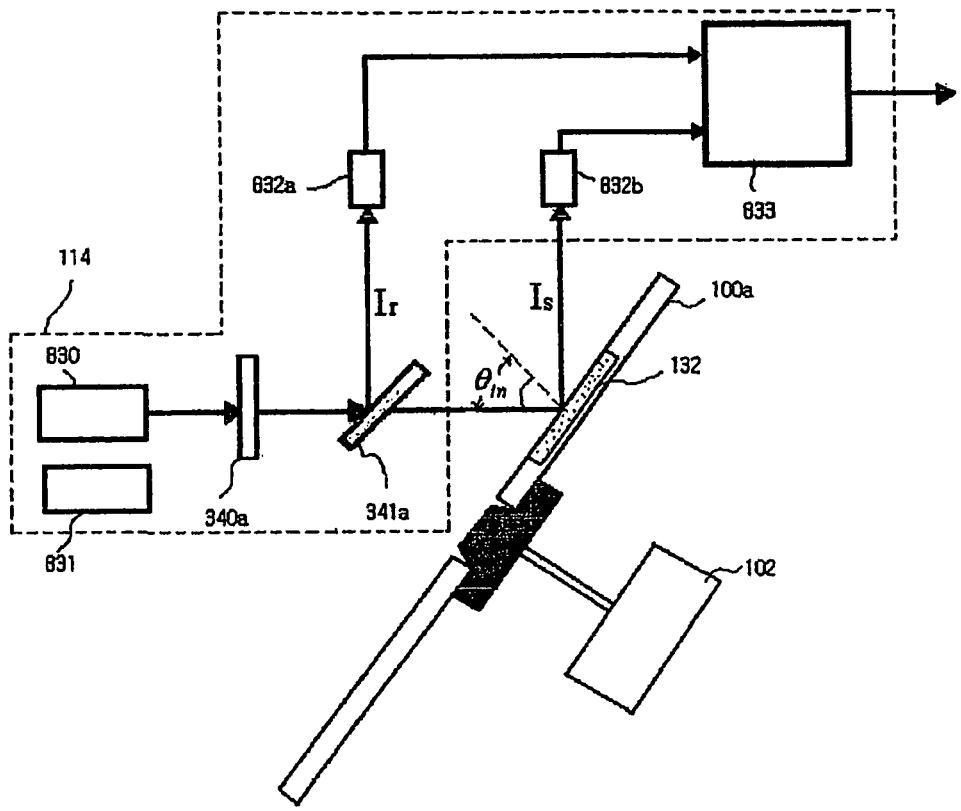
FIGS. 7C and 7D are views illustrating embodiments of an optic system for the SPR detecting unit.
Figure 7D:
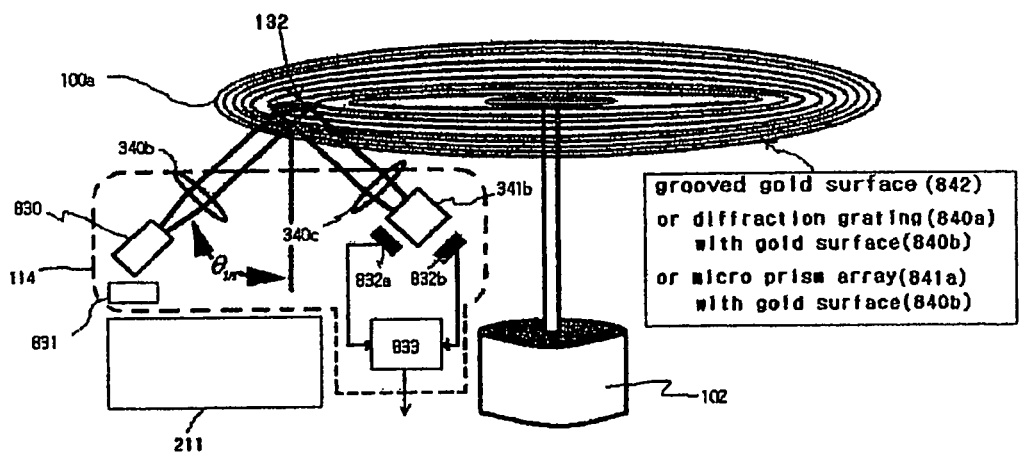

FIGS. 7C and 7D are views illustrating embodiments of an optic system for the SPR detecting unit.

The light generated by light source 830 is incident to the assay site 132, and the SPR image intensity is changed according to a degree of a specific binding between the sample 200 and the capture probe 18. The optic system 144 can be moved in the state that the optical system is mounted on the slider 211. The incident angle $\theta_{in}$ of the light source 830 can be changed by the forward, backward, leftward, and rightward moving means of the light source or the tilt adjusting means 831 of the light source. Reference numeral 102 denotes a spindle motor for rotating the bio memory disc 100*a*.

FIG. 7C illustrates an SPR detecting unit implemented with an optic system 114 including a reference photo sensor 832*a* for sensing an intensity of reference light generated from a light source 830, an SPR photo sensor 832*b* for sensing an intensity of light reflected from the assay site, and a driving circuit 833 for obtaining a ratio of signal components of the two sensors 832*a* and 832*b* and outputting a final SPR sensing signal.

Reference numerals 340*a* and 340*b* denote a polarizer and a beam splitter, respectively.

FIG. 7D illustrates an SPR detecting unit implemented with an optic system 114 including a collimator 340*b* for obtaining a parallel light from light generated by the light source 830, a lens used for detecting light reflected from the assay site 132, a polarizing beam splitter 341*b*, two SPR photo sensors 832*a* and 832*b*, and a driving circuit 833 for obtaining a ratio of signal components of the two sensors 832*a* and 832*b* and outputting a final SPR sensing signal. The light reflected from the assay site 132 is divided into S-polarization and P-polarization components by the polarizing beam splitter 341*b*, and the S-polarization and P-polarization components are sensed by the two SPR photo sensors 832*a* and 832*b*, respectively.

In order to remove noise and intensity fluctuation of the light source 830, the driving circuit 833 obtains a ratio of two polarization components based on the sensed S-polarization and P-polarization components and outputs a final SPR sensing signal.

FIGS. 8A to 8D are views illustrating embodiments of a strip 41 where multiple types of tumor markers are fixed on the porous membrane 41*c*. Reference numeral 41*a* denotes a conjugate pad, a sample pad or a combination of the sample pad and the conjugate pad, and reference numeral 41*b* denotes an absorbent pad. Reference numeral 41*c* denotes a porous membrane.

The tumor marker may be one or more selected from AFP, PSA, CEA, CA19-9, CA125, and CA15-3.

Figure 8A:
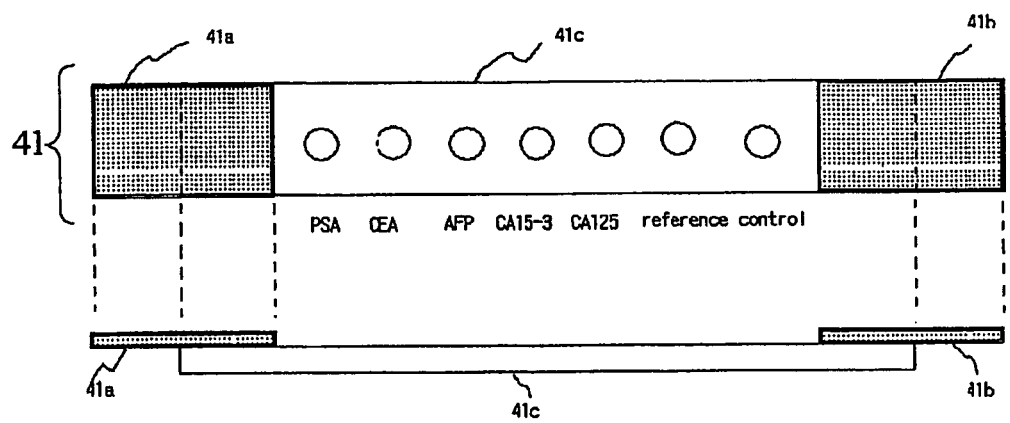
FIGS. 8A to 8D are views illustrating embodiments of a strip where multiple types of tumor markers are fixed on a porous membrane.
Figure 8B:
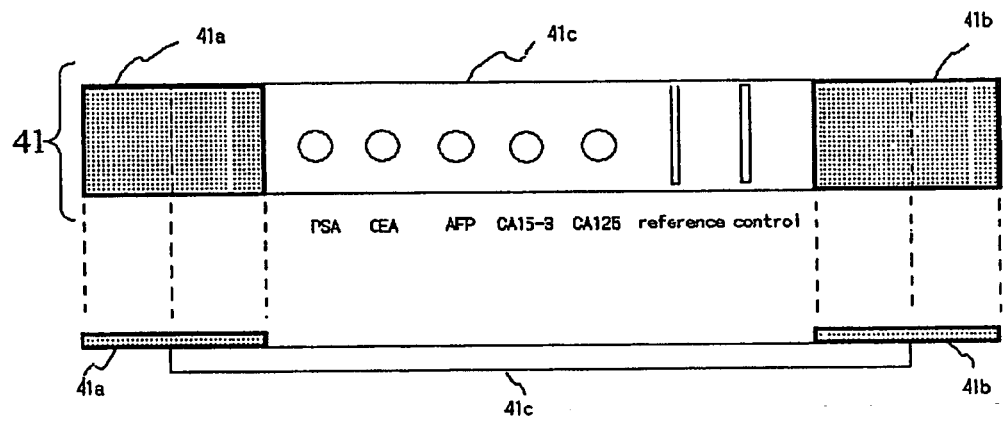
Figure 8C:
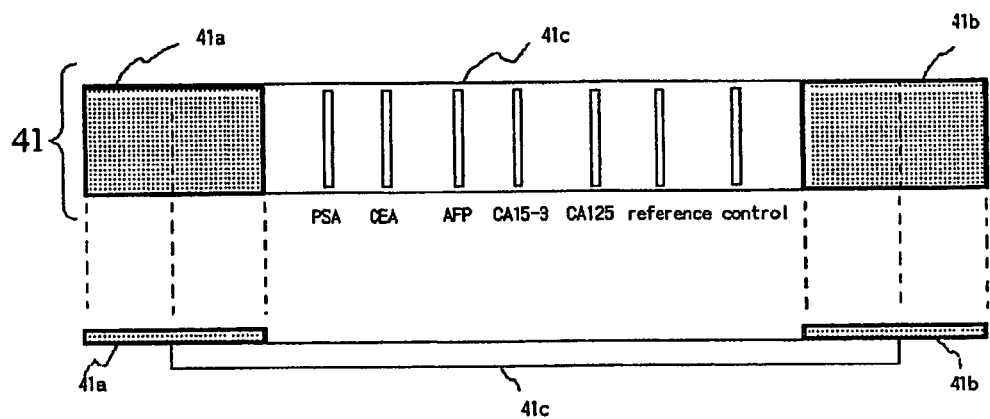

FIG. 8A is a view illustrating an embodiment where the tumor markers are fixed on the porous membrane 41*c* by using a spotting method. FIG. 8C is a view illustrating an embodiment where the tumor markers are fixed on the porous membrane 41*c* by using a lining method. FIG. 8B is a view illustrating an embodiment where the tumor markers are fixed on the porous membrane 41*c* by the spotting method and the reference line and the control line are fixed by using the lining method.

Figure 8D:
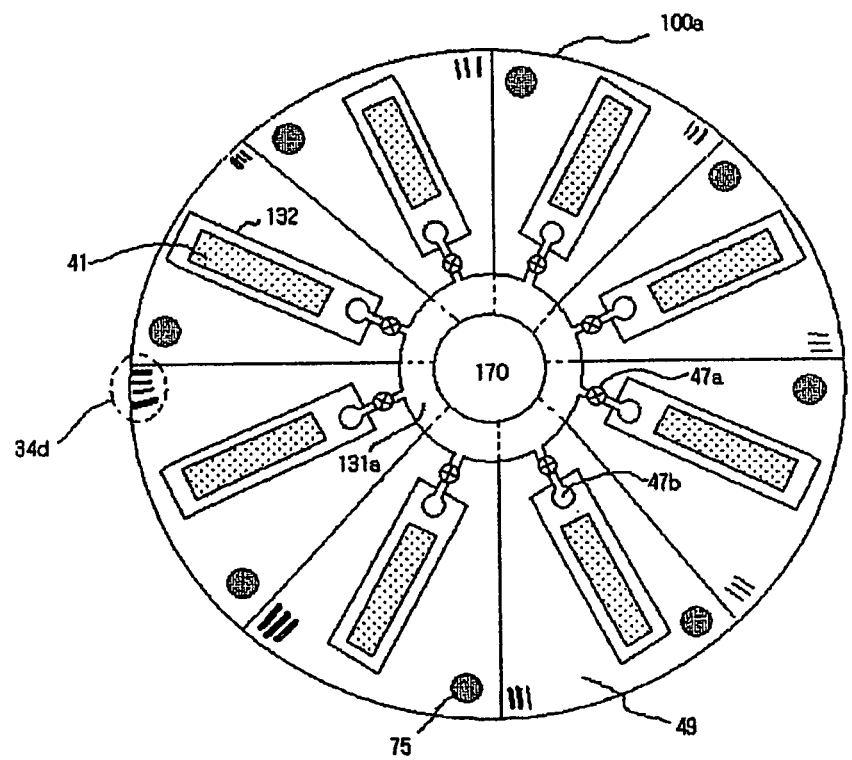

FIG. 8D is a view illustrating an embodiment of a bio memory disc used for performing a single-item assay on multiple-type samples, performing a multiple-item assay on single-type samples, or performing a multiple-item assay on multiple-type samples.

The bio memory disc includes one or more sample chambers 131a for storing a serum or plasma sample or an antigen or DNA sample. A plurality of the sample chambers 131a may store the same type samples for single-type sample assay. In addition, a plurality of the sample chambers 131a may store different types of samples for multiple-type sample assay. In addition, only one sample chamber 131a may be provided in case of injecting a sample for single-item assay.

In the bio memory disc according to the embodiment shown in FIG. 8D, eight assay sectors 49 are disposed in parallel. The strip 41, the valve 47a, the hydrophilic channel 47b are disposed in the assay site 132 of each assay sector 49. When the valve 47a is opened, the sample of the sample chamber 131a is transferred to the assay site 132 in a hydrophilic manner, and the sample specifically reacts with the multiple-item capture probes on the strip 41. Accordingly, the multiple-item assay can be performed in the single-item assay sector.

FIG. 8D is a view illustrating an embodiment where assay sector ID (Identification) information is indicated by a slot pattern or barcode pattern 34d disposed along a circumference of the assay sector 49. The assay sector ID information is detected by a slot detecting means 34a or an image sensor unit 39 and transmitted to the central controller 101.

Figure 9A:
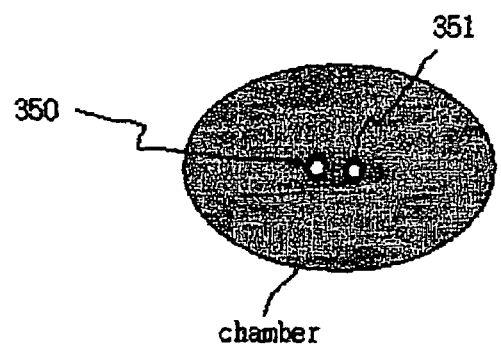
FIG. 9A is a view illustrating an embodiment of a chamber inlet and a chamber exhaust hole.

Since each of the assay sectors 49 is provided with a permanent magnet 75, the assay site searching process can be performed. In addition, since each assay site ID is recognized by the central controller 101, the image information on the reaction result of the assay site 132 captured by the image sensor unit 39 can be stored and managed in terms of the assay sectors FIG. 9A is a view illustrating an embodiment of a chamber inlet 350 for injecting various solutions including a buffer solution in the chamber and a chamber exhaust hole 351. The chamber exhaust hole 351 removes an air pressure so as to easily inject a liquid.

In the bio memory disc according to the embodiment, the chamber inlet 350 and the chamber exhaust hole 351 are disposed at the central portion of the chamber.

A fixed quantity injector, a dispenser, or a syringe needle is inserted into the chamber inlet 350 so as to inject the liquid (buffer solution, etc) into the chamber. If the chamber exhaust hole 351 are not provided, the chamber is hermetically closed, so that it is difficult to inject the liquid due to the air pressure of the chamber.

In addition, because the outer portion of the chamber is firstly filled with the injected liquid, the chamber exhaust hole 351 and the chamber inlet 350 are needed to be disposed at the central portion of the chamber.

Figure 9B:
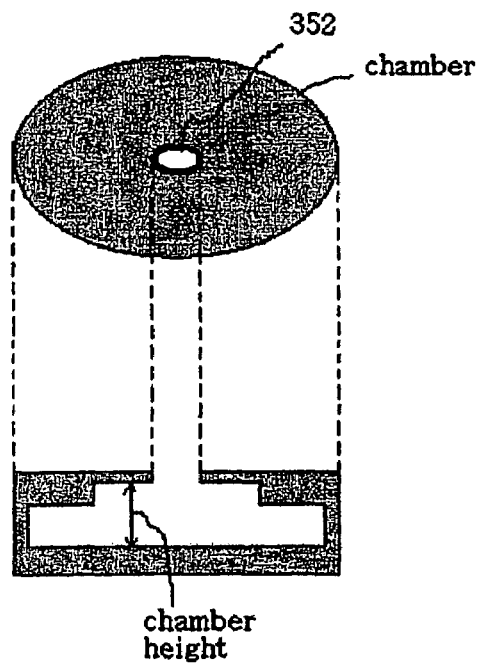
FIG. 9B is a view illustrating an embodiment of a chamber hole.

FIG. 9B is a view illustrating an embodiment of a chamber hole 352 constructed by integrating the chamber inlet 350 and the chamber exhaust hole 351.

In this case, a diameter of the chamber hole 352 is designed to be larger than a diameter of the fixed quantity injector, the dispenser, or the syringe, so that the chamber hole 352 serves as an chamber inlet as well as an exhaust hole. Since the diameter of the chamber hole 352 is larger, the chamber cannot be hermetically closed during the injection of the liquid.

In addition, because the outer portion of the chamber is firstly filled with the injected liquid, the chamber hole 352 is needed to be disposed at the central portion of the chamber. In addition, in order to prevent leakage of the liquid through the chamber hole 352, a height of the chamber can be differentiated. Namely, since a liquid has a preference to flow toward a portion of a smaller height of the chamber due to capillary phenomenon, the height of the chamber surrounding the chamber hole 352 is designed to be higher, so that the liquid can be apart from the chamber hole 352 as far as possible.

After the liquid is injected, the chamber exhaust hole 351 and the chamber inlet 350 or the chamber hole 352 are needed to be closed. If not, there is a problem in that the liquid may be leaked through these holes 350, 351, and 352 during delivery and sales thereof.

In the bio memory disc according to the embodiment, the chamber inlet 350, the chamber exhaust hole 351, or the chamber hole 352 may be closed with a sticker, or a CD label, or a UV adhesive.

The chamber exhaust hole 351 or the chamber hole 352 are closed during delivery and sales thereof because of leakage of the liquid stored in the chamber. But, the chamber exhaust hole 351 or the chamber hole 352 are opened so as for the liquid to move properly during the use thereof.

Figure 9C:
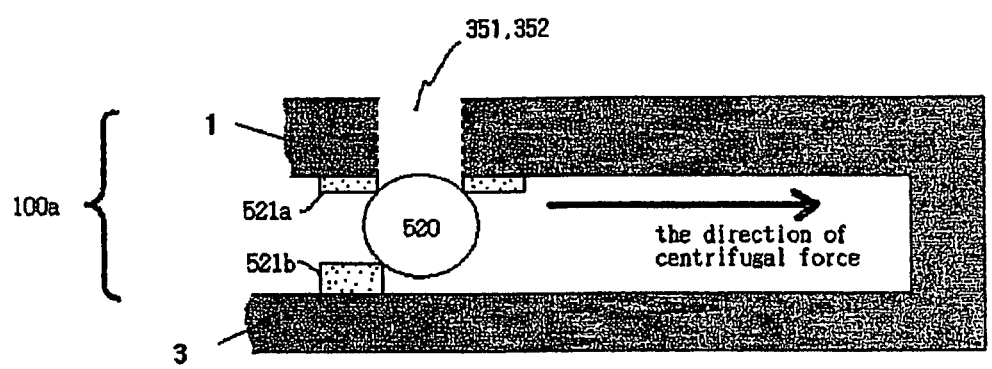
FIGS. 9C and 9D are views illustrating an embodiment where an chamber exhaust hole or an chamber hole is closed by using a steel ball and, after that, automatically opened at the time of use thereof.
Figure 9D:
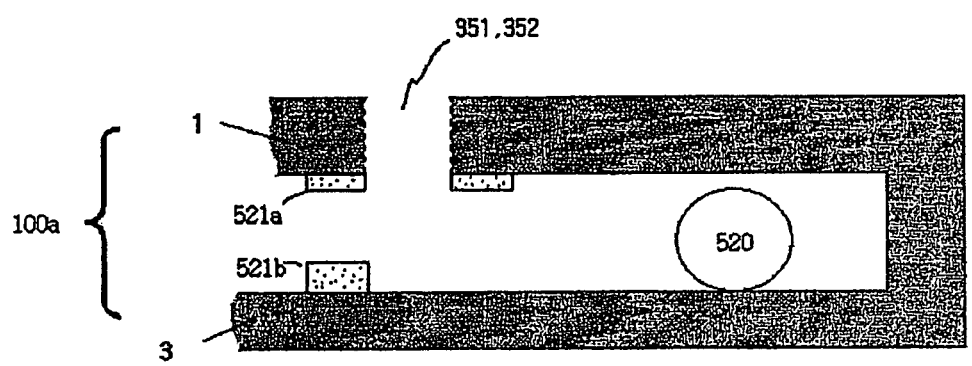

FIGS. 9C and 9D are views illustrating an embodiment where the chamber exhaust hole 351 is closed by using a steel ball 520 and, after that, automatically opened at the time of use thereof.

Before the bio memory disc is used, the chamber exhaust hole 351 and the chamber hole 352 are closed by the steel ball 520 and the adhesive means 521a and 521b. The steel ball 520 is fixed by the adhesive means 521a and 521b in the vicinity of the chamber exhaust hole 351, so that the chamber exhaust hole 351 is closed (see FIG. 9C).

When the bio memory disc is used, the bio memory disc 100a loaded on the bio memory disc drive apparatus is rotated at a high speed, so that a strong centrifugal force is exerted on the steel ball. As a result, due to the centrifugal force larger than the adhesive force of the adhesive means 521a and 521b, the steel ball 520 is detached, so that the chamber exhaust hole 351 is opened (see FIG. 9D).

In the bio memory disc according to the embodiment, the chamber exhaust hole 351 is closed by using the adhesive force between the steel ball 520 and the adhesive means 521a and 521b, and the chamber exhaust hole 351 is opened by using the centrifugal force larger than the adhesive force so that the steel ball 520 is detached.

In the present invention, the adhesive means 521a and 521b may be a cushioned double-sided tape or a cushioned rubber-coated member.

Figure 9E:
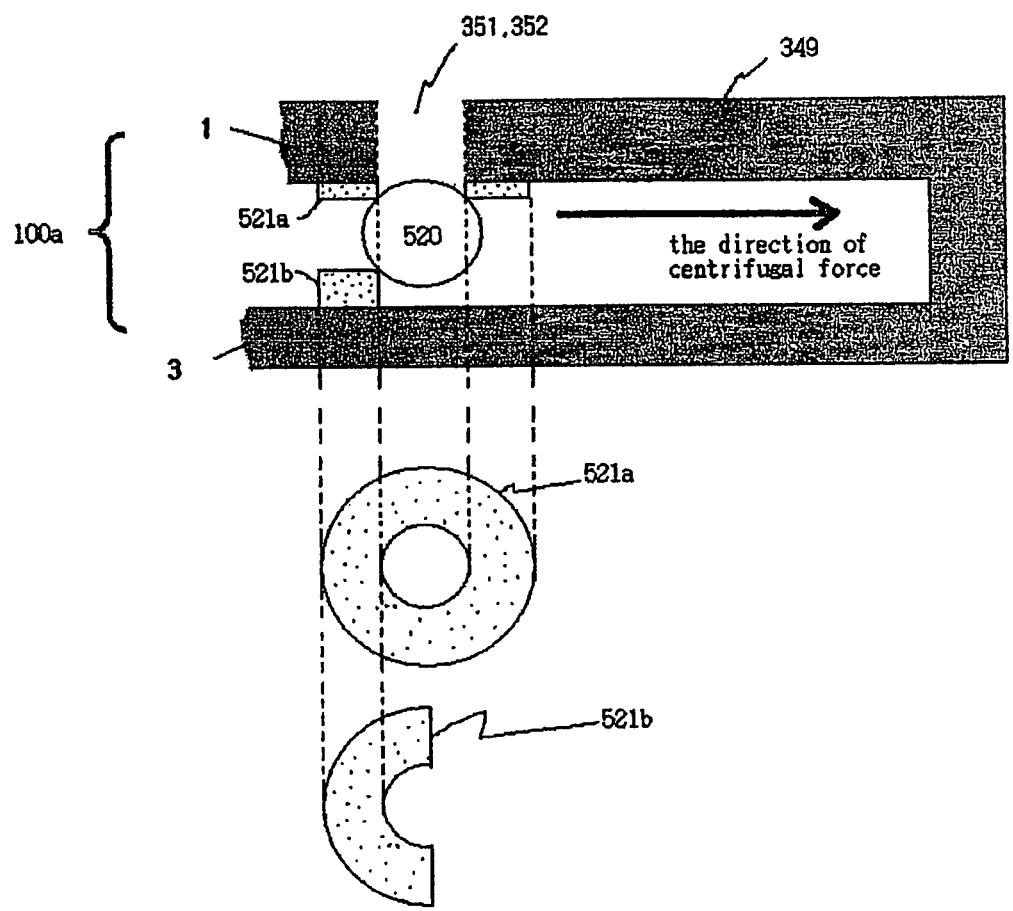
FIG. 9E is a view illustrating an embodiment of an attaching means.

FIG. 9E is a view illustrating an embodiment of adhesive means 521a and 521b.

Reference numeral 521a denotes a double-sided tape for allowing an upper portion of the steel ball 520 to be closely attached to the chamber exhaust hole 351. Therefore, the entire circumference of the upper portion of the steel ball 320 is designed to be exerted by the adhesive force.

Reference numeral 521b denotes a double-sided tape for allowing a lower portion of the steal ball 520 to be closely attached to the chamber body 349 and allowing the steel ball 530 to be easily detached by the centrifugal force. Therefore, a half of the circumference of the lower portion of the steel ball 520 is designed to be exerted by the adhesive force.

Figure 9F:
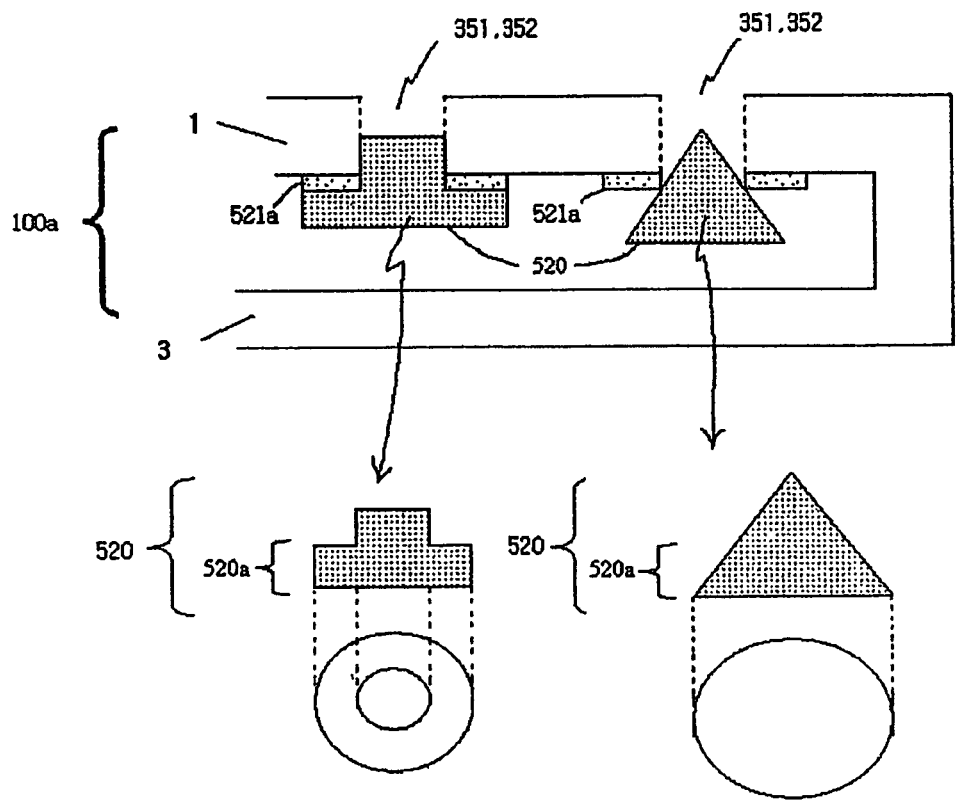
FIG. 9F is a view illustrating embodiments of various shape of a steel ball.

FIG. 9F is a view illustrating embodiments of various shapes (a triangular cylinder shape and a cap shape) of the steel ball 520. In the present invention, a head portion 520a of the steel ball 520 may be formed in a triangular cylinder shape or a cap shape so that the steel ball 520 can be easily detached from the chamber exhaust hole 351 by the centrifugal force.

In this case, only the double-sided tape 521a may be provided to closely attach the upper portion of the steel ball 520 to the chamber exhaust hole 351.

In another embodiment, in order to more effectively close the chamber exhaust hole 351, the chamber exhaust hole 351 may be coated with a cushioned rubber material, or the steel ball 520 may be coated with a cushioned rubber material.

Figure 9G:
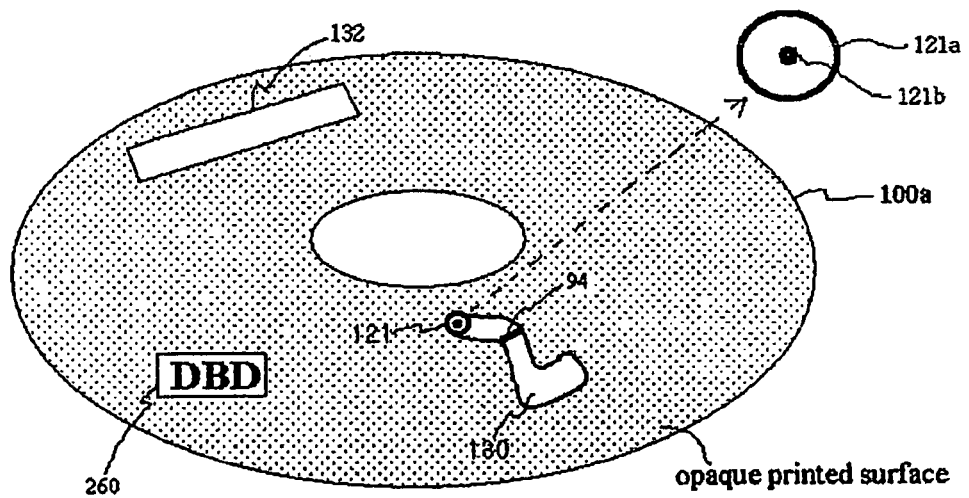
FIG. 9G is a view illustrating an embodiment of an upper printed surface of a bio memory disc.

FIG. 9G is a view illustrating an embodiment of a bio memory disc of which upper surface is subject to offset printing, silk screen printing, sticker printing, or CD label printing.

Here, DBD (Digital Bio Disc) 260 is a trademark or logo.

In the bio memory disc according to the embodiment, a sample inlet indicator is printed on an upper surface of an inlet cover 123 by using printing, silk screen printing, sticker printing, or CD label printing so as to inform a user of an accurate position of the sample inlet 121.

Reference numeral 121a and 121b denotes the sample inlet indicators for indicating a circumferential circle and a central point of the sample inlet 121, respectively. A user penetrates the sample inlet central point 121b of the inlet cover 123 with a syringe needle, an end portion of lancet, or an end portion of a sample injecting means and injects the sample in to the preparation chamber 130.

In the bio memory disc according to the embodiment, the sample inlet indicator includes a sample inlet circumferential circle and a sample inlet central point.

In the bio memory disc according to the embodiment, the sample inlet circumferential circle 121a and the sample inlet central point 121b is printed in black or red.

Reference numeral 94 denotes a fixed quantity indicating line drawn on the preparation chamber 130 so as to inform an operator of a minimum blood injection amount.

In the bio memory disc according to the embodiment, portions corresponding to the preparation chamber or the assay site are transparently printed or exposed in the offset printing, the silk screen printing, the sticker printing, or the CD label printing.

Figure 9H:
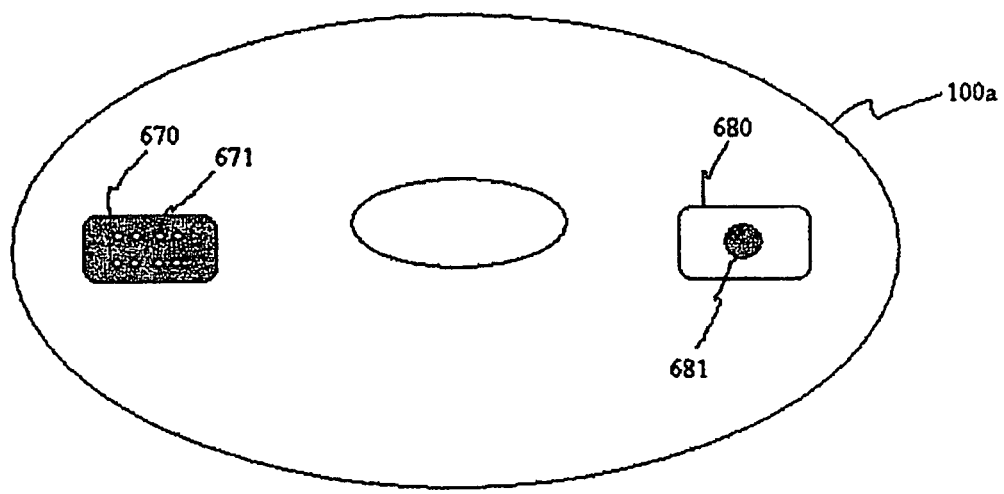
FIG. 9H is a view illustrating an embodiment of a dehumidifying chamber and a humidity sensing chamber of a bio memory disc.

FIG. 9H is a view illustrating an embodiment of a dehumidifying chamber 670 and a humidity sensing chamber 680 of a bio memory disc. The dehumidification chamber 670 contains a dehumidifying agent for removing humidity. In general, as a dehumidifying agent or a drying agent, zeolite, diatomite, silica gel, and zeolite gel are mainly used. Reference numeral 671 denotes an air hole of the dehumidification chamber 670.

The humidity sensing chamber 680 includes a humidity indicating card 681 for detecting whether or not the bio memory disc is previously exposed to humidity or immersed in a liquid. Accordingly, a problem of the bio memory disc caused from carelessness of a user can be recognized by a seller and a manufacturer at an A/S (after service) time. As a commercial humidity indicating card 681, there is Humonitor Card provided by Multisorb Technologies Inc.

Due to the humidity indicating card 681, it can be directly recognized whether or not an allowable humidity is contained in a closed space or a hermetically closed product container. As an example, the history that the bio memory disc is previously exposed to humidity may be indicated by a change in color from blue to red.

In the bio memory disc drive apparatus according to the embodiment, the image sensor unit 39 captures an image of the humidity sensing chamber 680 and transmits the image to the central controller 101, so that the central controller 101 can analyze whether or not humidity above the allowable humidity level is contained in the bio memory disc or store the image of the humidity sensing chamber 680 in a storage unit 112.

In the bio memory disc drive apparatus according to the embodiment, the central controller 101 analyzes the image of the humidity sensing chamber 680 and, in a case where it is determined that the bio memory disc is previously exposed to humidity over the allowable humidity level sends an alert message of informing the user of the fact, records the fact with time information and product ID of the bio memory disc as history management item in the storage unit 122, or remotely transmit the fact through the input/output unit 111 to an A/S (after service) center for the bio memory disc.

Figure 9I:
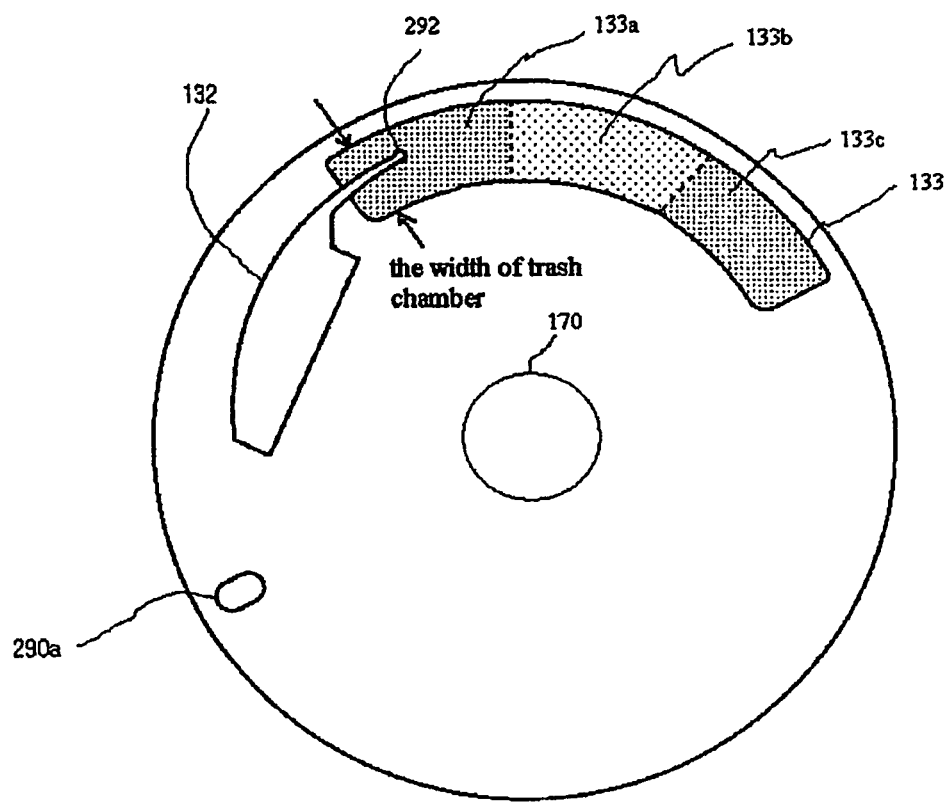
FIGS. 9I and 9J are views illustrating an embodiment of a trash chamber of a bio memory disc.
Figure 9J:
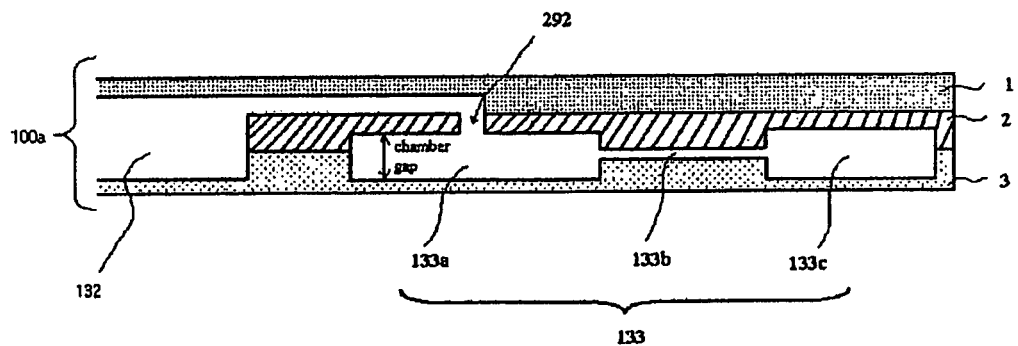

FIGS. 9I and 9J are views illustrating an embodiment of a trash chamber 133. In the embodiment, a valve dedicated for controlling an influx of the trash chamber 133 is not provided, and a chamber gap for preventing a counter flow provided to the trash chamber is modified.

Without the valve, a trash chamber inlet 292 is always opened, so that a liquid can be transferred from a previous-stage chamber 132 to the trash chamber 133 due to the centrifugal force. Since the trash chamber inlet 292 is always opened, there is a problem in that the liquid stored in the trash chamber 133 may be counter-flown to the previous-stage chamber 132.

In order to solve the problem, two approaches are used in the present invention. In the first approach, a size and position of the trash chamber inlet 292 are adjusted. The trash chamber inlet 292 is designed to be smaller than a width of the trash chamber and to be disposed at an inner portion of the bio memory disc as possible. If the trash chamber inlet 292 is disposed at an outer portion of the bio memory disc, the liquid stored in the trash chamber is mainly located at the outer portion of the bio memory disc due the centrifugal force generated from the rotation of the bio memory disc, so that the liquid can be easily counter-flown through the trash chamber inlet 292.

In the second approach, the chamber gap in the trash chamber 133 is modified in order to prevent the counter flow of the liquid stored in the trash chamber 133. FIGS. 9I and 9J illustrate the embodiment of the trash chamber. FIG. 9J is a cross sectional view illustrating main components of the trash chamber 133. In the embodiment, the trash chamber 133 is divided into large gap portions 133a and 133c and a small gap portion 133b. In the small gap portion 133b, a capillary attraction or a high surface tension is exerted on the liquid. Therefore, the liquid that is transferred to the large gap portion 133c of the trash chamber 133 cannot be easily counter-flown toward the large cap portion 133a, that is, toward the trash chamber inlet 292. Namely, the liquid that is transferred to the larger gap portion of the trash chamber 133 cannot be easily counter-flown due to the capillary attraction or the surface tension.

Reference numeral 290a denotes a reference hole used for alignment of the bio memory disc at the time of manufacturing and assembling the bio memory disc. The reference hole 290a is inserted into a fixture provided a jig.

Figure 9K:
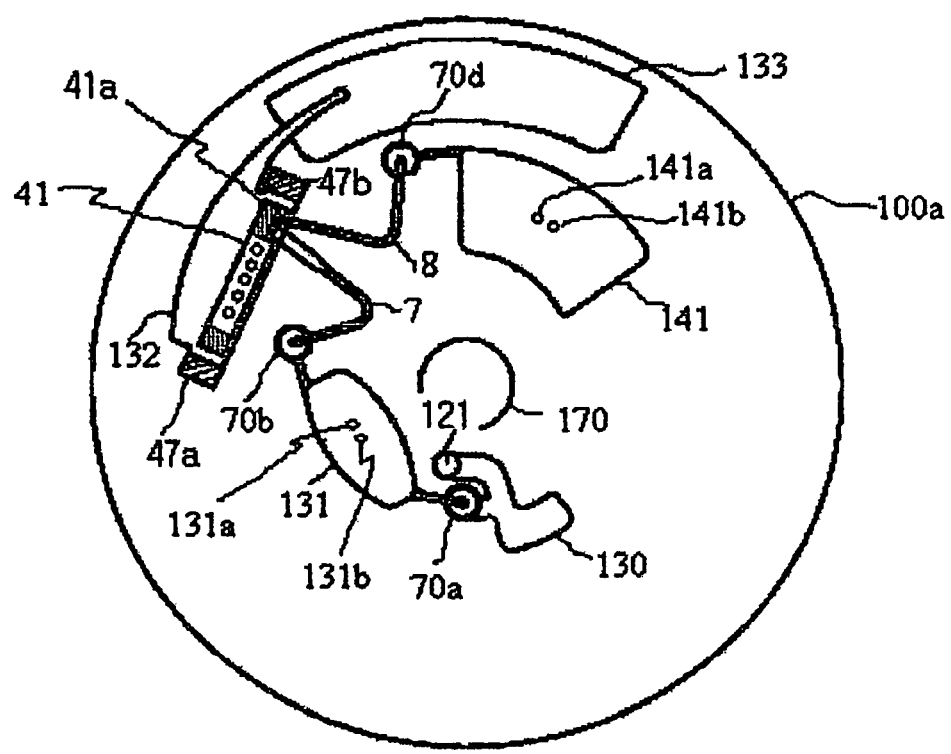
FIG. 9K is a view illustrating an embodiment of a strip disposed in an assay site of a bio disc.

FIG. 9K is a view illustrating an embodiment of a bio disc 100a where the strip 41 is disposed in the assay site 132.

As shown in FIG. 9K, the bio disc 100a includes a preparation chamber 130 for preparing a serum or plasma sample or an antibody or DNA sample from blood or a cell; a buffer chamber 131 for diluting the serum or plasma sample or the antibody or DNA sample with a diluting solution; an assay site 132 having a strip 41 where an array of capture probes for an Ag-Ab reaction with the prepared antigen sample or an array of capture probes for an hybridization reaction with the prepared DNA sample are fixed on a substrate; a washing chamber 141 for storing a washing solution used for a washing process; and a trash chamber 133 for collecting sludge generated in the washing process.

Reference numerals 70a, 70b, and 70d denote valves for controlling a flow of a fluid.

Reference numerals 7 and 8 denote V-shaped channel where a liquid valve is formed. The V-shaped channel 7 is provided to the outlet of the buffer chamber 131. The V-shaped channel 8 is provided to the outlet of the washing chamber 141. In addition, reference numerals 131a and 141a denote chamber inlets of the buffer chamber 131 and the washing chamber 141, respectively. Reference numerals 131b and 141b are chamber exhaust holes of the buffer chamber 131 and the washing chamber 141, respectively. In the present invention, the V-shaped channels are coated with a hydrophilic material. The buffer chamber 131 and the washing chamber 141 are filled with a diluting solution and a washing solution through the chamber inlets 141a and 131a before shipment at a factory. Now, operations of the bio memory disc shown in FIG. 9K are described.

<Embodiment>

(1) Before the bio memory disc 100a is used, a user samples blood by using a blood sampling tool and inject the blood through the sample inlet 121 to store the blood in the preparation chamber 130.

(2) When the bio memory disc is loaded on the bio memory disc drive apparatus, the bio memory disc drive apparatus rotates the bio memory disc at a high speed, so that the blood in the preparation chamber 130 is separated into serum (or plasma) and blood clot due to the centrifugal separation.

(3) When the valve 70a is opened, the separated serum (or plasma) is transferred to the buffer chamber 131. After that, by repetition of rotating and stopping of the bio memory disc, the serum (or plasma) is mixed and diluted with the diluting solution.

(4) After the bio memory disc is stopped, the valve 70b is opened, so that the serum (or plasma) stored in the buffer chamber 131 is transferred through the hydrophilic-coated V-shaped channel 7.

(5) When the serum (or plasma) is moved up to the sample pad 41a at the end portion (the strip 41) of the V-shaped channel 7, the serum (or plasma) is dropped on the sample pad 41a on the strip 41 through the fluid pumping transferring by using the valve 70b.

(6) The dropped serum (or plasma) is diffused into the strip 41 due to the porosity thereof and the capillary phenomenon. During the diffusion, the serum (or plasma) is specially bound with the capture probe on the strip 41.

(7) Subsequently, the bio memory disc is rotated at a high speed to dry the strip 41.

(8) Next, the valve 70d is opened, so that the washing solution stored in the washing chamber 131 is transferred through the hydrophilic-coated V-shaped channel 8.

(9) When the washing solution is moved up to the sample pad 41a at the end portion (the strip 41) of the V-shaped channel 8, the washing solution is dropped on the sample pad 41a on the strip 41 through the fluid pumping transferring by using the valve 70d.

(10) The dropped washing solution is diffused into the strip 41 due to the porosity thereof and the capillary phenomenon. During the diffusion, the washing solution removes components that is non-specially reacted on the strip 41.

(11) Subsequently, the bio memory disc is rotated at a high speed to dry the strip 41.

(12) Next, the reaction result of the strip 41 is read out by using an optical measurement unit, an electro-chemical measurement unit, an impedance measuring unit, an image sensor unit, a bio pit detecting unit, a fluorescence detecting unit, a radioactivity detecting unit, a QCM detecting unit, or an SPR detecting unit.

(13) Next, a diagnosis result according to the result of the reaction and a prescription is displayed on a computer monitor, and the diagnosis result and a questionnaire sheet is remotely transmitted to a doctor who is automatically or manually connected through an Internet. A patient waits a prescription of the doctor.

Reference numerals 47a and 47b are air holes capable of rapidly drying the strip 41 during the high speed rotation of the bio memory disc. The strip 41 is dried before the washing process, so that the washing solution can be efficiently diffused into the strip during the washing process. Accordingly, background components are efficiently washed.

Instead of the strip 41 in the assay site 132 shown in FIG. 9K, a capture probe may be fixed on a gold film, a self assembly monolayer (SAM), or various substrates to which the bio material can be linked. Various embodiments thereof are disclosed in International Patent Application No. PCT/KR02/00126, entitled "Nucleic acid hybridization assay method and device using cleavage technique responsive to complementary double strand of nucleic acids or oligonucleotides", which was filed on Jan. 27, 2002 and claims the priority of Korean Patent Application No. 10-2001-0003956 entitled "Nucleic acid hybridization assay method and device using cleavage technique responsive to complementary double strand or single strand of nucleic acids or oligonucleotides", filed on Jan. 27, 2001.

FIG. 10A is a view illustrating an embodiment of an outer appearance of a front-loading-type or side-loading-type bio memory disc drive apparatus. Reference numeral 751 denotes a case of the bio memory disc drive apparatus. Reference numeral 750 denotes a tray on which the bio memory disc 100 is loaded. In the present invention, the bio memory disc drive apparatus is provided with play and search buttons 745 and pause and eject buttons 746 for an optical disc.

In the present invention, the bio memory disc drive apparatus may be assembled with a main boy of a PC (personal Computer).

As shown in FIG. 10A, an operating state of the bio memory disc drive apparatus and a type of loaded disc that is an optical disc (CD, DVD, etc), a bio disc, or a memory disc are indicated by using a light emitting diode.

The bio memory disc drive apparatus is provided with a light emitting diode 741 indicating that the currently loaded disc is the bio disc and an operating state indicating light emitting diode 742 for indicating of the current assay result. Reference numeral 743 denotes a light emitting diode for indicating that the currently loaded disc is an optical disc. Reference numeral 744 denotes a light emitting diode for indicating that the currently loaded disc is a bio memory disc.

In the bio memory disc drive apparatus according to the embodiment, the operating state light emitting diode 742 is designed to blink during the operation of the bio memory disc drive apparatus where a disc is loaded.

In the bio memory disc drive apparatus according to the embodiment, the bio memory disc drive apparatus may further include a display unit for displaying an operating state of the bio memory disc drive apparatus and a type of loaded disc that is an optical disc (CD, DVD, etc), a bio disc, or a memory disc.

In the bio memory disc drive apparatus according to the embodiment, the display unit is an LCD unit for displaying an operating state of the bio memory disc drive apparatus and a type of loaded disc that is an optical disc (CD, DVD, etc), a bio disc, or a memory disc.

In the bio memory disc drive apparatus according to the embodiment, a main body of a personal computer (PC) provides a user with an GUI (graphic user interface) corresponding to the type of loaded disc that is an optical disc, a bio disc, or a memory disc.

Reference numeral 106 denotes a memory IC card inserting slot through which the memory IC card or the USB memory card is inserted.

Figure 10B:
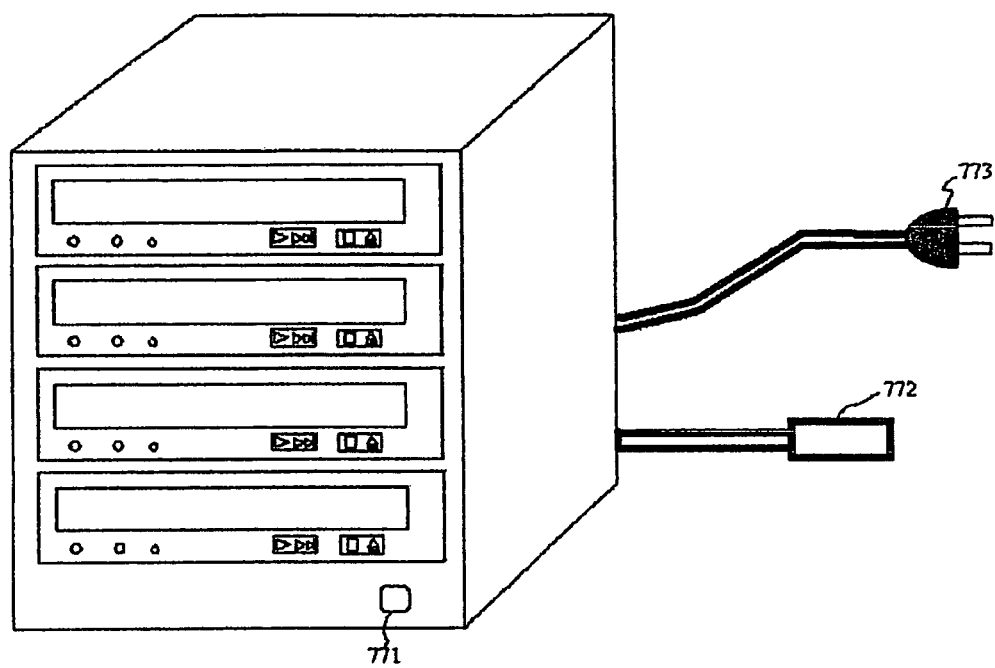
FIG. 10B is a view illustrating an embodiment of a bio memory disc drive apparatus assembly having a plurality of the bio memory disc drive apparatuses capable of loading a plurality of bio memory discs at one time.

FIG. 10B is a view illustrating an embodiment of a bio memory disc drive apparatus assembly having a plurality of the bio memory disc drive apparatuses capable of loading a plurality of bio memory discs at one time; According to the embodiment, the bio memory discs can be sequentially analyzed. In addition, a plurality of the bio memory discs can be simultaneously analyzed.

In the bio memory disc drive apparatus according to the embodiment, the bio memory disc apparatus assembly having a plurality of the bio memory disc drive apparatuses may be further provided with a computer for controlling the assembly and an input/output port 772 for interfacing with external apparatuses.

In the bio memory disc drive apparatus according to the embodiment, the input/output port 772 has a universal serial bus (USB) communication protocol, an IEEE 1394 communication protocol, an ATAPI communication protocol, or an Internet communication protocol.

Reference numeral 773 denotes a power plug. Reference numeral 771 denotes a main switch for the bio memory disc drive apparatus assembly having a plurality of the bio memory disc drive apparatuses.

Figure 10C:
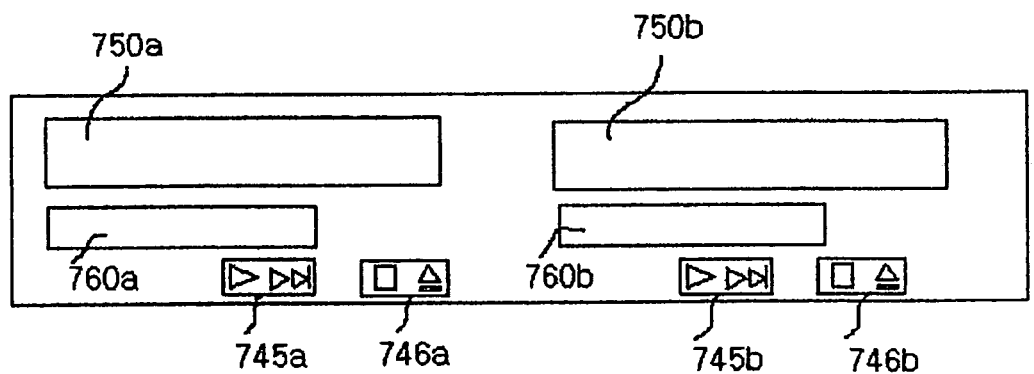
FIG. 10C is a view illustrating an embodiment of a double-deck-type bio memory disc drive apparatus.

FIG. 10C is a view illustrating an embodiment of a double-deck-type bio memory disc drive apparatus. In the present invention, the one side deck is provided with the bio memory disc drive apparatus, and the other side deck is provided with a DVD drive. Alternatively, both of the two side decks may be provided with the bio memory disc drive apparatuses.

The bio memory disc drive apparatus according to the embodiment may be a combo-type bio memory disc drive apparatus where one side deck is provided with the bio memory disc drive apparatus and the other side deck is provide with a video cassette recorder (VCR). Accordingly, while the VCR loaded on the other side deck is played, image information of the bio memory disc loaded on the one side deck can be recorded or stored at the same time Reference numerals 750a and 750b are trays used for front loading of the bio memory disc 100, the optical disc, or a video tape. In addition, the bio memory disc drive apparatus according to the present invention is provided with play and search buttons 745a and 745b and pause and eject buttons 746a and 746b for the optical disc or the VCR tape.

The LCD units 760a and 760b are used to display the operating state of the bio memory disc drive apparatus.

Figure 10D:
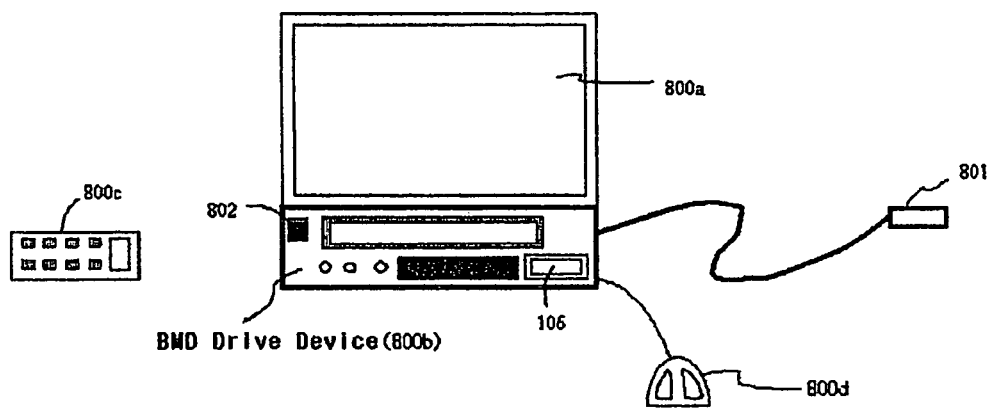
FIG. 10D is a view illustrating an embodiment of a bio memory disc drive apparatus integrated with a TV.

FIG. 10D is a view illustrating an embodiment of a bio memory disc drive apparatus 800b integrated with a TV 800a (an LCD TV, a PDP TV, or a CRT TV). The TV 800a is provided with an Internet input/output port 801 so as to transmit a diagnosis result of the bio disc 100a of bio memory disc drive apparatus 800b to a doctor, so that remote diagnosis can be performed.

Reference numeral 106 denotes a memory IC card inserting slot through which the memory IC card or the USB memory card is inserted. Reference numerals 800c and 802 denotes a remote controller and an IR receiver, respectively.

Reference numeral 800d denotes a mouse.

In the bio memory disc drive apparatus according to the embodiment, the TV displays an operating state of the bio memory disc drive apparatus 800b, a type of loaded disc that is an optical disc, a bio disc, or a memory disc, and a result of reading or diagnosis of the bio memory disc.

In the bio memory disc drive apparatus according to the embodiment, the TV provides a user with a graphic user interface (GUI) corresponding to the type of the loaded disc that is an optical disc, a bio disc, or a memory disc.

In the bio memory disc drive apparatus according to the embodiment, the TV is controlled by using a remote controller 800c so as to provide a user with an GUI (graphic user interface) corresponding to the type of loaded disc that is an optical disc, a bio disc, or a memory disc.

In the bio memory disc drive apparatus according to the embodiment, the TV is provided with a messenger which periodically informing a user of a time of periodic test or diagnosis through an e-mail or a window on a screen of the TV so as to easily perform follow-up management.

Figure 11A:
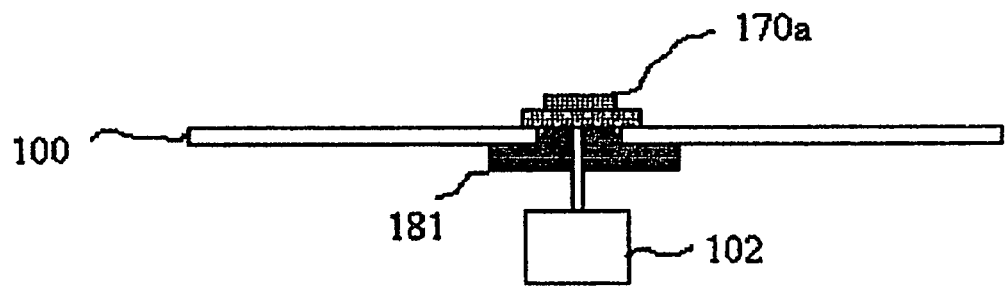
FIGS. 11A and 11B are views illustrating an embodiment of an outer appearance of a bio memory disc contained in a cartridge.
Figure 11B:
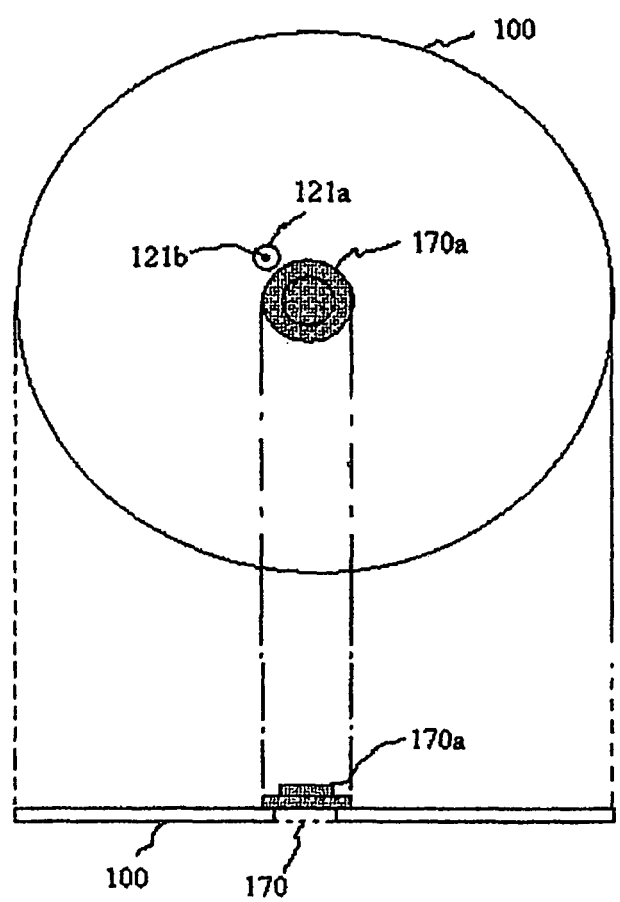

FIGS. 11A and 11B are views illustrating an embodiment of an outer appearance of a bio memory disc 100 contained in a cartridge. Reference numeral 170a denotes a central cap fixed on the disc aperture 170. FIG. 11A illustrates a state that the bio memory disc 100a is mounted on the turntable 181 of the bio memory disc drive apparatus. Reference numeral 170a denotes the central cap 170a. The central cap 17a is made of a magnetic material, so that the bio memory disc 100 can be stably mounted due to an attractive force between the central cap and a magnet built in the turntable 181. Reference numeral 102 denotes the spindle motor.

FIG. 11B is a detail view illustrating the bio memory disc 100 having the central cap 170a. Reference numeral 170 denotes a central aperture of the bio memory disc, and reference numerals 121a and 121b denote sample inlet indicators.

Figure 11C:
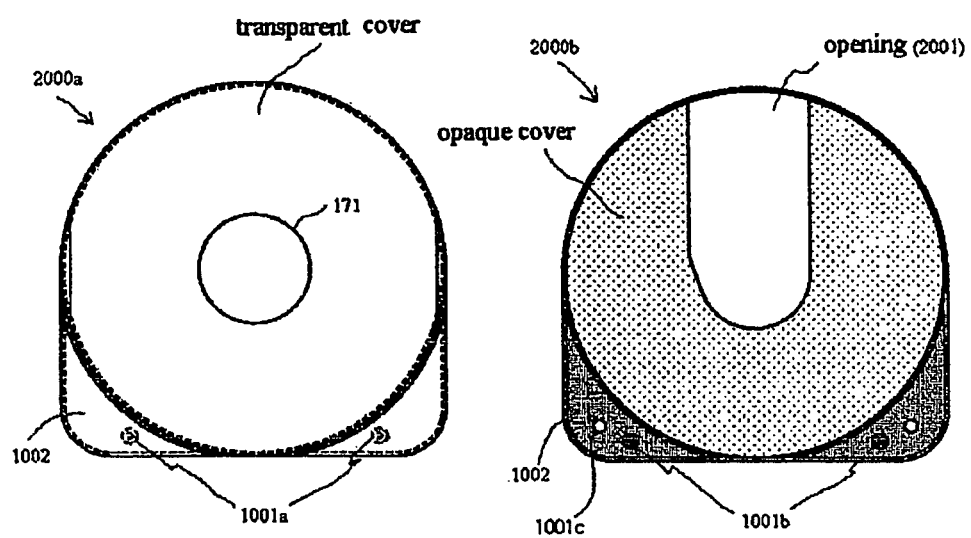
FIGS. 11C to 11E are views illustrating an embodiment of a cartridge-type bio memory disc.
Figure 11D:
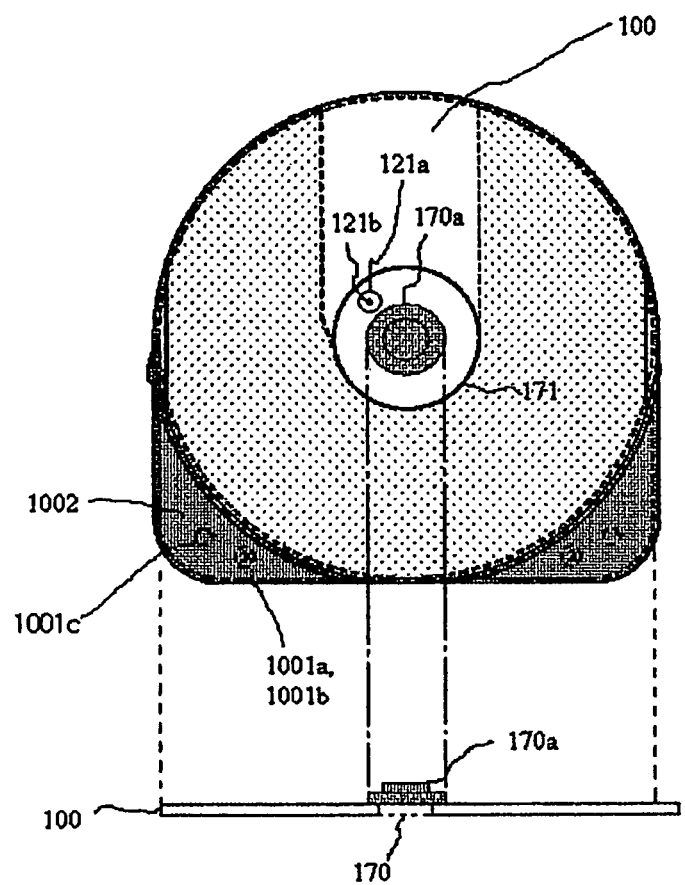
Figure 11E:
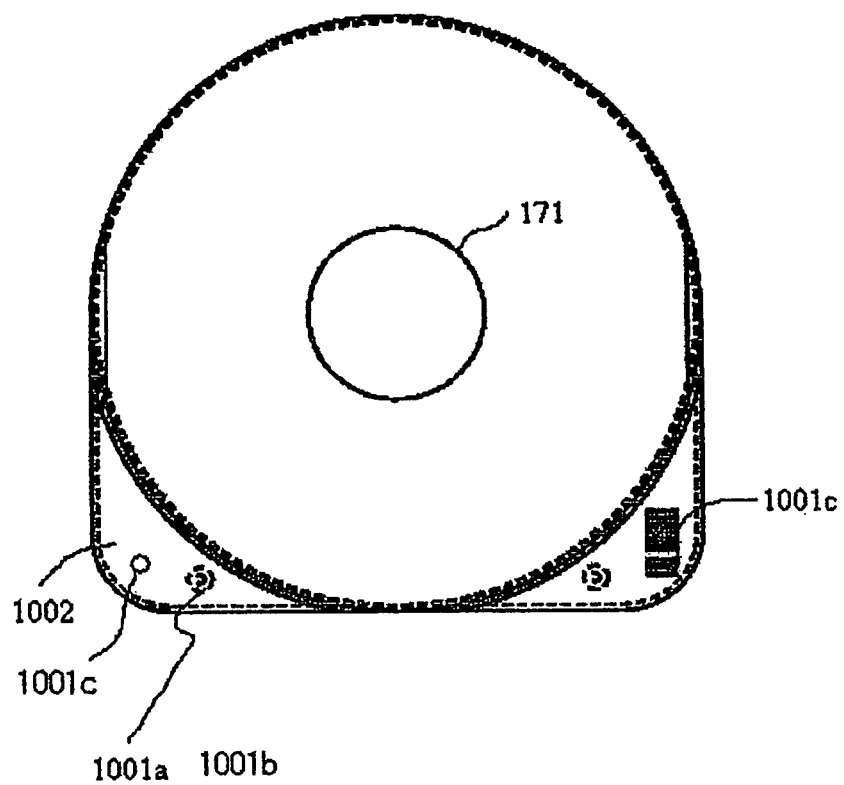

FIGS. 11C to 11E are views illustrating an embodiment of a cartridge-type bio memory disc where the bio memory disc 100 is contained in a cartridge. Reference numeral 1002 denotes a cartridge grip. Namely, the cartridge grip is held with a hand when the cartridge-type bio memory disc is loaded on the bio memory disc drive apparatus. Reference numeral 1001c denotes a hole which is engaged with a prominence of the tray in the bio memory disc drive apparatus when the cartridge-type bio memory disc is loaded on the bio memory disc drive apparatus. Due to the hole 1001c, the cartridge can be securely mounted on the tray.

FIG. 11C illustrates an upper cover 2000a and a lower cover 2000b of the cartridge.

Reference numerals 1001a and 1001b denote female and male engagement member of the upper and lower covers 2000a and 2000b, respectively. The cartridge-type bio memory disc is constructed by interposing the bio memory disc 100 having the central cap 170a between the upper and lower covers 2000a and 200b of the cartridge and pressing the upper and lower covers 2000a and 200b.

The upper cover 2000a is provided with an upper cover central aperture 171 for exposing sample inlet indicators 121a and 121b on the bio memory disc 100 at the central portion of the upper cover 2000a. In addition, the lower cover 2000b is provided with an opening 2001 for allowing the movable permanent magnet 5a to approach the bio memory disc or exposing the assay site 132.

FIG. 11D is a view illustrating an embodiment of a cartridge-type bio memory disc where the bio memory disc 100 having the central cap 170a is buried in the cartridge. An upper cover central aperture 171 is provided to expose sample inlet indicators 121a and 121b, so that a user can be easily inject a sample.

FIG. 11E is a view illustrating an embodiment of a barcode pattern 1001c which is printed on a cartridge grip 1002 to indicate the product ID.

In the bio memory disc according to the embodiment, the upper cover 2000a of the cartridge is a transparent cover.

While the present invention has been particularly shown and described with reference to exemplary embodiments thereof, it will be understood by those of ordinary skill in the art that various changes in form and details may be made therein without departing from the spirit and scope of the present invention as defined by the following claims.

INDUSTRIAL APPLICABILITY

According to the present invention, a bio memory disc, a bio memory disc drive apparatus, and an assay method using the bio memory disc drive apparatus are provided. More specifically, a bio memory disc drive apparatus including a bio memory disc on which a lab-on-a-chip process system including various assay-diagnosis units, a nucleic acid hybridization assay unit, or an immuno-assay unit and/or a semiconductor memory are disposed; and a controller for controlling and driving an optical disc (a CD, a DVD, etc.) and the bio memory and an assay method using the bio memory disc drive apparatus are provided. The bio memory disc drive apparatus and the assay method can be applied to an automatic diagnosis test apparatus which is directly used by a patient. In addition, a plurality of semiconductor memories are integrated in the bio memory disc so as to increase storage capacity, so that the bio memory disc can be used as a substitute for an existing hard disc of a computer.

The invention claimed is:

1. A bio memory disc drive apparatus comprising:
a bio memory disc performing a lab-on-a-chip process, wherein the bio memory disc that performs the lab-on-a-chip process includes:
a sample inlet;
a chamber for containing a buffer solution or a reaction solution;
an assay site comprising one of a porous membrane and a strip, wherein bio materials are fixed to the strip;
a channel through which a fluid flows between the chamber and the assay site; and
a detecting unit to read out the porous membrane or the strip;
a movable permanent magnet disposed under the bio memory disc;
an optical alignment unit allowing the search of the assay site, wherein the optical alignment unit comprises a permanent magnet disposed on the bio memory disc and the optical alignment is made between the detecting unit and the assay site when an attractive force is formed between the movable permanent magnet and the permanent magnet;
a slider on which the movable permanent magnet is mounted; and
a slider motor to control movement of the slider.

2. The bio memory disc drive apparatus according to claim 1, further comprising an induction coil disposed on the bio memory disc for receiving an external power, wherein the external power is supplied by a current induced through electromagnetic induction between an external magnetic field generating coil and the induction coil.

3. The bio memory disc drive apparatus according to claim 1, further comprising an induction coil disposed on the bio memory disc for receiving an external power, wherein the external power is supplied by a current induced through electromagnetic induction between at least one external permanent magnet and the induction coil during a high-speed rotation of the bio memory disc.

4. The bio memory disc drive apparatus according to claim 1, further comprising a solar cell disposed on the bio memory disc for receiving an external power.

5. The bio memory disc drive apparatus according to claim 1, further comprising an ABS (auto balancing system) chamber for containing a liquid material and/or steel balls to compensate for warbling generated due to an eccentricity of the bio memory disc during rotation of the bio memory disc.

6. The bio memory disc drive apparatus according to claim 1, further comprising a dehumidification chamber or a humidity sensing chamber.

7. The bio memory disc drive apparatus according to claim 1, wherein the chamber further includes a mixer chamber for mixing liquid materials in the chamber, wherein the mixer chamber includes: magnetic micro beads, wherein a speedy motion of the movable permanent magnet exerts an attractive force on the magnetic micro bead and induces a motion of the magnetic micro beads in the mixer chamber, so that the liquid material can be mixed.

8. The bio memory disc apparatus according to claim 1, wherein the chamber further includes a mixer chamber for mixing liquid materials in the chamber, wherein the mixer chamber includes:
magnetic micro beads; and
a non-rotatable magnet which is disposed at an upper or lower portion of the mixer chamber to exert an attractive force on the magnetic micro bead, wherein a rotation of the bio memory disc or a repetition of forward and inverse rotations of the bio memory disc induces a motion of the magnetic micro beads in the mixer chamber due to the attractive force of the non-rotatable magnet, so that the liquid material can be mixed.

9. The bio memory disc drive apparatus according to claim 1, wherein the chamber further includes a trash chamber comprising a series of chambers with large and small chamber gaps for preventing flowing backward of liquid.

10. The bio memory disc drive apparatus according to claim 1, wherein the assay site comprises the strip, wherein bio materials are fixed to the strip, the strip further comprising at least one test line, at least one reference line, and at least one control line.

11. The bio memory disc drive apparatus according to claim 1, further comprising a memory IC card slot used for inserting the memory IC card into the bio memory disc drive apparatus.

12. The bio memory disc drive apparatus according to claim 1, further comprising one of a light source, a laser generating unit, and a heater.

13. The bio memory disc drive apparatus according to claim 1, further comprising a spindle motor to perform a rotation cooling operation where the bio memory disc is rotated at a high speed to cool the chamber of the bio memory disc so as to adjust DNA amplification or an enzyme mechanism.

14. The bio memory disc drive apparatus according to claim 1, further comprising a spindle motor for rotating the bio memory disc,
wherein the bio memory disc further comprising:
a fluid hole for connecting the channel and another channel, and
a valve for opening and closing the fluid hole, wherein the value is constructed with a thin-film cylindrical magnet disposed at the fluid hole and a non-movable thin-film permanent magnet attached on an upper side of the disc disposed over the thin-film cylindrical magnet and the valve is closed by an attractive force between the thin-film cylindrical magnet and the non-movable thin-film permanent magnet.

15. A bio memory disc drive apparatus according to claim 1, wherein the detecting unit is any one of an optical measurement unit, an image sensor unit, an electro-mechanical measurement unit, impedance measuring unit, a bio pit detecting unit, a fluorescence detecting unit, a surface plasmon resonance (SPR) detecting unit, and a quartz crystal microbalance (QCM).

* * * * *

UNITED STATES PATENT AND TRADEMARK OFFICE
CERTIFICATE OF CORRECTION

| | | |
|---|---|---|
| PATENT NO. | : 8,951,779 B2 | Page 1 of 1 |
| APPLICATION NO. | : 12/158848 | |
| DATED | : February 10, 2015 | |
| INVENTOR(S) | : Jae-chern Yoo | |

It is certified that error appears in the above-identified patent and that said Letters Patent is hereby corrected as shown below:

Claims

Claim 8, Column 60, Line 21

After "disc" insert --drive--.

Signed and Sealed this
Thirteenth Day of October, 2015

Michelle K. Lee
*Director of the United States Patent and Trademark Office*